US012000838B2

(12) United States Patent
Loboda et al.

(10) Patent No.: US 12,000,838 B2
(45) Date of Patent: Jun. 4, 2024

(54) REAGENTS AND METHODS FOR ELEMENTAL MASS SPECTROMETRY OF BIOLOGICAL SAMPLES

(71) Applicant: Fluidigm Canada Inc., Markham (CA)

(72) Inventors: Alexander V. Loboda, Thornhill (CA); Olga Ornatsky, Richmond Hill (CA); Vladimir Baranov, Richmond Hill (CA); Nikita Zabinyakov, North York (CA); Anastasia Mavropoulos, Daly City (CA); Daniel Majonis, North York (CA); Bedilu Allo, Whitby (CA); Taunia Closson, Markham (CA)

(73) Assignee: STANDARD BIOTOOLS CANADA INC., Markham (CA)

( * ) Notice: Subject to any disclaimer, the term of this patent is extended or adjusted under 35 U.S.C. 154(b) by 651 days.

(21) Appl. No.: 17/050,716

(22) PCT Filed: Apr. 26, 2019

(86) PCT No.: PCT/US2019/029443
§ 371 (c)(1),
(2) Date: Oct. 26, 2020

(87) PCT Pub. No.: WO2019/210233
PCT Pub. Date: Oct. 31, 2019

(65) Prior Publication Data
US 2021/0239707 A1    Aug. 5, 2021

Related U.S. Application Data

(60) Provisional application No. 62/728,761, filed on Sep. 8, 2018, provisional application No. 62/728,594, filed
(Continued)

(51) Int. Cl.
*G01N 33/68*    (2006.01)
*C07K 1/13*    (2006.01)
*G01N 1/28*    (2006.01)

(52) U.S. Cl.
CPC .......... *G01N 33/6848* (2013.01); *C07K 1/13* (2013.01); *G01N 1/28* (2013.01); *G01N 2458/15* (2013.01); *G01N 2560/00* (2013.01)

(58) Field of Classification Search
USPC ....................................................... 436/173
See application file for complete search history.

(56) References Cited

U.S. PATENT DOCUMENTS

| | | | |
|---|---|---|---|
| 2014/0121117 A1 | 5/2014 | Tanner | |
| 2016/0194590 A1* | 7/2016 | Loboda | H01J 49/0027 435/307.1 |

(Continued)

FOREIGN PATENT DOCUMENTS

| | | |
|---|---|---|
| WO | 2011/075530 A1 | 6/2011 |
| WO | 2016090356 A1 | 6/2016 |

(Continued)

OTHER PUBLICATIONS

Mouhamad, Y. et al. Dynamics of polymer film formation during spin coating, Journal of Applied Physics 116, 123513 (2014) (Year: 2014).*

(Continued)

*Primary Examiner* — Xiaoyun R Xu
(74) *Attorney, Agent, or Firm* — Kilpatrick Townsend & Stockton LLP

(57) ABSTRACT

Embodiments of the present invention relate to reagents and their use for elemental imaging mass spectrometry of biological samples. The embodiments comprising methods for quantifying one or more analytes within a sample, comprising the steps of: (a) providing the sample, wherein the one
(Continued)

or more analytes are immobilized to a sample carrier, wherein the sample has been labelled with one or more mass tags comprising one or more labelling atoms, (b) performing mass cytometry on the sample to determine the level of the one or more labelling atoms, wherein the level of the one or more labelling atoms corresponds to the copy number of the one or more analytes.

20 Claims, 13 Drawing Sheets

Related U.S. Application Data on Sep. 7, 2018, provisional application No. 62/663,828, filed on Apr. 27, 2018.

(56) References Cited

U.S. PATENT DOCUMENTS

| | | | |
|---|---|---|---|
| 2017/0023583 A1 | 1/2017 | Ornatsky | |
| 2017/0059574 A1* | 3/2017 | Maecker | G01N 33/585 |
| 2017/0370942 A1 | 12/2017 | Picotti et al. | |

FOREIGN PATENT DOCUMENTS

| | | |
|---|---|---|
| WO | 2016/109603 A1 | 7/2016 |
| WO | 2018026898 A1 | 2/2018 |

OTHER PUBLICATIONS

Hafner, D. et al. Mussel-Inspired Polymer Carpets: Direct Photografting of Polymer Brushes on Polydopamine Nanosheets for Controlled Cell Adhesion, Adv. Mater. 2016, 28, 1489-1494 (Year: 2016).*

Schulz et al., "Silver Nanoparticles For The Detection Of Cell Surface Antigens In Mass Cytometry Assays", Cytometry A, vol. 91, No. 1, Jun. 28, 2016, pp. 25-33.

European Application No. EP19793849.1 received an, Extended European Search Report, dated Dec. 17, 2021, 9 pages.

PCT/US2019/029443 received an International Search Report and Written Opinion dated Sep. 3, 2019, 15 pages.

* cited by examiner

REAGENTS AND METHODS FOR ELEMENTAL MASS SPECTROMETRY OF BIOLOGICAL SAMPLES

CROSS REFERENCE TO RELATED APPLICATIONS

This application claims priority to U.S. Provisional Patent Application No. 62/663,828 filed Apr. 27, 2018 titled "REAGENTS AND METHODS FOR ELEMENTAL MASS SPECTROMETRY OF BIOLOGICAL SAMPLES", U.S. Provisional Patent Application No. 62/728,594 filed Sep. 7, 2018 titled "REAGENTS AND METHODS FOR ELEMENTAL MASS SPECTROMETRY OF BIOLOGICAL SAMPLES", and to U.S. Provisional Patent Application No. 62/728,761 filed Sep. 8, 2018 titled "REFERENCE PARTICLE BASED NORMALIZATION FOR IMAGING MASS SPECTROMETRY," the entire disclosures of which are hereby incorporated by reference, for all purposes, as if fully set forth herein.

BACKGROUND

Mass spectrometry, including mass cytometry, enables multiparametric analysis of samples. Samples can be labelled with element tagged reagents such as antibodies, nucleic acids, proteins etc. and this allows for many target proteins, nucleic acids and/or carbohydrates etc. to be detected simultaneously, as each target protein is associated with a unique element or isotope through a binding partner intermediate. The technique encompasses both the analysis of samples in solution (e.g. cells or beads) in mass cytometry, in a process akin to flow cytometry. Alternatively, in imaging mass cytometry, samples such as tissue sections can be imaged by successively removing labelled material from the sample and building up an image of the sample from the element/isotopes from the labelled reagents.

Previously, these analyses have been limited to cellular samples. Thus a need remains outstanding for the detection and quantitation the levels of analytes in solution.

FIELD OF THE INVENTION

This invention relates to the detection and quantitation of analytes in samples by mass cytometry, including imaging mass cytometry.

SUMMARY OF THE INVENTION

The inventors of embodiments of the present invention have opened up a new avenue in the application of mass cytometry in the enablement of precise quantitation of samples immobilised to solid supports. In particular, when molecules to be analysed (i.e. analytes) that are bound to solid surfaces are either directly or exposed to/reacted with/hybridized to e.g. other biological macromolecules conjugated to distinguishing tags containing labelling atoms, the analyte macromolecules can be detected in a quantitative manner using mass cytometry.

In particular, the inventors have provided a method for the quantitation of soluble analytes from solution (e.g. proteins, nucleic acids, carbohydrates in solution which are immobilised to the solid phase by being bound by an immobilised reagent, such as a capture element which is an SBP as described herein). Herein, the inventors demonstrate a linear response curve in the levels of elemental ions derived from labelling atoms in mass tags detected with increasing amounts of analyte, demonstrate this in a multiplexed setting, and do so for both protein and DNA.

Accordingly, embodiments of the present invention provide methods for quantifying one or more analytes within a sample, comprising the steps of: (a) providing the sample, wherein the one or more analytes are immobilised to a sample carrier, wherein the sample has been labelled with one or more mass tags comprising one or more labelling atoms, (b) performing mass cytometry on the sample to determine the level of the one or more labelling atoms, wherein the level of the one or more labelling atoms corresponds to the copy number of the one or more analytes.

The method can be performed on analytes immobilised on a sample carrier which is a particle/bead in mass cytometry, and on analytes immobilised on a sample carrier which is a planar surface by imaging mass cytometry based techniques, and can be performed in a variety of different ways, an exemplary selection of which is discussed below. Thus the method has broad application.

The inventors also provide new mass cytometry sample carriers which comprise surface modifications that are optimised for use in the immobilisation of soluble analytes, so as to enable further improvements to the quantitation methods. In particular, the surface modifications increase the capacity of the mass cytometry sample carrier for immobilisation of soluble analytes and/or reduce non-specific adsorption of analytes to the mass cytometry sample carrier. Accordingly, embodiments of the present invention provide a mass cytometry sample carrier comprising a substrate with a surface modification, such as a non-fouling layer (e.g. surface assembled monolayer), a capacity enhancing layer (such as a polymer brush), and a non-fouling layer and a capacity enhancing layer. Embodiments of the present invention also provide methods of making mass cytometry sample carriers according to the invention. Capture elements are attached to the surface modification(s) to enable specific capture of analytes from solutions (e.g. the solution in which particular mass cytometry sample carriers are suspended; or solutions which have been dispensed onto the surface of a planar mass cytometry sample carrier, such as a glass or plastic slide).

Further, the inventors have developed methods for attaching the surface modifications to a wide range of planar substrates, formed of various different materials. This technique involves forming a polydopamine layer on the planar mass cytometry sample carrier substrate. Accordingly the invention provides a planar mass cytometry sample carrier comprising a polydopamine layer, such as wherein (i) capture elements are attached to the polydopamine layer and/or (ii) a 3D polymer is attached to the polydopamine layer, optionally wherein capture elements are attached to the 3D polymer, such as a 3D polymer brush.

For the purpose of this application, the term 3D in the context of a 3D polymer brush refers to a polymeric species that extends out from a surface in the dimension perpendicular to the direction of the surface to which it is bound. Such a 3D polymer brush differs from a polymer-coated 2D surface, wherein any bound substrates do not extend in a direction perpendicular with the direction of the surface.

DETAILED DESCRIPTION OF THE INVENTION

Figure 1A:
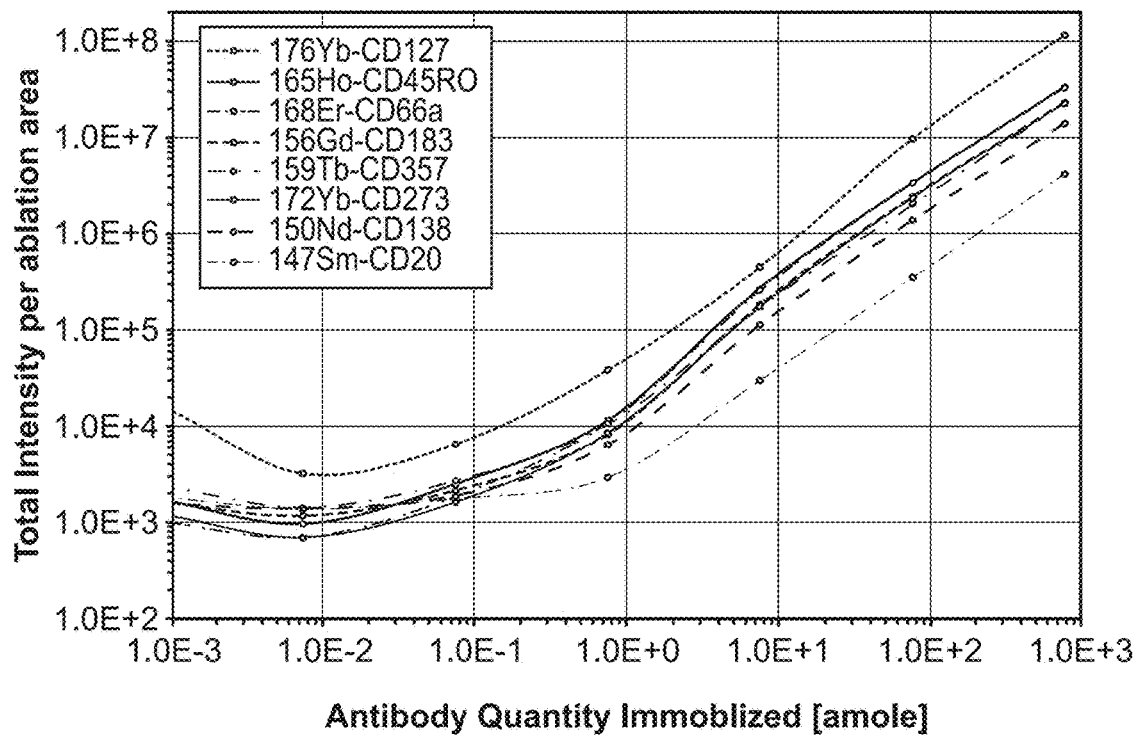
FIG. 1. Assessment of multiplex antibody spotting and acquisition using IMC. Different quantities of metal-tagged antibody mix were manually spotted on NHS activated hydrogel coated glass slide followed by quenching and rinsing with washing buffer and ddH$_2$O. Graphs (A&B) are show total intensities per ablation area (500×500 µm) versus antibody concentration (A) and number of antibody molecule spotted per pixel (B). Each point represents the mean signal intensity of triplicate IMC acquisitions.
Figure 1B:
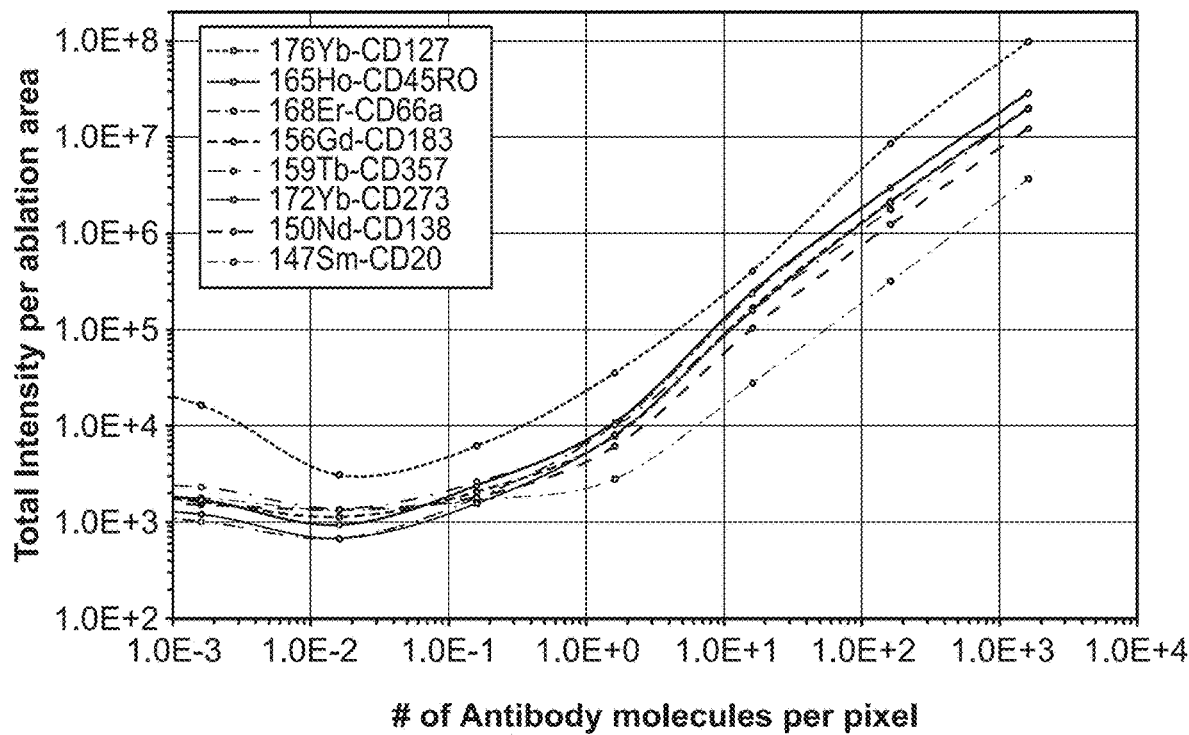

Mass cytometry, including imaging mass cytometry, relies on the labelling of target species (also referred to as analytes herein and in the field) on or in a sample using mass-tagged SBPs that bind to specific analytes (proteins, nucleic acids, sugars, metabolites etc.).

When the analytes are part of a cell, then the SBPs can be applied to label analytes on or in the cell. However, analytes in solution (e.g. proteins secreted by cells) previously could not be analysed in a simple manner. Embodiments of the present invention enable new ways to analyse samples by providing reagents and methods which enable immobilisation and analysis of analytes in a quantitative manner.

To maximise the applications of the method, the inventors have also developed new mass cytometry sample carrier reagents for maximising immobilisation of analytes; thereby improving the sensitivity and specificity of the technique.

Quantitation of Analytes in Solution Using Mass Cytometry, Including Imaging Mass Cytometry Thus, embodiments of the present invention provide a method for quantifying one or more analytes within a sample, comprising the steps of: a. providing the sample, wherein the one or more analytes are immobilised to a mass cytometry sample carrier, wherein the sample has been labelled with one or more mass tags comprising one or more labelling atoms, b. performing mass cytometry on the sample to determine the level of the one or more labelling atoms, wherein the level of the one or more labelling atoms corresponds to the copy number of the one or more analytes to quantify the analytes.

Quantitation of the analyte may be relative (i.e. with respect to other proteins within the mixture, or the same protein in different samples) or it may be absolute, via use of a calibration curve, as discussed herein below.

Typically, the sample is provided as an aqueous solution, such that when the sample contacts the mass cytometry sample carrier and when incubated under suitable conditions, analytes in the sample are specifically bound by capture elements on the mass cytometry sample carrier, thereby immobilising the analytes previously in solution and, in turn, thereby enabling their analysis using the exquisite resolving and quantitation powers of mass cytometry, including imaging mass cytometry.

Typically, the sample is non-covalently immobilised to the mass cytometry sample carrier by a capture element. However, in some instances, covalent immobilisation may be employed without use of a capture element. Immobilisation conditions are selected as appropriate depending upon the species to be immobilised. For instance, immobilisation conditions include incubation overnight at 4° C.

The mass cytometry sample carrier can be based on any solid phase that can be modified as discussed herein. Examples include glass, silica, aluminium, plastic, polystyrene, and encompass planar surfaces in the form, e.g., of microscope slides, as well as particulates such as beads. Indeed, any object that can be covered in a thin sticky film to which an SAM and/or 3D polymer can be attached can function as a mass cytometry sample carrier (e.g. metal, glass or wood).

The mass cytometry sample carrier may be completely coated in the surface modifications discussed herein. Alternatively, sometimes only a certain region or certain regions of the mass cytometry sample carrier, such as discrete regions (i.e. abutting or spaced apart regions), may be coated in the surface modification. In some embodiments, the mass cytometry sample carrier comprises 2 or more, such as 5 or more, 10 or more, 25 or more, 50 or more, 100 or more, 500 or more, 1000 or more or 5000 or more discrete regions of surface modifications. In some instances, different discrete regions may be modified in a different manner. In some instances, multiple discrete regions of the same mass cytometry sample carrier may contain the same surface modifications (including the same capture element(s)), so as to allow multiple samples to be run on the mass cytometry sample carrier, and/or for repeat readings to be taken from the same sample on a single mass cytometry sample carrier. Different discrete regions may each contain just a single type of capture element for binding a specific analyte, however to do so would fail to take advantage of the capacity for multiplexing provided by IMC. Typically, at least 2, such as 5 or more, 10 or more, 25 or more, 50 or more or 100 or more different types of capture element will be present on a mass cytometry sample carrier. Where the mass cytometry sample carrier comprises discrete regions, one or more of the discrete regions can each comprise at least 2, at least 3, at least 4, at least 5, at least 6, at least 7, at least 8, at least 9, at least 10, at least 20, at least 30, at least 40, at least 50, or at least 100 different kinds of capture elements.

In some instances, a set of particles can be used, with each particle comprising a different capture element or set of capture elements, thereby meaning that different beads in the set immobilise different analytes or sets of analytes from a sample.

Where cells and solution phase molecules are analysed on the same mass cytometry sample carrier, cells may be immobilised to a first discrete region (or a set thereof with the same capture elements) and the soluble analytes may be immobilised to a second discrete region (or a set thereof with the same capture elements).

Thus the invention provides a mass cytometry sample carrier comprising a substrate comprising a surface modification, wherein the surface modification comprises one of more capture elements capable of binding to molecules in a sample.

Mass cytometry sample carriers according to the invention thus can comprise one or both of (i) a surface modification which is an anti-fouling layer (wherein the mass cytometry sample carrier comprising the surface modification layer has a lower occurrence of non-specific adsorption than a corresponding mass cytometry sample carrier lacking the surface modification), and/or (ii) a surface modification which is a capacity enhancement layer (wherein the mass cytometry sample carrier comprising the surface modification layer has a higher binding capacity than a corresponding mass cytometry sample carrier lacking the surface modification).

One way to quantify the difference in the non-specific adsorption of a mass cytometry sample carrier comprising the surface modification layer and a mass cytometry sample carrier lacking said surface modification is to use imaging mass cytometry. Thus, an unmodified mass cytometry sample carrier surface can be exposed to a solution comprising mass-tag labelled biomolecules. The surface can then be washed and imaging mass cytometry conducted on the surface. A mass cytometry sample carrier surface comprising a surface layer (e.g. an SAM or 3D polymer brush), can be exposed to the same solution of mass-tag labelled biomolecules. This surface can also be washed and imaging mass cytometry conducted. The differences in the intensities of the signals detected for the elements present in the mass tags adsorbed to the surface of the respective slides can be used to quantify the difference in non-specific binding between the two surfaces and/or capacity. In some embodiments a mass cytometry sample carrier according to the invention comprises a modified area of its surface that has at least two-fold, for instance at least three-fold, at least four-fold, at least five-fold, at least ten-fold or at least 100-fold lower non-specific adsorption versus an equally sized surface area of a non-modified sample carrier. In some embodiments a mass cytometry sample carrier according to the invention comprises a modified area of its surface that has at least two-fold, for instance at least five-fold, at least ten-fold, at least 100-fold, or at least 1000-fold greater capacity versus an equally sized surface area of a non-modified sample carrier.

Accordingly, the invention provides a mass cytometry sample carrier comprising a substrate, and a capacity enhancement layer attached to the surface of the substrate. The invention also provides a mass cytometry sample carrier comprising a substrate, an anti-fouling layer (e.g. SAM) attached to the substrate and a capacity enhancement layer (e.g. 3D polymer such as a 3D polymer brush) attached to the anti-fouling layer. The sample carriers of the invention typically comprise capture elements for binding to analytes in the sample.

Capture Elements

The capture elements are the components of the mass cytometry sample carrier that bind to molecules in the sample and immobilise those molecules to the sample carrier.

Accordingly, the invention provides mass cytometry sample carriers comprising capture elements. The invention also provides a method of making a mass cytometry sample carrier comprising performing one of the methods of making a mass cytometry sample carrier as set out below and further comprising immobilising at least one capture element to the sample carrier. Typically, multiple different types of capture element are immobilised to the sample carrier. The capture element may be covalently attached to the sample carrier substrate, e.g. via by the surface assembled monolayer and/or the 3D polymer layer (e.g. 3D brush). The capture element may be non-covalently attached to the sample carrier substrate, e.g. via by the surface assembled monolayer (SAM) and/or the 3D polymer layer (e.g. 3D brush), including wherein the capture element is physiosorbed onto either the SAM or the 3D polymer brush via hydrophobic interactions, for example. The capture elements are reacted with functionalities (i.e. reactive functional groups) on the surface assembled monolayer and/or 3D polymer layer to immobilise the capture elements, and so enable the capture elements to in turn immobilise analytes.

Types of Capture Element

The capture element can be an SBP as discussed elsewhere herein. In particular, the capture element can be a protein, optionally a monoclonal antibody, a polyclonal antibody, a bispecific antibody, a multispecific antibody, an antibody fusion protein, scFv, antibody mimetic, avidin, streptavidin, neutravidin, biotin, or a combination thereof, wherein optionally the antibody mimetic comprises a nanobody, affibody, affilin, affimer, affitin, alphabody, anticalin, avimer, DARPin, Fynomer, kunitz domain peptide, monobody, or any combination thereof, a receptor, such as a receptor-Fc fusion, a ligand, such as a ligand-Fc fusion, a lectin, for example an agglutinin such as wheat germ agglutinin, a peptide, optionally a linear peptide, or a cyclical peptide, such as a bicyclic peptide, for example phalloidin, or a nucleic acid, optionally a polynucleotide or oligonucleotide, such as, DNA, RNA, and cDNA, including polynucleotide analogs such as, but not limited to xeno nucleic acid (XNA), bridged nucleic acid (BNA), glycol nucleic acid (GNA), peptide nucleic acids (PNAs), yPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. Lipopolysaccharides, steroids, eicosanoids and hormone may also be used as capture elements.

The targets of the capture element can be varied. Typical molecules that can be bound include proteins, nucleic acids, sugars, hormones, metabolites and xenobiotic compounds such as pesticides. The protein can be a receptor or ligand. In some instances the target of the capture element is a cytokine (e.g. TNF-α, IL-1, IL-10, IL-12, type I interferons (IFN-α and IFN-β), IFN-γ, IL-2, IL-4, IL-5, TGF-β, IL-10, IL-3, IL-6, IL-17, IL-21, IL-23, IL-25, IL-31, IL-35) or chemokine. By measuring the signalling molecules in a cell culture, additional information can be gained at the time of analysing the cells themselves.

Where the mass cytometry sample carrier of the invention is also required to immobilise cells as well as analytes from solution, then the mass cytometry sample carrier may comprise a capture element which binds to a cell surface protein characteristic of the cell type desired to be analysed.

The mass cytometry sample carrier of the invention is perfectly suited to the multiplexed analysis of samples. Accordingly, in some embodiments the mass cytometry sample carrier comprises two or more different capture elements (here, different capture elements referring for instance to two or more antibodies each binding to a different target). Accordingly, the invention also provides a mass cytometry sample carrier comprising at least 3, at least 4, at least 5, at least 6, at least 7, at least 8, at least 9, at least 10, at least 20, at least 30, at least 40, at least 50, or at least 100 different kinds of capture elements. The capture elements can include (i) proteins; (ii) nucleic acids; (iii) nucleic acids and proteins; (iv) antibodies; (v) nucleic acids and antibodies; (vi) antibodies and lectins; (vii) nucleic acids, lectins and antibodies; (viii) peptides; (ix) nucleic acids and peptides; (x) peptides and antibodies; (xi) peptides, nucleic acids and antibodies; (xii) peptides, antibodies and lectins; (xiii) nucleic acids, lectins and antibodies; and/or (xiv) peptides, nucleic acids, lectins and antibodies. Accordingly, in some embodiments, the invention provides a mass cytometry sample carrier which is capable of binding proteins. In some embodiments, the mass cytometry sample carrier is capable of binding nucleic acids. In some embodiments, the mass cytometry sample carrier is capable of binding carbohydrates. In some embodiments, the mass cytometry sample carrier is capable of binding cells. In some embodiments, the mass cytometry sample carrier is capable of binding proteins and nucleic acids. In some embodiments, the mass cytometry sample carrier is capable of binding proteins and cells. In some embodiments, the mass cytometry sample carrier is capable of binding proteins, nucleic acids and cells. In some embodiments, the mass cytometry sample carrier is capable of binding proteins, nucleic acids and carbohydrates. In some embodiments, the mass cytometry sample carrier is capable of binding proteins, nucleic acids, cells and carbohydrates.

In instances where both analytes and cells are desired to be captured they may be captured in discrete regions of the mass cytometry sample carrier, to improve the quality of information provided by the analysis, wherein the contents of the cells can be analysed discretely from the molecules e.g. in the extracellular environment.

In some embodiments, the mass cytometry sample carrier comprises 2 or more, such as 5 or more, 10 or more, 25 or more, 50 or more, 100 or more, 500 or more, 1000 or more or 5000 or more discrete regions. In some instances, different discrete regions may be modified in a different manner. In some instances, multiple discrete regions of the same mass cytometry sample carrier may contain the same surface modifications (i.e. include the same capture element(s)), so allowing multiple samples to be run on the mass cytometry sample carrier, and/or for repeats readings to be taken from the same sample on a single mass cytometry sample carrier). Different discrete regions may each contain just a single type of capture element for binding a specific analyte, however to do so would fail to take advantage of the capacity for multiplexing provided by IMC. Typically, at least 2, such as 5 or more, 10 or more, 25 or more, 50 or more or 100 or more different types of capture element will be present on a mass cytometry sample carrier that comprises discrete regions.

Where the mass cytometry sample carrier comprises discrete regions, one or more of the discrete regions can each comprise at least 2, at least 3, at least 4, at least 5, at least 6, at least 7, at least 8, at least 9, at least 10, at least 20, at least 30, at least 40, at least 50, or at least 100 different kinds of capture elements.

Sample Material

The invention enables the immobilisation of analytes in solution and their quantitation by mass cytometry. The range of molecules that can be analysed in the sample is therefore limited only by the availability of capture reagents that can bind to the target.

Accordingly, the sample may comprise a cell, a population of cells, a protein solution, a peptide solution, a nucleic acid solution, and carbohydrate solution, a solution comprising multiple macromolecule types, for example a solution of proteins and nucleic acids and a solution of proteins, nucleic acids and carbohydrates, and a solution comprising multiple macromolecule types and cells, for example a solution of proteins, nucleic acids and cells, and a solution of proteins, nucleic acids, carbohydrates and cells. Thus, the sample may be a tissue homogenate, tissue fluid, bodily fluid, ascites, lung fluid, spinal fluid, amniotic fluid, bone marrow aspirate, blood plasma, blood serum, exudate, faeces, urine, cell lysate, cell culture supernatant, extracellular fluid, bacterial lysate, viral supernatant, any combination thereof or other biological fluids.

In some instances, the sample comprises a pesticide that can be detected by an antibody, such as simazine, triazine, cyanazine, 2,6-dichlorbenzamide (BAM), hydroxytriazine or ecoprop.

Dual Mode Analysis

As noted above, in some embodiments, cells from a sample may also be immobilised on the mass cytometry sample carrier, optionally at the same time as analytes are absorbed from the solution phase of the cell suspension. Sometimes, the cells can be immobilised to different discrete regions on the mass cytometry sample carrier from the analytes from solution immobilised to the mass cytometry sample carrier. As will be appreciated by one of skill in the art. The capture element which immobilises cells will typically bind to a cell surface protein characteristic of the cell type desired to be analysed. If the cell-containing sample contains a variety of cell types, then each cell type of interest may be localised to a specific discrete region by the use of different capture element specifics for unique cell surface markers of the cell types desired to be analysed. Choice of particular capture elements to immobilise specific cell types is routine for one of skill in the art.

Accordingly, in some embodiments, the immobilised sample analysed in the method of the invention includes cells and the analytes from the intercellular milieu, such as cells and the analytes from the cell culture medium. As noted below, these cells and analytes may be immobilised to different discrete regions on a mass cytometry sample carrier. However, where the mass cytometry sample carriers are particulate and a solution phase analysis is performed, one or more sets of particles may be used to immobilise one or more analytes and another set of particles can be used to immobilise cells.

Additional Sample Preparation Steps

In some instances, prior to immobilisation of sample analytes to the mass cytometry sample carrier, the method may comprise the step of enriching the sample for at least one analyte of interest, such as by separating the sample into fractions using a separation process and selecting fractions comprising the analyte(s) of interest. The separation process may encompass just one separation technique, or it may comprise two or more separation techniques. Preferably, when more than one separation technique is used, the separation techniques are orthogonal, so that the components in the fractions separated from the first process are then further separated and subdivided (i.e. resolved) by the second and/or further techniques.

Mass Cytometry Sample Carriers of the Invention

The inventors noted that when performing the quantitation method of the method as outlined above, spotting a drop of liquid onto a glass slide resulted in the spread of that liquid across the surface of the slide. The diameter of the resultant spot was relatively large compared to the volume dispensed onto the slide, because of the relative hydrophilicity of the glass slide surface. The consequences of a large diameter per spot are multifold. First, for instance, the larger the spot size to which a liquid expands, the fewer spots can be arranged without overlap on an area of defined size. Furthermore, because the liquid spreads over a larger area, the analytes in solution in that spot will also be spread over a larger area, and so present at a lower level per unit area than if the drop did not spread out. Consequently, when ablating the analytes from the surface following evaporation of the solvent, a larger laser spot size is needed in order to obtain a reliable average reading of the analyte level. Ablation with a larger laser spot size can be disadvantageous if it causes fragmentation of the material being ablated from the sample, which is then thrown into neighbouring areas of the sample, causing contamination. Alternatively, multiple laser shorts can be fired in a rastering pattern across the deposited analyte, with a cumulative ion count tallied across the spot. Firing multiple laser shots however can slow down the speed of analysis vis-à-vis the time taken for a single shot.

Thus, the physical and chemical characteristics of the interaction between the analytes being immobilised from solution and the substrate are key determinants in the performance of the method. In particular, spot morphology has a great impact on the signal, as nonhomogeneous spots, such as doughnut-shape spots or coffee ring effects may cause errors in the acquisition and measurement of signals, thus affecting the reliability of the assay.

On this basis, to improve further their quantitation method, the inventors developed ways of increasing the concentration of analyte per unit area on the mass cytometry sample carrier and in doing so improving the uniformity of the analyte concentration across the spot, as well as ways of increasing signal to noise ratio. In simple terms, this has been achieved by generating a structure on the mass cytometry sample carrier to which analytes in the sample bind, via capture elements on the mass cytometry sample carrier. Thus, rather than what is likely to be a monolayer, or at the most a thin layer of non-specifically adsorbed analyte on a blank mass cytometry sample carrier, the mass cytometry sample carriers provided by the invention permits a high load of analyte per area of footprint on the mass cytometry sample carrier and/or high signal-to-noise ratio.

An alternative strategy is to control the wettability of the surface, so as to limit the spreading out of a drop of the sample by controlling the hydrophobicity of the surface; a drop of aqueous solution will spread out over a much smaller area if the surface is hydrophobic versus hydrophilic. This approach can have drawbacks, however, in that particular care will need to be taken to prevent disturbance of the drops of sample material on the mass cytometry sample carrier between deposition of the drops and the drying of the material. While this set up may be applied in certain instances as understood by one of skill in the art, it does not provide the capacity to more simply immobilise sample material to the mass cytometry sample carrier, nor as discussed in more detail below, to specifically immobilise components from the sample material.

In optimising the planar mass cytometry sample carriers, the inventors made the further inventive development that the same techniques for modifying the surface of planar mass cytometry sample carriers could be applied to particulate mass cytometry sample carriers (e.g. bead mass cytometry sample carriers or nanoparticle mass cytometry sampler carriers) when used in mass cytometry. In brief summary, mass cytometry sample carriers of the invention as described herein can be broadly described as comprising two components: a substrate and a surface modification. The surface modification is to the surface of the substrate of the mass cytometry sample carrier.

Sample Carrier Substrates

The mass cytometry sample carrier substrate can be any solid phase that can be modified as discussed herein. Examples include glass, silica, aluminium, cellulose, chitosan, Indium Tin Oxide (ITO), Aluminium oxide ($Al_2O_3$), Magnetite ($Fe_3O_4$), $CuO_x$, Hematite ($c-Fe_2O_3$), Manganese spiral Ferrite ($MnFe_2O_4$), Magnesium hydroxide ($Mg(OH)_2$), Zinc oxide (ZnO), zirconium phosphonate, halloysite, montmorillonite, steel, sapphire, Cadmium selenide (CdSe), Cadmium sulphide (CdS), Gallium Arsenide (GaAs), mica, carbon black, diamond, single walled carbon nanotubes, multiwalled carbon nanotubes, graphene, plastic, polystyrene, poly(ethyleneterephthalate), polyaniline, poly (cyclopentadiene), polystyrene, poly(vinyl chloride), poly (vinylidene fluoride), nylon, poly(divinylbenzene), poly(tetrafluoroethylene), poly(dimethylsiloxane), poly (methylmethacrylate), polyimide, polyurethane, polypropylene and encompass planar surfaces in the form, e.g., of microscope slides, as well as particulate mass cytometry sample carriers (such as beads and nanoparticles). Indeed, any object that can be covered in a thin sticky film, to which can be attached capture elements, an SAM and/or 3D polymer (to which capture elements may be attached) can function as a mass cytometry sample carrier (e.g. metal, glass or wood). Furthermore, any planar surface that can be coated in polydopamine, to which can be attached capture elements, an SAM and/or a 3D polymer (to which capture elements may be attached) can function as an imaging mass cytometry sample carrier.

As discussed below in more detail, one benefit of polydopamine modification is its flexibility in working with multiple planar surfaces. It is also useful in attaching to a variety of capture elements through —SH and —$NH_2$ chemistries. This flexibility is useful specifically in highly multiplexed assays enabled by imaging mass cytometry and kits for use in such assays.

Where the mass cytometry sample carrier substrate is particulate (e.g. a bead or nanoparticle), the bead may be doped so as to contain more or more labelling atoms or the nanoparticle may contain one or more labelling atoms (labelling atoms are discussed in more detail below herein, at page 62). Here, the labelling atoms act as an elemental coding for the particle, such that when the particle is analyzed during mass cytometry, a signal from the labelling atoms will be detected, identifying the particle. Different particles may comprise different elemental codings, made up of different labelling atoms/isotopes, different combinations of labelling atoms/isotopes and even different ratios thereof. Accordingly, in some embodiments, all labelling atoms in an element coded particle are of the same atomic mass. Alternatively, element coded particle can comprise labelling atoms of differing atomic mass. Accordingly, in some instances, a set of particles may be formed from particles each of which comprises just a single type of labelling atom. Alternatively, in some instances, a set of particles may be formed from particles each of which comprises a mixture of labelling atoms. In some instances, a set of particles may be formed from particles comprise a mix of those with single labelling atom elemental coding and mixes of labelling atoms as elemental codings. Sets of particles find particular application in the methods detailed herein.

Winnink, M. A., et. al., *J. Am. Chem. Soc.,* 2009, 131, 15276 discloses a methodology for the preparation of coded nanoparticles. Said nanoparticles comprise —COOH groups such that species (e.g. polymerisation initiators, biomolecules) can be bound to the surface of the particle through a coupling reaction with the carbodiimide chemistry, as discussed herein.

Where the mass cytometry sample carrier is planar, then it may be optically transparent, for example made of glass or plastic. Where the mass cytometry sample carrier is optically transparent, it enables ablation of the sample material through the support. For example, the solid support may include a tissue slide. Through-carrier ablation is discussed for example in WO2014169394. Planar mass cytometry sample carriers may also contain elemental coding in the substrate.

The mass cytometry sample carrier substrates can be modified in a number of ways, as described below. As will be appreciated by one of skill in the art, only certain specific modifications are effective with certain specific substrates. For instance, it will be apparent to those skilled in the art that Piranha solution ($H_2O_2$ and $H_2SO_4$) should not be applied to organic substrates, but should be limited to cleaning (and thus providing hydroxyl moieties) on the surfaces of glass, siloxanes, and metals, etc. However, those skilled in the art will appreciate that the surface modifications that rely on the presence of surface-bound hydroxyl groups, as discussed herein, can also be applied to those organic substrates comprising said hydroxyl moieties (e.g. polyethylene glycol, etc).

Mass Cytometry Sample Carriers Comprising a Surface Assembled Monolayer/Anti-Fouling Layer The anti-fouling layer acts to prevent inappropriate (i.e. non-specific) adhesion of molecules to the mass cytometry sample carrier. An anti-fouling layer therefore reduces the non-specific adsorption of biomolecules to a mass cytometry sample carrier comprising the layer versus a mass cytometry sample carrier composed of an unmodified mass cytometry sample carrier substrate. A typical glass or plastic mass cytometry sample carrier has numerous reactive groups on its surface which can interact with analytes. Accordingly, by reacting those groups to reduce their number in turn will reduce adhesion of biological material (be that biological macromolecules or cells) to the mass cytometry sample carrier. The anti-fouling layer can be a surface assembled monolayer. Example anti-fouling layers include a silane layer, an epoxide layer, a fluoride terminated monolayer, and an alkylthiol layer (the alkylthiol layer can form a self-assembled monolayer on gold surfaces or gold nanoparticles). In particular, the non-fouling layer can be generated by reacting free hydroxyl groups on the surface of a glass slide with a trimethoxysilane. Accordingly, the invention provides a mass cytometry sample carrier comprising a silane self-assembled monolayer, which can be used in the methods described herein. Silanes that provide a range of functionalities are commercially available. For instance, Shinetsu Silicone (Japan) provides trimethoxysilanes with vinyl, epoxy, styryl, methacryloxy, acryloxy, amino, ureide, isocyanate, isocyanurate and mercapto functionalities. The invention also provides a mass cytometry sample carrier comprising an epoxysilane self-assembled monolayer, which can be used in the methods described herein. Accordingly, the invention provides a mass cytometry sample carrier comprising a fluoride-terminated self-assembled monolayer, which can be used in the methods described herein. Accordingly, the invention provides a mass cytometry sample carrier comprising an alkylthiol self-assembled monolayer, which can be used in the methods described herein.

Alternatively, a non-fouling layer can be generated by the creation of a dense polymer layer on the surface of the mass cytometry sample carrier, by polymerising from functionalities on the surface of the mass cytometry sample carrier substrate. In some instances, an alkyl bromide terminated layer is used. Accordingly, the invention provides a mass cytometry sample carrier comprising an alkyl bromide terminated self-assembled monolayer (e.g. formed from reaction of the surface of the mass cytometry sample carrier with W-mercaptoundecyl bromoisobutyrate), which can be used in the methods described herein.

Thus the non-fouling layer reduces the non-specific adsorption of molecules to the mass cytometry sample carrier, and thereby enhances the signal to noise ratio of target analytes immobilised to the mass cytometry sample carrier through the capture element(s).

Accordingly, the invention also provides a method of making a mass cytometry sample carrier comprising:
  i. providing a substrate; and
  ii. functionalising the substrate by attaching a surface assembled monolayer to the surface of the substrate.

In some embodiments, the method further comprises, prior to step (ii), cleaning the surface of the substrate, such as by treatment with $H_2SO_4$ and $H_2O_2$ when the substrate is a glass, silicon, or siloxane substrate.

Accordingly, in some embodiments, the invention provides a method of making a mass cytometry sample carrier comprising:
  i. providing a substrate; and
  ii. functionalising the substrate by attaching a surface assembled monolayer to the surface of the substrate, wherein the surface assembled monolayer comprises at least one functional group capable of initiating a controlled radical polymerisation.

In some embodiments, the method of making a mass cytometry sample carrier further comprises step (iii) of controlling the number of groups capable of initiating a controlled radical polymerisation present on the SAM. Sometimes, the step of controlling the number of groups capable of initiating a controlled radical polymerisation present on the SAM comprises increasing the number of groups capable of initiating a controlled radical polymerisation present on the SAM (for instance by using an iniferter in the polymerisation). Other times, the step of controlling the number of groups capable of initiating a controlled radical polymerisation present on the SAM comprises decreasing the number of groups capable of initiating a controlled radical polymerisation present on the SAM (for example by substituting bromide chain terminating groups for azide groups). In some embodiments, the method further comprises, prior to step (ii), cleaning the surface of the substrate, such as by treatment with $H_2SO_4$ and $H_2O_2$ when the substrate is a glass, silicon, or siloxane substrate.

In some embodiments, as described below in more detail, the methods set out above further comprise linking a polymer layer to the surface assembled monolayer. For instance, the method may comprise linking a polymer layer to the substrate by polymerising from the SAM to form a polymer (e.g. by ATRP, RAFT, nitroxide mediated polymerisation, single-electron transfer living radical polymerisation, or PIMP). In some embodiments, the polymer layer may be linked by a process of grafting the polymer to the SAM.

Capacity Enhancing Polymer Layers

The signal to noise ratio can be improved (alternatively or additionally to the use of a non-fouling layer) by increasing the amount of analyte specifically immobilised to the mass cytometry sample carrier. While this can be achieved in principle by increasing the density of the capture element on the 2D surface of the mass cytometry sample carrier, excessively high concentrations of capture element(s) can in itself promote non-specific interactions with analytes in solution and so reduce the difference between signal and noise, even if the mass cytometry sample carrier includes a non-fouling layer to which the high density of capture element is attached.

Accordingly, generating a polymer layer which extends outwards from the surface of the provides greater capacity for the attachment of capture elements, thereby increasing the capacity of the mass cytometry sample carrier but without such a risk of promoting non-specific association as for a 2D surface highly densely coated with capture elements. Accordingly, in some embodiments, the mass cytometry sample carrier comprises a polymer layer, in particular a 3D polymer layer.

The 3D polymer layer may be attached directly to the mass cytometry sample carrier substrate. In other instances, the 3D polymer layer is attached to the non-fouling layer/ surface assembled monolayer which is attached to the mass cytometry sample carrier substrate. In other instances, the 3D polymer layer is attached to a polydopamine layer as discussed below.

The 3D polymer layer can be generated by a variety of processes. The polymer (generated by in situ polymerisation or synthesised elsewhere and then attached to the substrate; "grafting-to") comprises functionalities which can then, directly or via linkers, be attached to capture elements that bind to analytes in the sample.

The functionalities that can be provided on the 3D polymer include amines, amides, esters, carboxyls, thiols, cyclic imides, peroxides, maleimides, aldehydes, epoxides, carbodiimides, succinimidyl esters, such as an N-hydroxysuccinimide ester, azides, tetrazines, isothiocyanates, a strained cyclo-alkyne (such as dibenzocyclooctyne (DBCO), monofluorinated cyclooctyne (MOFO), difluorocyclooctyne (DIFO), dimethoxyazacyclooctyne (DIMAC), dibenzocyclooctyne (DIBO), dibenzoazacyclooctyne (DIBAC), biarylazacyclooctynone (BARAC), bicyclononyne (BCN), 2,3,6,7-tetramethoxy-DIBO (TMDIBO), sulfonylated DIBO (S-DIBO), carboxymethylmonobenzocyclooctyne (COMBO), pyrrolocyclooctyne (PYRROC)) and strained alkene (such as trans-cyclooctene, trans-bicyclo[6.1.0]nonene and derivatives therefore, methylcyclopropene, bicyclo [6.1.0]nonyne, cyclooctyne and norbornene). By including a variety of different functionalities in the polymer, e.g. by use of subunits comprising different functionalities, different capture elements can then be attached to the same 3D polymer, using orthogonal reaction chemistries known in the art for conjugation of biomolecules.

In some embodiments, the 3D polymer is a 3D polymer brush. The brushes in the 3D polymer can project away from the surface of the mass cytometry sample carrier. In some embodiments, the polymer brush projects vertically away from the surface of the mass cytometry sample carrier, such as perpendicularly away from the surface of the sample.

The 3D polymer brush can be generated by a variety of processes. The polymer (generated in situ—"grafting from"- or synthesised elsewhere and then attached to the substrate "grafting to") comprises functionalities as discussed above which can then, directly or via linkers, be attached to capture elements, which bind to molecules in the sample.

A non-exhaustive list of three different types of 3D polymers that can be used in the mass cytometry sample carriers of the invention is presented below.

In certain aspects, a polymer such as poly-L-lysine, PEG (polyethylene glycol), PEG MEA (methyl ether acrylate), PVMS (polyvinylmethyl siloxane), polystyrene or another polymer known in the art may be used to functionalize a planar surface for production of a sample carrier described herein. The polymer may present carboxyl groups, amine groups, thiol groups, or may be amine or thiol reactive. The polymer may be modified to provide a click chemistry group.

In certain aspects, the monomer used for polymerization may be incubated at a concentration at or below 0.1 mg/ml, 0.25 mg/ml, 0.5 mg/ml, 0.75 mg/ml, 1 mg/ml, 1.25 mg/ml, 1.5 mg/ml, 2 mg/ml, 3 mg/ml, or 5 mg/ml. For example, the concentration may be at or between 0.1 mg/ml and 0.25 mg/ml, 0.1 mg/ml and 0.5 mg/ml, 0.1 mg/ml and 0.75 mg/ml, 0.1 mg/ml and 1 mg/ml, 0.1 mg/ml and 1.25 mg/ml, 0.1 mg/ml and 1.5 mg/ml, 0.1 mg/ml and 2 mg/ml, 0.1 mg/ml and 3 mg/ml, 0.1 mg/ml and 5 mg/ml, 0.25 mg/ml and 0.5 mg/ml, 0.25 mg/ml and 0.75 mg/ml, 0.25 mg/ml and 1 mg/ml, 0.25 mg/ml and 1.25 mg/ml, 0.25 mg/ml and 1.5 mg/ml, 0.25 mg/ml and 2 mg/ml, 0.25 mg/ml and 3 mg/ml, 0.25 mg/ml and 5 mg/ml, 0.5 mg/ml and 0.75 mg/m, 0.5 mg/ml and 1 mg/ml, 0.5 mg/ml and 1.25 mg/ml, 0.5 mg/ml and 1.5 mg/ml, 0.5 mg/ml and 2 mg/ml, 0.5 mg/ml and 3 mg/ml, 0.5 mg/ml and 5 mg/ml, 0.75 mg/ml and 1 mg/ml, 0.75 mg/ml and 1.25 mg/ml, 0.75 mg/ml and 1.5 mg/ml, 0.75 mg/ml and 2 mg/ml, 0.75 mg/ml and 3 mg/ml, 0.75 mg/ml and 5 mg/ml, 1 mg/ml and 1.25 mg/ml, 1 mg/ml and 1.5 mg/ml, 1 mg/ml and 2 mg/ml, 1 mg/ml and 3 mg/ml, 1 mg/ml and 5 mg/ml, 1.25 mg/ml and 1.5 mg/ml, 1.25 mg/ml and 2 mg/ml, 1.25 mg/ml and 3 mg/ml, 1.25 mg/ml and 5 mg/ml, 1.5 mg/ml and 2 mg/ml, 1.5 mg/ml and 3 mg/ml, 1.5 mg/ml and 5 mg/ml, 2 mg/ml and 3 mg/ml, 2 mg/ml and 5 mg/ml, or 3 mg/ml and 5 mg/ml. The polymerization may be performed at around 4 degrees Celsius, 25 degrees Celsius (or around room temp), around 37 degrees Celsius, between about 4 degrees and 25 degrees Celsius, between about 4 degrees Celsius and 37 degrees Celsius, or between about 25 degrees Celsius and 37 degrees Celsius. The incubation for polymerization may be performed in 24 hours or less, 12 hours or less, 6 hours or less, 3 hours or less, 2 hours or less, 1 hour or less. For example, the incubation may be performed at or between 1 and 24 hours, 1 and 12 hours, 1 and 6 hours, 1 and 3 hours, 1 and 2 hours, 2 and 24 hours, 2 and 12 hours, 2 and 6 hours, 2 and 3 hours, 3 and 24 hours, 3 and 12 hours, 3 and 6 hours, 6 and 24 hours, 6 and 12 hours, or 12 and 24 hours. In cases where a monolayer is desired, the monomer concentration, temperature and/or incubation time may be on the lower end. Alternatively, for maximal functionalization across a surface, a higher monomer concentration, temperature and/or incubation time may be used.

b. Acrylate-Based 3D Polymer Brushes

In some instances, the 3D polymer brush is generated by surface initiated atomic transfer radical polymerization.

For instance, in some embodiments, the 3D polymer brush comprises a polymer comprising methacrylate monomers comprising functionalities, such as glycidyl methacrylate.

In some embodiments, the 3D polymer brush comprises a co-polymer. As discussed above, the constituent monomers of the co-polymer may comprise a different functionalities for attaching capture elements through differing chemistries. Further, in some embodiments, one kind of monomer in the co-polymer may comprise a side-chain which controls the properties of the 3D polymer brush. For instance, if the monomer comprises a PEG subunit, this can be used to control the hydrophilicity of the polymer layer comprising the polymer brushes. Likewise, the length of any alkyl sidechain on a (functionalised or non-functionalised) monomer can be used to control hydrophobicity. The side changes can also be used to control the density of the polymer chains that form the 3D polymer brush.

In some instances, the 3D polymer brush comprises a polymer selected from the group comprising a glycidyl methacrylate (GMA) co-polymer, glycidyl methacrylate (GMA)-hydroxy ethyl methacrylate (HEMA) copolymer (poly(GMA-co-HEMA)), a glycidyl methacrylate-co-poly(ethylene glycol) methacrylate copolymer (poly (GMA-co-PEGMA)), a poly(oligo(ethylene glycol) methyl ether methacrylate) (POEGMA); and a methacryloyloxyethyl phosphorylcholine (MPC) co-polymer. In some instances, the polymer comprises poly[2-(methacryloyloxy)ethyl dimethyl-(3-sulfopropyl)ammonium hydroxide] or another zwitterionic polymer described below.

Other non-limiting examples of the 3D polymer brushes suitable for use in the present invention include when the polymer is a neutral species such as polystyrene, poly(methyl methacrylate (PMMA), poly(N-isopropylacrylamide) (PNIPAM), poly(oligo(ethylene glycol) methacrylate) (POEGMA), or poly(bis(ethylene glycol) methyl ether methacrylate) (PDEGMA).

Furthermore, stimuli-responsive polymer brushes may be used in the present invention, including polymer brushes sensitive to changes in pH such as poly(acrylic acid) (PAA), poly(methacrylic acid) (PMAA), poly((dimethylamino) ethyl methacrylate) (PDMAEMA), poly((diethylamino) ethyl methacrylate) (PDEAEMA), or poly(4-vinylpyridine) (P4VP).

Modifications to the polymer brushes for use in the present invention are also envisaged. Modifications include changing the brush density on the surface (as discussed further in the zwitterionic polymer brush section), changing the solvent, or changing the salt content of the solvent. Such modifications will impact the way the polymer brush interacts with molecules and/or cells at the interface, including species such as capture elements. The 3D polymer brush can be generated by polymerisation from free amine groups on the surface of the mass cytometry sample carrier generated by formation of an SAM using, for example, (3-aminopropyl)triethoxysilane (APTES) on a glass substrate (e.g. one that has been previously cleaned with a mixture of sulfuric acid ($H_2SO_4$) and hydrogen peroxide ($H_2O_2$), used to clean organic residues off substrates).

Accordingly, in some embodiments, the mass cytometry sample carrier comprises a silane SAM and a 3D polymer brush. In some instances, the 3D polymer brush comprises a methacrylate-based polymer, such as a co-polymer. In some instances, the mass cytometry sample carrier comprises a silane SAM and a 3D polymer brush, wherein at least some subunits of the 3D polymer brush comprise an amine, amide, ester, carboxyl, thiol, cyclic imide, peroxide, maleimide, aldehyde, epoxide, carbodiimide, succinimidyl ester, azide, tetrazine, isothiocyanate, dibenzocyclooctyne (DBCO), and/or trans-cyclooctene (TCO) functionality, such as at least some glycidyl methacrylate subunits. The functionalities can be used to attach capture elements. Accordingly, in some embodiments, the mass cytometry sample carrier further comprises one or more capture elements.

Production of such mass cytometry sample carriers can be achieved using standard techniques in the art. 3D polymer-brush substrates can be prepared from GMA-co-PEGMA or GMA-co-HEMA polymers by Surface-Initiated Atom Transfer Radical Polymerization (SI-ATRP) on glass surfaces. For binding of polymers, a glass substrate is cleaned and silanized using (3-aminopropyl)triethoxysilane (APTES), to which poly[glycidyl methacrylate-co-poly(ethylene glycol) methacrylate] (GMA-co-PEGMA) or poly (glycidyl methacrylate-co-2-hyroxyethyl methacrylate) (GMA-co-HEMA) polymer brushes are synthesized using SI-TRP on a glass surface. Substrates with this kind of architecture exhibit higher immobilization capacities for protein binding, which resulted in high sensitivity for protein detection as compared to 2D counterparts. Protocols for the synthesis of such brushes are available for example in Liu et al., 2011 (Journal of colloid and interface science, 360:593) for GMA-co-PEGMA polymer brush preparation and Lei et al., 2016 (ACS applied materials & interfaces, 8:10174).

Accordingly, in some embodiments, the invention provides a method of producing a mass cytometry sample carrier comprising reacting a substrate with a first reagent to produce a SAM-coated substrate (e.g. as described in the preceding section), and reacting the SAM-coated substrate with monomer subunits to produce a mass cytometry sample carrier comprising a 3D polymer, such as a 3D polymer brush. In some instance the polymer is selected from the group comprising a glycidyl methacrylate (GMA) co-polymer, glycidyl methacrylate (GMA)-hydroxy ethyl methacrylate (HEMA) copolymer (poly(GMA-co-HEMA)), a glycidyl methacrylate-co-poly(ethylene glycol) methacrylate copolymer (poly (GMA-co-PEGMA)), a poly(oligo(ethylene glycol) methyl ether methacrylate) (POEGMA); and a methacryloyloxyethyl phosphorylcholine (MPC) co-polymer. In some embodiments, the SAM is prepared by reaction of a glass substrate with APTES, and the monomer subunits are polymerised by surface-initiated atom transfer radical polymerisation (SI-ATRP), such as wherein the polymerisation is of acrylate-based monomers, such as methacrylate based monomers. In some embodiments, the method further comprises attaching one or more capture elements to the polymer, for instance by reaction of the epoxy group when the polymer has been synthesised from glycidyl methacrylate or a mix of monomers comprising glycidyl methacrylate. The range of capture elements that can be attached to the polymer is discussed herein in the section at page 9.

c. Zwitterionic Polymer Brushes

The invention also provides mass cytometry sample carriers in which the 3D polymer brush comprises a zwitterionic polymer.

Exemplary zwitterionic polymer brushes in the mass cytometry sample carriers of the invention include those comprising a polybetaine, such as selected from the group consisting of poly(carboxybetaines), poly(sulfobetainemethacrylate), poly(sulfobetaineacrylamide), a methacryloyloxyethyl phosphorylcholine (MPC) polymer or co-polymer, and poly[2-(methacryloyloxy)ethyl dimethyl-(3-sulfopropyl)ammonium hydroxide].

The 3D polymer (e.g. 3D polymer brush) can be generated by polymerisation from an alkyl bromide terminated self-assembled monolayer (e.g. by reaction of a glass surface with ω-mercaptoundecyl bromoisobutyrate), for instance using a carboxybetaine methacrylate monomer in an SI-ATRP reaction.

It is possible to control the density of the polymer grown from the SAM by controlling the number of initiator terminators on the SAM before the polymerisation of the zwitterionic monomer. For instance, for the SAM discussed above which results in an alkyl bromide terminator, the bromine can be substituted for an azide. The proportion of bromines substituted for azides then determines the density of the brushes of the zwitterionic polymer, because the polymerisation reaction only proceeds from the alkyl bromide terminated SAMs. Polymerization can also be controlled by other methods known in the art, such as surface initiated reversible attrition-fragmentation chain transfer (RAFT) polymerization.

It is possible to perform the azide substitution of end groups during the polymerisation process. For instance, polymerisation can be allowed to occur from all groups' initiators for a first phase of the polymerisation, followed by azide termination of some of the chains. Following this, a second polymerisation stage can be initiated, in which the fewer active chains extend further. This process in particular allows the development of a first denser polymer layer and a second more disperse layer. The first layer can function to prevent non-specific adhesion of molecules to the mass cytometry sample carrier, and the second layer can function as the site of attachment for capture elements.

Reducing the number of alkyl bromide terminated SAMs by substitution for azide was noted to increase the depth of the 3D polymer brush layer in Huang et al., 2012 (Adv. Mater. 24:1834). This was proposed to be due to rapid bimolecular termination at high initiator densities. Substitution with azide groups was achieved by incubation in aqueous azide solution, with time and concentration variable to control the degree of replacement of bromide with azide.

In an alternative method for generating the 3D polymer brush with different density levels, the first layer can be generated using surface initiated photoiniferter-mediated polymerization (SI-PIMP). A first polymer layer can be prepared by polymerising carboxybetaine monomer in methanol in the presence of tetraethylthiuram disulfide (TED), which prevents excess chain termination due to chain-chain radical recombination. Following this, a second polymerisation step was performed in the absence of TED, in 90% water/methanol.

Accordingly, in some embodiments, the mass cytometry sample carrier comprises a SAM formed from reaction of an alkyl bromide with the mass cytometry sample carrier substrate and a 3D polymer brush. In some instances, the 3D polymer brush comprises a methacrylate-based polymer, such as a co-polymer, wherein the 3D polymer brush comprises a zwitterionic polymer. In some instances, the mass cytometry sample carrier comprises a SAM and a 3D polymer brush comprising a zwitterionic polymer, wherein at least some subunits of the 3D polymer brush comprise an amine, amide, ester, carboxyl, thiol, cyclic imide, peroxide, maleimide, aldehyde, epoxide, carbodiimide, succinimidyl ester, azide, tetrazine, isothiocyanate, dibenzocyclooctyne (DBCO), and/or trans-cyclooctene (TCO) functionality. The functionalities can be used to attach capture elements. Accordingly, in some embodiments, the mass cytometry sample carrier further comprises one or more capture elements. In some instances, the 3D polymer brush has been produced by SI-ATRP or SI-PIMP.

Accordingly, in some embodiments, the invention provides a method of making a mass cytometry sample carrier comprising:
(i) providing a substrate;
(ii) functionalising the substrate by attaching a surface assembled monolayer to the surface of the substrate, wherein the surface assembled monolayer comprises at least one functional group capable of initiating a controlled radical polymerisation; and
(iii) controlling the number of groups capable of initiating a controlled radical polymerisation present on the SAM; such as:
  a. controlling the number of groups capable of initiating a controlled radical polymerisation present on the SAM comprises by increasing the number of groups capable of initiating a controlled radical polymerisation present on the SAM (such as by adding an iniferter to the polymerisation reaction); or
  b. controlling the number of groups capable of initiating a controlled radical polymerisation present on the SAM comprises by decreasing the number of groups capable of initiating a controlled radical polymerisation present on the SAM (such as substituting some of the bromines on an alkyl bromide terminated SAM for azide).

Accordingly, in some embodiments, the invention provides a method of making a mass cytometry sample carrier comprising:
(i) providing a substrate;
(ii) functionalising the substrate by attaching a surface assembled monolayer to the surface of the substrate, wherein the surface assembled monolayer comprises at least one functional group capable of initiating a controlled radical polymerisation;
(iii) performing a first polymerisation reaction, initiated by functional groups on the SAM, and
(iv) controlling the number of groups from the first polymer layer capable of initiating a second controlled radical polymerisation present; such as wherein:
  a. controlling the number of groups capable of initiating a controlled radical polymerisation present on the first polymer layer comprises by increasing the number of groups capable of initiating a controlled radical polymerisation present on the first polymer layer (such as by adding an iniferter to the polymerisation reaction); or
  b. controlling the number of groups capable of initiating a controlled radical polymerisation present on the first polymer layer comprises by decreasing the number of groups capable of initiating a controlled radical polymerisation present on the first polymer layer (such as substituting some of the bromines on the first polymer layer for azide).

Accordingly, in some embodiments, the invention provides a method of making a mass cytometry sample carrier comprising:
(i) providing a substrate;
(ii) functionalising the substrate by attaching a surface assembled monolayer to the surface of the substrate, wherein the surface assembled monolayer comprises at least one functional group capable of initiating a controlled radical polymerisation;
(iii) performing a first polymerisation reaction, initiated by functional groups on the SAM;
(iv) controlling the number of groups from the first polymer layer capable of initiating a second controlled radical polymerisation present; such as wherein:
   a. controlling the number of groups capable of initiating a controlled radical polymerisation present on the first polymer layer comprises by increasing the number of groups capable of initiating a controlled radical polymerisation present on the first polymer layer (such as by adding an iniferter to the polymerisation reaction); or
   b. controlling the number of groups capable of initiating a controlled radical polymerisation present on the first polymer layer comprises by decreasing the number of groups capable of initiating a controlled radical polymerisation present on the first polymer layer (such as substituting some of the bromines on the first polymer layer for azide); and
(v) performing a second polymerisation reaction.

d. Polysaccharide Hydrogel

Polysaccharide hydrogels (e.g. carboxymethylated dextran (CMD), amino modified dextrans, hydrazomodified dextrans, etc.) can also be used to coat mass cytometry sample carriers, and are attractive for use in the invention due to their outstanding bio-inertness and extremely high protein immobilization capacity.

To generate a mass cytometry sample carrier comprising a carbohydrate hydrogel, typically, the carbohydrate is grafted onto the mass cytometry sample carrier. By way of example, a glass mass cytometry sample carrier substrate can be reacted with (3-aminopropyl)triethoxysilane (APTES), thereby silanizing the glass slide and introducing an amine functional group to which the carbohydrate can be attached. As noted above, this silane layer can assist in preventing non-specific adsorption of analytes and other biomolecules to the substrate, however as the silane layer also terminates in free amines, the carboxyl groups of e.g. carboxy methylated dextran (CMD) can be reacted with the amines via carbodiimide chemistry. By performing the reaction under conditions such that each carbohydrate polymer reacts with the silane layer at only a few of the carboxy groups, the polymer can be made to form molecular brushes, with the length of the brushes controlling the thickness of the polymer layer. Alternatively epoxysilane can be used, and the dextran coupled to the epoxy group. Indeed, many different functionalised silanes can be used, and by ensuring that the appropriate reaction partner to the functionality on the silane is present on the carbohydrate, the carbohydrate can be grafted to the mass cytometry sample carrier substrate. The properties of the carbohydrate layer can be controlled based on the choice of the dextran immobilised to the substrate (such as via an SAM), including the use of mixtures of dextrans of different molecular weights.

Accordingly, the invention provides a mass cytometry sample carrier comprising a substrate and a carbohydrate hydrogel attached to the substrate. In some embodiments, the carbohydrate hydrogel is selected from carboxymethylated dextrans, amino modified dextrans, hydrazomodified dextran. In some embodiments, the mass cytometry sample carrier comprises a dextran of a single molecular weight or weight range. In some embodiments, the mass cytometry sample carrier comprises dextrans of different molecular weights or weight ranges. For instances, the dextran might comprise 500 kDa dextran, 250 kDa dextran, 150 kDa dextran and/or 75 kDa dextran.

As an alternative, nitrocellulose can be used as the polymer layer for attachment of capture elements. The nitrocellulose can be grafted onto the mass cytometry sample carrier substrate via the use of a silane SAM in the same manner as described above for modified dextrans.

Alternative pre-formed polymers may be grafted onto the surface of the mass cytometry sample carrier through a reaction between a reactive end group on the pre-formed polymer (e.g. a thiol, silane, amino, or carboxy group) with a species of complementary reactivity bound to the surface of the mass cytometry sample carrier. In addition, pre-formed polymers may be grafted onto the surface of the mass cytometry sample carrier through the exposure to photoradiation of photoradical surface-bound initiators on a mass cytometry sample carrier in the presence of a polymer film.

Thus in some embodiments, the mass cytometry sample carrier comprises an amine terminated SAM and a carbohydrate hydrogel. In some embodiments, the mass cytometry sample carrier comprises an epoxy terminated SAM and a carbohydrate hydrogel. In some embodiments, the carbohydrate hydrogel comprise amine, amide, ester, carboxyl, thiol, cyclic imide, peroxide, maleimide, aldehyde, epoxide, carbodiimide, succinimidyl ester, azide, tetrazine, isothiocyanate, dibenzocyclooctyne (DBCO), and/or trans-cyclooctene (TCO) functionalities. The functionalities can be used to attach capture elements. Accordingly, in some embodiments, the mass cytometry sample carrier further comprises one or more capture elements.

The invention further provides a method of making a mass cytometry sample carrier as described above, comprising: (i) providing a mass cytometry sample carrier substrate and (ii) attaching a polysaccharide polymer layer to a substrate. Optionally, between steps (i) and (ii) the method comprises reaching the substrate with a silane to generate a functionalised SAM, wherein step (ii) the comprises attaching the polysaccharide polymer layer by reacting it with functionalities on the SAM (e.g. an amine), such as wherein the polysaccharide polymer layer is formed from dextran or a range of dextrans of different molecular weights.

Attachment of the Capture Elements to the Mass Cytometry Sample Carrier

The capture element can be attached to the mass cytometry sample carrier by a variety of techniques. At a basic level, passive immobilisation can be achieved (e.g. due to hydrophobic interactions between a polystyrene mass cytometry sample carrier and the capture element). Preferably, however, specific functionalities on the mass cytometry sample carrier, such as those provided by the SAM or the polymer (be it a 3D polymer brush or the functionalised carbohydrate hydrogel) are reacted with the capture elements.

Any reaction chemistry commonly used in molecular biology techniques can be used to attach the capture element(s). The attachment can be via a covalent link, or can be non-covalent. The reaction can be directly between a functionality on the SAM or the polymer and the capture element, or it can be mediated by a linker or other reagent—i.e. one which reacts with a first functionality leaving a second functionality in its place, optionally including a linker. By way of example, if the functional group on the mass cytometry sample carrier were a sulfhydryl, and the capture element had a free amine for conjugation, then a linker reagent with a maleimide at one end and NHS-ester at the other end could be used—e.g. reaction of the maleimide linker with the sulfhydryl (effectively replacing the sulfhydryl functionality with the NHS-ester), and then the capture element could be immobilised to the mass cytometry sample carrier (by reaction of the NHS-ester with the free amine).

Common reaction chemistries include—α or ε-amine with NHS-ester, strained alkyne with azide, strained alkene with tetrazine, strained alkyne with a nitrone, maleimide and sulfhydryl, epoxides on the mass cytometry sample carrier can be reacted with a range of functional groups on the mass cytometry sample carrier SAM or 3D polymer (with primary amines, sulfhydryls, or hydroxyl groups to create secondary amine, thioether, or ether bonds, respectively).

In some instances, the capture elements are immobilised to the mass cytometry sample carrier via a link encompassing a non-covalent interaction. For instance, the interaction between biotin and avidin, streptavidin or neutravidin may form part of the linkage. Alternatively, an anti-Fc antibody may be covalently immobilised to the mass cytometry sample carrier, and an antibody specifically binding to a target analyte in turn bound to the anti-Fc antibody. Other arrangements of covalent and non-covalent interactions would be understood and performed by the person of skill in the art as a matter of routine.

Accordingly, the invention further provides a method of manufacturing a mass cytometry sample carrier as set out herein, further comprising the step of attaching at least one capture element to the surface modification of the substrate.

Polydopamine Planar Surface Modifications

Surface modification and functionalisation of substrates as described in the preceding section is an effective method for modifying and controlling surface properties and for introducing new functionalities onto materials, and as such has become an important tool in the fields of biomaterials, tissue engineering and medical diagnostics. However, many of these methods rely on the substrate having specific surface chemistries to facilitate binding of the functionalised layer. For example, formation of SAMs of thiolates can only be performed on noble metal surfaces, whilst formation of alkylsilane SAMs can only form on surfaces such as silicon dioxide and silicon, which bear reactive hydroxyl moieties. To enable the modification of further substrates for planar mass cytometry sample carriers, the inventors have further developed a polydopamine assisted approach for introducing functionalities to planar mass cytometry sample carrier substrates.

Dopamine undergoes spontaneous facile oxidative polymerisation in alkaline solution (pH>7.5) to yield polydopamine (PDA). Although a number of oxidation agents have been employed, the polymerisation proceeds in the presence of atmospheric oxygen. Without being bound by any specific theory, polymerisation is thought to involve initial oxidation of dopamine to dopamine quinone, an intramolecular cyclisation and oxidation to dopamine-chrome, followed by rearrangement to form either 5,6-dihydroxyindole or 5,6-indolequinone (see Scheme 1 below). The products 5,6-dihydroxyindole or 5,6-indolequinon can then undergo polymerisation in-situ to form polydopamine. Attempts to characterise PDA have detected a range of different structures, including linear trimers of 5,6-hydroxyindole (I), copolymers of 5,6-hydroxyindole, 5,6-indolequinone, and dopamine quinone (II), hierarchical aggregates of oligomers, supermolecular aggregates of indole monomers (III), self-assembled trimers (IV), and structures incorporating pyrrole carboxylic acid moieties (V-1 and V-2).

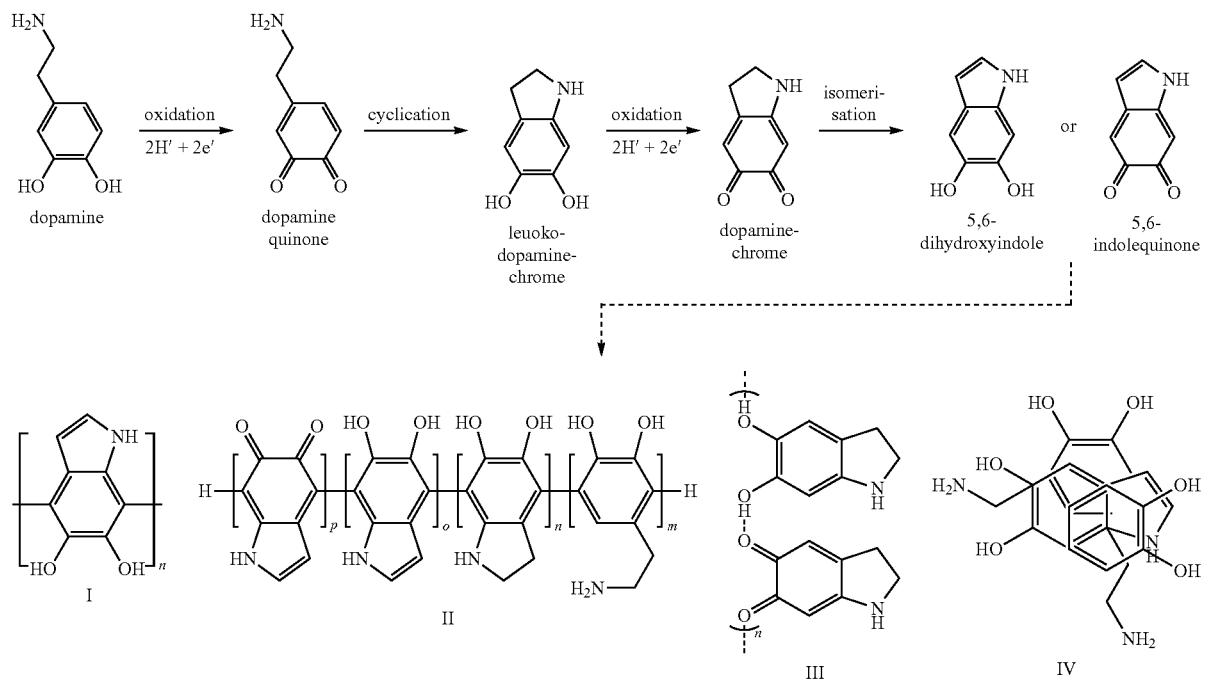

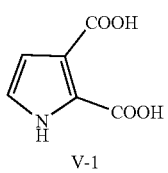
V-1

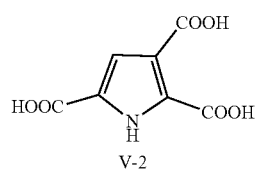
V-2

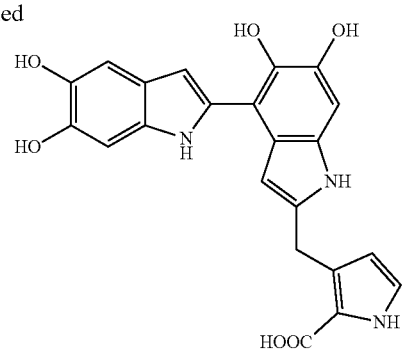
VI

Thus, the diverse range of functionalities present in PDA facilitates its effective binding to a range of substrates, including unreactive substrates and even superhydrophobic surfaces. PDA can readily form coatings on the surface of planar substrates. For example, a PDA coating can be deposited on a planar substrate by polymerising the dopamine monomer in the presence of the planar substrate. PDA surface functionalisation is unselective and can be applied to a wide variety of planar substrates, including inorganic and organic materials, metals, noble metals, metal oxides, mica, silica, ceramics and polymers.

Thus the invention provides a planar mass cytometry sample carrier (i.e. for use in imaging mass cytometry) comprising a substrate and a polydomamine (PDA) surface modification (i.e. a PDA layer).

The various functionalities introduced by the PDA can then be used to attach further components to the modified planar mass cytometry substrate, as set out above. For instance, capture elements can be reacted with functionalities of the PDA layer to immobilise the capture elements to the planar mass cytometry sample carrier, thus enabling the planar mass cytometry sample carrier to be used to immobilise soluble analytes from solution, in turn enabling the use of the planar mass cytometry sample carriers in quantitative methods of the invention (i.e. in imaging mass cytometry) as disclosed hereinabove.

Thus the invention provides a planar mass cytometry sample carrier comprising a planar substrate (e.g. a glass slide) and a PDA layer. In some instances, the planar substrate comprises an unreactive surface. The substrate can be a formed from an inorganic or organic material, a metal, a noble metal, a metal oxide, mica, silica, a ceramic, Indium Tin Oxide (ITO), Aluminium oxide ($Al_2O_3$), Magnetite ($Fe_3O_4$), $CuO_x$, Hematite (c-$Fe_2O_3$), Manganese spiral Ferrite ($MnFe_2O_4$), Magnesium hydroxide ($Mg(OH)_2$), Zinc oxide (ZnO), zirconium phosphonate, halloysite, montmorillonite, cellulose, chitosan, steel, sapphire, Cadmium selenide (CdSe), Cadmium sulphide (CdS), Gallium Arsenide (GaAs), carbon black, diamond, single walled carbon nanotubes, multiwalled carbon nanotubes, graphene, or a polymer such as polystyrene, poly(ethyleneterephthalate), polyaniline, poly(cyclopentadiene), poly(vinyl chloride), poly(vinylidene fluoride), nylon, poly(divinylbenzene), poly(tetrafluoroethylene), poly(dimethylsiloxane), poly (methylmethacrylate), polyimide, polyurethane, polypropylene.

Capture elements as described above can be directly attached to the PDA layer. Alternatively, polymers as discussed above for increasing the capacity of the planar mass cytometry sample carrier to bind to analytes can be attached to the PDA layer.

The polymer can be selected from the group consisting of linear polymers, copolymers, branched polymers, graft copolymers, block polymers, star polymers, and hyperbranched polymers. The backbone of the polymer can be derived from substituted polyacrylamide, polymethacrylate, or polymethacrylamide and can be a substituted derivative of a homopolymer or copolymer of acrylamides, methacrylamides, acrylate esters, methacrylate esters, acrylic acid or methacrylic acid. The polymer can be synthesised from the group consisting of reversible addition fragmentation polymerization (RAFT), atom transfer radical polymerization (ATRP), anionic polymerization (including single electron living radical polymerisation), nitroxide-mediated polymerisation (NMP), and photoiniferter-mediated polymerisation (PIMP). The step of providing the polymer can comprise synthesis of the polymer from compounds selected from the group consisting of N-alkyl acrylamides, N,N-dialkyl acrylamides, N-aryl acrylamides, N-alkyl methacrylamides, N,N-dialkyl methacrylamides, N-aryl methacrylamides, methacrylate esters, acrylate esters and functional equivalents thereof.

Grafting-to and grafting-from are the two principle mechanisms for generating polymer brushes attached to the PDA layer. In grafting to, the polymers are synthesised separately, and so synthesis is not constrained by the need to keep the PDA layered substrate stable. Here reversible addition-fragmentation chain transfer (RAFT) synthesis has excelled due to a large variety of monomers and easy functionalization. The chain transfer agent (CTA) can be readily used as functional group itself, a functionalized CTA can be used or the polymer chains can be post-functionalized.

A chemical reaction or physisorption is used to attach/graft the polymers to the planar mass cytometry sample carrier. Polymers comprising groups capable of covalently coupling to the PDA, including thiol, amino, and imidazole groups, can chemical react with the PDA. The reactive groups can be present at any point along the length of the polymer, including the polymer terminus, as pendant groups along the backbone of the polymer, or incorporated into the backbone of the polymer chain. One drawback of grafting-to is the usually lower grafting density, due to the steric repulsion of the coiled polymer chains during attachment to the surface. All grafting-to methods suffer from the drawback that a rigorous workup is necessary to remove the excess of free ligand from the functionalized particle or slide. For planar substrate-based mass cytometry sample carriers, this can be achieved by washing the functionalised slides with a solvent.

Thus the invention further provides planar mass cytometry sample carriers comprising a PDA layer, and further comprising polymeric groups covalently coupled to the PDA coating. The covalently coupled polymers can form a 3D polymer, e.g. a 3D polymer brush, around the PDA coated planar sample carrier, as described above.

Quantitation on Planar Mass Cytometry Sample Carriers

Quantitation from planar substrates can be achieved by the ablation of material from the mass cytometry sample carrier using the procedure typically applied in imaging mass cytometry.

In general terms, the sample on a planar mass cytometry sample carrier is placed in a sample chamber, which is the component in which the sample is placed when it is subjected to analysis. The sample chamber comprises a stage, which holds the mass cytometry sample carrier, and so, in operation, the immobilised sample of the invention. The sampling and ionisation system acts to remove material from the sample in the sample chamber which is converted into ions, either as part of the process that causes the removal of the material from the sample or via a separate ionisation system downstream of the sampling system. The different types of apparatus are discussed in more detail below.

The ionised material is then analysed by the second system which is the detector system. The detector system can take different forms depending upon the particular characteristic of the ionised sample material being determined, for example a mass detector in mass spectrometry-based apparatus.

Thus, in operation, the sample is taken into the apparatus, is sampled to generate ionised material using a laser system (sampling may generate vaporous/particular material, which is subsequently ionised by the ionisation system), and the ions of the sample material are passed into the detector system. Although the detector system can detect many ions, most of these will be ions of the atoms that naturally make up the sample. By labelling the sample with atoms not present in the material being analysed under normal conditions, or at least not present in significant amounts (for example certain transition metal atoms, such as rare earth metals; see section on labelling below for further detail), specific characteristics of the sample can be determined.

Accordingly, the invention provides a method for quantifying one or more analytes within a sample, comprising the steps of: a. providing the sample, wherein the one or more analytes are immobilised to a mass cytometry sample carrier, wherein the sample has been labelled with one or more mass tags comprising one or more labelling atoms, b. performing mass cytometry on the sample to determine the level of the one or more labelling atoms, wherein the level of the one or more labelling atoms corresponds to the copy number of the one or more analytes to quantify the analytes, wherein the method comprises sampling and ionizing sample material to form sample ions, and analysing said ions in a detector, such as a mass detector. In some embodiments, the sampling and ionisation comprises the step of laser ablation followed by separate ionisation of the sample material, such as in an ICP, to form sample ions. In some embodiments the sampling and ionisation comprises laser desorption ionisation (LDI) to form sample ions.

As explained above, the inventors noted that by using a 3D polymer, to which capture elements have been attached, to increase the capacity and selectivity of the mass cytometry sample carrier, improved quantitation is achieved. With the potential to immobilise an abundance of sample analytes to the mass cytometry sample carrier, if too large an amount of material is sampled, this may overload the detector. In methods which use lasers to sample the immobilised sample material, the quantity of sample material can be controlled by controlling the spot size of the laser at the sample location. This strategy can thus be applied where laser ablation is followed by a separate ionisation process (e.g. ICP or separate laser ionisation component) and can be applied in LDI-based analyses.

Thus in some embodiments, the limit of detection and/or dynamic range in step (b) is modulated by controlling the sampled spot size of the sample on which mass cytometry is performed. Thus, when a low concentration of analyte is present, a larger spot can be used, thereby generating more of the ions of analyte and ensuring a level of ions within the linear range of the detector is generated by the sampling and ionisation process (a larger spot size may, however, also cause fragmentation of the material being ablated from the sample, which is then thrown into neighbouring areas of the sample, causing contamination). When too much sample material is detected passing into the detector (such as might overload and degrade the detector), then a smaller spot size for ablation can be used. If it is desirable still to ablate the whole discrete area representing an area of interest on the mass cytometry sample carrier, then multiple of the smaller spots can be sampled until the desired amount of sample material has been analysed. Typically, control of the sampled spot size is deployed when the sample is immobilised on a mass cytometry sample carrier comprising a 3D polymer layer, such as a 3D polymer brush.

In certain aspects, multiple shots may be fired at the same region of the sample carrier in rapid succession, such as at a region comprising the same immobilized analyte as described herein. In certain aspects, a laser may be scanned across a region comprising the same immobilized analyte in order to provide a more intense signal (e.g., a continuous ablation plume) over a shorter period of time. Alternatively or in addition, multiple laser shots may be fired at the same spot to ablate the same immobilized analyte spread across different depths (along the z-axis). A higher repetition rate (e.g., quicker pulses) may allow for lower energy in each pulse, allowing for cleaner ablation without damaging surrounding sample.

As an alternative to laser-based sampling, as described below, the method of the invention can also employ ion bombardment as a means of generating ions for analysis. Here, a first focused primary ion beam is directed onto the sample to generate ejected secondary ions. These ejected ions (including any detectable ions from labelling atoms as discussed below) can be detected by a detector system for instance a mass spectrometer. The primary ions produced by the primary ion source bombard the surface of a sample in the sample chamber, transferring energy to the atoms of the sample. This bombardment generates a series of collisions between atoms within the sample. Some atoms near the surface of the sample recoil with enough energy to escape from the surface of the sample (sputtering). Some emitted particles are in an ionised state—these are the secondary ions, which can be subsequently detected.

Quantitation on Bead and Nanoparticle Based Mass Cytometry Sample Carriers

Where the mass cytometry sample carrier is particulate, such as a bead (including doped beads) or nanoparticle (include nanoparticles comprising crystals of one or more detectable elements or isotopes thereof), then the method of analysis is akin to mass cytometry of cells in solution. Here, particles are passed by a sampler into the apparatus and are analysed particle-by-particle (in the typical mode of analysis; however, sometimes, doublets, triplets or higher multimers may be deliberately introduced). The particles are ionised, e.g. by an ICP or laser ionisation component, and the elemental ions detected, e.g. in a mass detector such as a TOF detector.

In certain aspects, a particle may be more than 50 nm, 100 nm, 200 nm, 500 nm, 1 um, 2 um, 5 um or 10 um in diameter, and/or less than 100 nm, 200 nm, 500 nm, 1 um, 2 um, 5 um, 10 um or 50 um in diameter. For example, a particle may have a diameter at or between 50 nm and 100 nm, 50 nm and 200 nm, 50 nm and 500 nm, 50 nm and 1 um, 50 nm and 5 um, 50 nm and 10 um, 100 nm and 200 nm, 100 nm and 500 nm, 100 nm and 1 um, 100 nm and 5 um, 100 nm and 10 um, 200 nm and 500 nm, 200 nm and 1 um, 200 nm and 5 um, 200 nm and 10 um, 500 nm and 1 um, 500 nm and 5 um, 500 nm and 10 um, 1 um and 5 um, 1 um and 10 um, or 5 um and 10 um. The particle may be functionalized with antibody, and may be used to label immobilized antigen (in or on a solid support, cell, or tissue) or may be used to bind free analyte in solution. Particles bound to analyte in solution may be individually analysed by suspension flow cytometry. Alternatively, particles may be bound to a solid support may be linked by polymers extending from the surface of each particle.

A particle may comprise a metal core or polymer surface with one, or a combination of, elements or isotopes that corresponds to the antibody they are functionalized with. A mixture of particles functionalized with different antibodies and a different elemental/isotope (or combination of elements/isotopes) may be provided in admixture, and may be used for multiplexed analysis.

The surface of a particle (e.g., having a metal core, such as a metal nanocrystal core or a polymer core chelating or entrapping metal atoms) may be functionalized to bind an affinity reagent such as an antibody. For example, the particle may comprise a polymer shell comprising any suitable polymer known in the art or described herein. In certain aspects, the particle may comprise a monolayer of the polymer and/or may not extent from the particle surface. In certain aspects, the particle may comprise a branching polymer or a polymer extending from the particle surface, such as the 3D polymer as described herein, e.g., so as to increase binding of affinity reagent. Polymers, and methods of polymerization described for functionalization of planar surfaces may be used for particle coating.

Accordingly, in this regard, the invention provides a method of quantifying a plurality of analytes in a biological sample, each of said analytes being recognized by a corresponding capture element, said method comprising: (a) contacting said sample with a plurality of distinct sets of particles each distinct set of particles being characterized by having each particle within each said set having a similar elemental code but a differing elemental code from each particle of every other said distinct set, each distinct set of said particles having a distinct capture element bound to its surface, wherein said capture element on each set of particles specifically interacts with one of said analytes in said biological sample; (b) further contacting said sample with a plurality of mass-tagged SBPs that specifically binds to the analyte, and analyzing the particles to detect said mass tag indicating binding of the antigen to said mass-tagged SBP; and (c) simultaneously detecting the elemental code of each particle and the mass tag of the mass-tagged SBP.

Sample Immobilisation and Assay Formats

The methods performed herein include numerous ways of combining the sample analytes, the mass cytometry sample carrier and the detection reagents. These methods mirror the experimental approaches commonly utilised e.g. in ELISAs. For example, in a first instance, the sample analytes are immobilised to the same carrier, by incubating the sample analytes with the mass cytometry sample carrier under conditions such that the sample analytes are able to form complexes with the capture elements on the mass cytometry sample carrier. Following immobilisation of the sample analytes, the mass-tagged SBPs are added to the capture/element sample analyte complex(es). The immobilised and mass-tagged analytes can then be analysed as described above. Where the capture element and mass-tagged SBP are antibodies that bind to the same protein, they should bind to non-overlapping epitopes on the protein.

Accordingly, in some embodiments of the method of the invention, the step of providing the sample, wherein the one or more analytes are immobilised to a mass cytometry sample carrier, wherein the sample has been labelled with one or more mass tags comprising one or more labelling atoms, comprises the sub-steps of (i) incubating the one or more sample analytes with the mass cytometry sample carrier under conditions such that the sample analytes are able to form complexes with the capture elements on the mass cytometry sample carrier and (ii) incubating the mass cytometry sample carrier comprising immobilised sample analytes with one or more mass-tagged SBPs. In some instances, one or more cells are also immobilised and labelled using this process, simultaneously or sequentially with the immobilisation and labelling of the sample analytes.

Alternatively, sometimes, the sample analytes and mass-tagged SBPs are incubated together first under conditions such that complexes can form. Following complex formation, the complexes are then immobilised to the mass cytometry sample carrier, wherein the formed complex is immobilised to the mass cytometry sample carrier via capture elements on the mass cytometry sample carrier, with the capture elements being specific for the analyte or the analyte-mass-tagged SBP complex (capture elements specific for the mass-tagged SBP alone would capture the reagent without the analyte, and thus in most instances such capture elements would not be used because their use involves and increased burden in terms of sample preparation). The immobilised and mass-tagged analytes can then be analysed as described above. Where the capture element and mass-tagged SBP are antibodies that bind to the same protein, they should bind to non-overlapping epitopes on the protein.

Accordingly, in some embodiments of the method of the invention, the step of providing the sample, wherein the one or more analytes are immobilised to a mass cytometry sample carrier, wherein the sample has been labelled with one or more mass tags comprising one or more labelling atoms, comprises the sub-steps of (i) incubating the one or more sample analytes with the one or more mass-tagged SBPs under conditions such that the sample analytes are able to form complexes with the mass tagged-SBPs and (ii) incubating the resulting complexes with a mass cytometry sample carrier comprising one or more capture elements. In some instances, one or more cells are also immobilised and labelled using this process, simultaneously or sequentially with the immobilisation and labelling of the sample analytes.

These specific steps of providing a sample can be employed as appropriate in the methods described herein. As would be appreciate to one in the art, the method disclosed herein employ, wash steps between immobilisation to the mass cytometry sample support and/or labelling with the mass-tagged reagents to remove non-specifically bound material and so enhance signal to noise.

In another experimental set up common to ELISA techniques, in some instances, primary and secondary antibodies may be used to attach a mass tag to the analyte. Here, the primary antibody is used to bind to the analyte, and then a secondary antibody is used to bind to the primary antibody. The secondary antibody is mass-tagged. This approach may be used where, for instance, it is desirable to have a common reagent that can be used between different assays (e.g. the secondary antibody could be specific to a human/murine/rat/goat/rabbit etc. Fc region, or specific isotype from these species, with the primary antibody having that specific Fc region). This approach may be applied where it is desired to minimise the number of different antibodies that must be labelled with a mass tag, with the different experimental strategies being understood by the person of skill in the art and deployed as appropriate in different experimental scenarios. Accordingly, in some embodiments, the methods of the invention comprise first forming complexes between one or more primary antibodies and the sample analytes, followed by subsequently forming complexes between the primary antibodies bound to the sample analytes and one or more secondary antibodies that bind to the primary antibodies. As will be understood by one of skill in the art, there are various ways this can be achieved, for instance: (a)(i) immobilise one or more sample analytes to mass cytometry sample carrier, (ii) form complex between one or more sample analytes and one or more primary antibodies, and (iii) form complexes between the one or more primary antibodies and one or more secondary antibodies; (b)(i) form complex between one or more sample analytes and one or more primary antibodies, (ii) immobilise one or more complexes of sample analytes and primary antibodies to mass cytometry sample carrier, and (iii) form complexes between the one or more primary antibodies and one or more secondary antibodies; (c) (i) form complex between one or more sample analytes and one or more primary antibodies, (ii) form complexes between the one or more primary antibodies and one or more secondary antibodies and (iii) immobilise one or more complexes of sample analytes, primary antibodies and secondary antibodies to mass cytometry sample carrier.

In some instances, a range of secondary antibodies of the same specificity but comprising different mass tags (e.g. different elements or isotopes or blends thereof—see the labelling atoms section below at page 62). This panel of secondary antibodies of the same specificity can be employed for instance when multiple samples are being analysed in the same process, and in which the secondary antibody acts both to enable quantitation of the analyte and simultaneously the identification of the sample which was the source of the analyte in multi-sample analyses.

Multi-Sample Analyses

The method of the invention can be employed to analyse multiple samples simultaneously. Thus in some embodiments, the method is performed on a plurality of samples.

Again, because of the wide-reaching scope of application of the method of the invention, a variety of experimental protocols, involving different combinations of mass cytometry sample carriers and mass tagged SBPs can be used. These combinations of sample supports and mass tagged SBPs can be used both to enable quantitation of the sample analytes and to act as a "barcode" indicative of the sample from which the analyte was derived.

In some instances, more than one sample is immobilised to the same mass cytometry sample carrier. Sometimes, the mass cytometry sample carrier comprises a plurality of discrete regions, optionally wherein each sample from the plurality of samples is immobilised to a discrete region on the same mass cytometry sample carrier. In some embodiments, each sample is immobilised to at least three different discrete regions on the same mass cytometry sample carrier. This thereby enables repeat readings and statistical analyses to be performed on the recorded analyte levels.

In some instances, each sample is analysed to a discrete sample carrier or set of mass cytometry sample carriers, and the (sets of) mass cytometry sample carriers are analysed together, e.g. as a single suspension.

As highlighted in the preceding sections, one way of introducing a sample-specific label is through the use of separate mass tagged reagents which are bound to the analytes form a sample and wherein the mass tag of the reagent is varied sample to sample. In this manner, a unique elemental code is provided by the mass tagged SBPs. However, this process can necessitate an increased number of reagents, as multiple reagents comprising the same SBP but a different mass tag need to be prepared. The use of primary and secondary antibodies as described above is one way of minimising the number of reagents that need to be prepared, because the same secondary antibodies can be deployed across multiple different experiments, provided the primary antibodies used have the appropriate e.g. Fc to be recognised by the secondary antibody.

A further path to enable multiple analyses is for information to be derived from the mass cytometry sample carrier to which the sample analytes have been immobilised. As noted in the section on mass cytometer sample carrier substrates on page 14 above, where the mass cytometry sample carrier is a doped bead or a nanoparticle, the elemental composition of the bead or nanoparticle can act as the sample identifier. For instance, analytes from a first sample could be immobilised to a doped bead containing a labelling atom of a first element or isotope, and analytes from a second sample could be immobilised to a doped bead containing a labelling atom of a second element or isotope. Such beads could then be mixed together and analysed by mass cytometry as a single suspension, with the source of each bead being identifiable by the labelling atom it contains. Of course, rather than a single kind of labelling atom, multiple labelling atoms (e.g., a distinct combination isotopes or elements) can be used.

Thus in some instances all labelling atoms in a doped bead mass cytometry sample carrier or nanoparticle mass cytometry sample carrier are of the same atomic mass. Alternatively, a doped bead mass cytometry sample carrier or nanoparticle mass cytometry sample carrier can comprise labelling atoms of differing atomic mass. Alternatively, in some instances, a doped bead mass cytometry sample carrier or nanoparticle mass cytometry sample carrier may comprise a mixture of labelling atoms. In some instances, the doped bead mass cytometry sample carriers and/or nanoparticle mass cytometry sample carriers used to identify the sample source may comprise a mix of those with single labelling atom mass tags (i.e. a single kind of labelling atom) and mixes of labelling atoms in their mass tags.

Thus the invention provides a plurality of doped bead mass cytometry sample carriers and/or nanoparticle based mass cytometry sample carriers, each particle having an elemental code, wherein each said particle comprises labelling atom, said labelling atom being selected such that upon elemental spectrometry interrogation of each individual particle, a distinct signal is obtained from said at least one labelling atom. The invention also provides a plurality of sets of doped bead mass cytometry sample carriers and/or nanoparticle based mass cytometry sample carriers, in which each set of doped bead mass cytometry sample carriers and/or nanoparticle based mass cytometry sample carriers comprises the same at least one labelling atom signature, but each set differs. The sets of doped bead mass cytometry sample carriers and/or nanoparticle based mass cytometry sample carriers of the invention comprise one or more of the surface modifications described above, in particular a SAM and/or a 3D polymer, to which capture elements have been attached to enable capture of sample analytes. According to the invention the particles can have a uniform distribution as well as a non-uniform distribution of said particle sizes. Also, the particles can have at least one labelling atom uniformly as well as not uniformly distributed throughout each particle of said plurality of particles. The amount of said at least one labelling atom is between 1 and about 10 000 000 (or more) atoms of the element or isotope per particle.

In some instances, the mass cytometry sample carrier is a planar surface, such as a glass or plastic slide. Here, the mass cytometry sample carrier may again be encoded to identify the sample source, although as multiple planar mass cytometry sample carriers will not be analysed together in the same mixture of samples in the same way that beads/nanoparticles from different samples can be combined and analysed as a single suspension. Indeed, for planar mass cytometry sample carriers, it may be that the sample source of the particular analytes is encoded positionally, because liquid sample material can be controllably dispersed and immobilised on the carrier. Alternatively, because of the sensitivity and specificity of elemental spectrometry, different samples can be labelled differently (i.e. with a sample-identifying labelling atom or combination of labelling atoms) and immobilised to the same planar mass cytometry sample carrier, including to the same discrete region, should the mass cytometry sample carrier comprise discrete regions, and still be analysed simultaneously in parallel.

Element Standard

In certain aspects, a sample carrier may include an element standard. Methods of the subject disclosure may include applying an element standard to a sample carrier. Alternatively, or in addition, methods of the preset disclosure may include performing calibration based on the element standard and/or normalizing data obtained from the sample based on the element standard, as discussed further herein. Sample carriers and methods including an element standard may further include additional aspects or steps described elsewhere in the present disclosure.

Depending on the system and application, instrument sensitivity drift can be caused by a number of factors including ion optics drift, surface charging, detector drift (e.g., aging), temperature and gas flows drifts affecting diffusion, and electronics behaviour (e.g., plasma power, ion optics voltages, etc). Such instrument sensitivity can be accommodated by normalizing or calibrating using an element standard as described herein.

The element standard may include particles, film and/or a polymer that comprise one or more elements or isotopes. The element standard may include a consistent abundance of the elements or isotopes across the element standard. Alternatively, the element standard may include separate regions, each with a different amount of the one or more elements or isotopes (e.g., providing a standard curve). Different regions of the element standard may comprise a different combination of elements or isotopes.

As described herein, elemental standard particles (i.e., reference particles) of known elemental or isotopic composition may be added to the sample (or the sample support or sample carrier) for use as a reference during detection of target elemental ions in the sample. In certain embodiments, reference particles comprise metal elements or isotopes, such as transition metals or lanthanides. For example, reference particles may comprise elements or isotopes of mass greater than 60 amu, greater than 80 amu, greater than 100 amu, or greater than 120 amu. The quantity of the one or more elements or isotopes may be known. For example, the standard deviation of the number of atoms in reference particles of the same elemental or isotopic composition may be 50%, 40%, 30%, 20% or 10% of the average number of atoms.

In certain embodiments, the reference particles may be optically resolvable (e.g., may include one or more fluorophores).

In certain embodiments, reference particles may include elements or elemental isotopes with masses above 100 amu (e.g., elements in the lanthanide or transition element series). Alternatively, or in addition, reference particles may include a plurality of elements or elemental isotopes. For example, the reference particles may include elements or elemental isotopes that are identical to elements or elemental isotope of all, some or none of the labelling atoms in the sample. Alternatively, reference particles may include elements or elemental isotopes of masses above and below the masses of at least one of the labelling atoms. The reference particles may have a known quantity of one or more elements or isotopes. The reference particles may include reference particles with different elements or isotopes, or a different combination of elements or isotopes, than the target elements.

Element standard particles (i.e., reference particles) may have a similar diameter range as particles described generally herein, such as diameter at or between 1 nm and 1 um, between 10 nm and 500 nm, between 20 nm and 200 nm, between 50 nm and 100 nm, less than 1 um, less than 800 nm, less than 600 nm, less than 400 nm, less than 200 nm, less than 100 nm, less than 50 nm, less than 20 nm, less than 10 nm, or less than 1 nm. In certain aspects, the element standard particles may be nanoparticles. Elemental standard particles may have a similar composition as particles described generally herein, e.g., may have a metallic nanocrystal core and/or polymer surface.

Aspects of the invention include methods, samples and reference particles for normalization during a sample run by imaging mass spectrometry. Normalization may be performed by detection of individual reference particles. The reference particle may be used as a standard in imaging mass spectrometry, to correct for instrument sensitivity drift during the imaging of a sample, for example, according to any of the aspects of embodiments described below.

In certain aspects, a method of imaging mass spectrometry of a sample includes providing a sample on a solid support, where the sample includes one or more target elements, and where reference particles are distributed on or within the sample such that a plurality of the reference particles are individually resolvable. Ionizing and atomizing locations on the sample may be performed to produce target elemental ions and reference particle elemental ions. The target elemental ions and elemental ions from individual reference particles may be detected (e.g., at different locations on the sample). Target elemental ions may be normalized elemental ions of one or more individual reference particles detected in proximity to the detected target elemental ions. Alternatively or in addition, target elemental ions detected at a first and second location may be normalized to elemental ions detected from different individual reference particles. An image of the normalized target elemental ions may then be generated by any means known in the art or described herein.

Aspects of the invention include a biological sample on a solid support including a plurality of specific binding partners attached (e.g., covalently or non-covalently) to labelling atoms (e.g., to elemental tags that include labelling atoms). The biological sample may further include reference particles distributed on or within the biological sample on the solid support, such that a plurality of the reference particles are individually resolvable.

Aspects of the invention include preparing such a biological sample by providing a sample on a solid support, wherein the sample is a biological sample on a solid support, labelling the biological sample with specific binding partners attached to labelling atoms, and distributing reference particles on or within the biological sample, such that a plurality of the reference particles are individually resolvable. In certain aspects the sample is a biological sample may include one or more target elements, such as labelling atoms as described herein.

Aspects of the invention include the use of a reference particle, or a composition of reference particles, as a standard in imaging mass spectrometry to correct for instrument sensitivity drift during the imaging of a sample. In certain aspects the sample is a biological sample may include one or more target elements, such as labelling atoms as described herein.

The methods and uses described above may include additional elements, as described below.

The element standard may be deposited on or in a sample or a portion thereof. Alternatively, or in addition, the element standard may be at a position on the sample carrier distinct from a sample, or distinct from where a sample is to be placed.

In another example, elemental standard particles detected within temporal proximity of a portion of the sample, such as within 6 hours, 3 hours, 1 hour, 30 minutes, 10 minutes, 1 minute, 30 second, 10 seconds, 1 second, 500 us, 100 us, 50 us or 10 us, or within a certain number of laser or ion beam pulses (such as within 1000 pulses, 500 pulses, 100 pulses, or 50 pulses) from the detection of target elemental ions may be used to for normalization or calibration.

Target elements, such as labelling atoms, can be normalized within a sample run based on elemental ions detected from individual reference particles. For example, the subject methods may include switching between detecting elemental ions from individual reference particles and detecting only target elemental ions.

Target elemental ions may be detected as an intensity value, such as the area under an ion peak or the number of ion events (pulses) within the same mass channel. In certain embodiments, Detected target elemental ions may be normalized to elemental ions detected from individual reference particles. In certain embodiments, target elemental ions in different locations are normalized to different reference particles during the same sample run.

Normalization may include quantification of target elemental ions. In embodiments where the reference particle has a known quantity of one or more elements or isotopes (e.g., with a certain degree of certainty, as described above), the signal detected from elemental ions from the reference particle can be used to quantify target elemental ions.

Normalization to reference particles during a sample run may compensate for instrument sensitivity drift, in which the same number of target elements at different locations may be detected differently. Depending on the system and application, instrument sensitivity drift can be caused by a number of factors including ion optics drift, surface charging, detector drift (e.g., aging), temperature and gas flows drifts affecting diffusion, and electronics behaviour (e.g., plasma power, ion optics voltages, etc).

Figure 10:
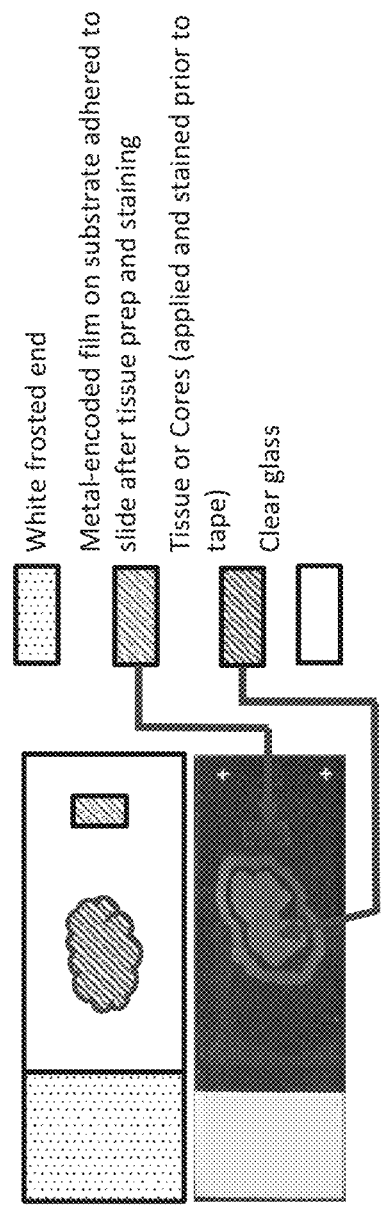
FIG. 10. Calibration tape on sample carrier: positioning respective to sample.

Aspects of the invention include an element film, or multiple element films, that may be applied to or present on a support, such as a sample carrier, as an element standard. The element film may be an adhesive element film and or a polymer film. For example, the element film may be a thin layer polymer film (e.g., encoded with a combination of elements or isotopes such as Y, In, Ce, Eu, Lu) on a polyester sticker, as depicted in FIG. 10. In certain embodiments, the element film may comprise a polymer (e.g., plastic) layer that can be mounted on a support. The support may be a sample slide, as described herein. In other embodiments, the element film may be pre-printed on a sample slide. As discussed herein, the sample slide may have one or more regions for binding cells and/or free analyte in a sample.

In certain aspects, the polymer film may be a polyester plastic film. The polymer may be a long chain polymer that, when mixed with a metal solution and volatile solvent, may create a film entrapping the metla after the solvent is evaporated. For example, the polymer film may be a poly (methyl methacrylate) polymer, and the solvent may be toluene. The polymer may be spin coated to allow for even distribution.

The element film may comprise at least 1, 2, 3, 4, 5, 10, or 20 different elements. The element film may comprise at least 1, 2, 3, 4, 5, 10, 20, 30, 40, or 50 different elemental isotopes. The elements or elemental isotopes may include metals, such as lanthanides and/or transition elements. Some or all of the elemental isotopes may have masses of 60 amu or higher, 70 amu or higher, 80 amu or higher, 90 amu or higher, or 100 amu or higher. In certain embodiments, the element film may comprise elements, elemental isotopes, or elemental isotope masses identical to one or more labelling atoms. For example, the element film may comprise mass tags identical to those used to tag sample on the same support. The element film may comprise elemental atoms bound to a polymer (either covalently or by chelation), or may comprise elemental atoms (either free, in clusters, or chelated) bound directly to the film. The element film may comprise an even coating of the elements or elemental isotopes across its surface, although individual isotopes may be present at the same or different amounts. Alternatively, different amounts of the same isotope may be patterned with a known distribution across the surface of the film. The element film may be at least 0.01, 0.1, 1, 10, or 100 square millimeters.

In certain aspects, the element film may be applied to a sample slide after tagging with mass tags (and potentially after washing of unbound mass tags). This may reduce cross contamination of sample from the element film. For example, use of the element film may result in less than 50%, 25%, 10%, or 5% increase in background during sample acquisition. The background may be the signal intensity of one or more (e.g., the majority of) the masses of isotopes present in the element film.

In certain aspects, the average number (or mean intensities) of each elemental isotope (or the majority of elemental isotopes) across the element film may have a coefficient of variation (CV) of less than 20%, less than 15%, less than 10%, or less than 5% or 2%. For example, the CV may be less than 6%. The CV may be measured across at least 2, 5, 10, 20, or 40 regions of interest, where each region is at least 100, 500, 1,000, 5,000, or 10,000 square micrometers. Similarly, the CV of the average number (or mean intensities) of each elemental isotope (or the majority of elemental isotopes) between element films may be less than 20%, 15%, 10%, 5%, or 2%.

The element film may be used for tuning, signal normalization and/or quantitation of labeling atoms (e.g., within a sample run and/or between sample runs). For example, the element film may be used throughout a long sample run (e.g., of more then 1, 2, 4, 12, 24, or 48 hours).

In certain aspects, the adhesive element film may be used to tune the apparatus before sample acquisition, between acquiring sample from different regions (or at different times) on a single solid support, or both. During tuning, the adhesive element film may be subjected to laser ablation, and the resulting ablation plume (e.g., transient) may be transferred to a mass detector as described herein. The spatial resolution, transients cross talk, and/or signal intensity (e.g., number of ion counts over one or more pushes, such as across all pushes in a given transient) may then be read out. One or more parameters may be adjusted based on the readout. Such parameters may include gas flow (e.g., sheath, carrier, and/or makeup gas flow), voltage (e.g., voltage applied to an amplifier or ion detector), and/or optical parameters (e.g., ablation frequency, ablation energy, ablation distance, etc.). For example, the voltage applied to an ion detector may be adjusted such that the signal intensity returns to an expected value (e.g., preset value or value obtained from an earlier signal intensity obtained from the same, or similar, adhesive element film).

In certain aspects, the adhesive element film may be used to normalize signal intensity from labeling atoms detected between samples on different solids supports, from labeling atoms detected between regions (or at different times) from a sample on a single solid support, or both. Normalization is performed after sample acquisition, and allows for comparison of signal intensities obtained from different samples, regions, times or operating conditions. Signal intensities (e.g., ion count) acquired from a given elemental isotope (e.g., associated with a mass tag) of a sample or region thereof may be normalized to the signal intensity of the same (or similar) elemental isotope(s) acquired from element film in close spatial or temporal proximity. For example, element film within spatial proximity, such as within 100 um, 50 um, 25 um, 10 um or 5 um of the detected target elemental ions may be used for normalization. In another example, element film detected within temporal proximity such as within 1 minute, 30 second, 10 seconds, 1 second, 500 us, 100 us, 50 us or 10 us, or within a certain number of laser or ion beam pulses (such as within 1000 pulses, 500 pulses, 100 pulses, or 50 pulses) from the detection of target elemental ions may be used to for normalization.

Normalization may include quantification of target elemental ions (e.g., ionized elemental isotopes). In embodiments where the element film has a known quantity of one or more elements or isotopes (e.g., with a certain degree of certainty, as described above), the signal detected from elemental ions from the element film can be used to quantify target elemental ions.

Normalization to element film during a sample run may compensate for instrument sensitivity drift, in which the same number of target elements at different locations may be detected differently. Depending on the system and application, instrument sensitivity drift can be caused by a number of factors including ion optics drift, surface charging, detector drift (e.g., aging), temperature and gas flows drifts affecting diffusion, and electronics behavior (e.g., plasma power, ion optics voltages, etc). Alternatively or in addition to normalization, parameters affecting the above instrument sensitivity drift factors may be adjusted based on the signal acquired from the element film.

As described below, an elemental (e.g., elemental isotope) standard may be used to generate a standard curve to quantify the amount of mass tags (e.g., number of labeling atoms) or the number of an analyte bound by a given mass tag. Multiple element films (or multiple regions of a single element film) with different known amounts of an element or elemental isotope may be used to generate such a standard curve.

In certain embodiments, the elemental film may be a metal-containing standard on an adhesive tape. This tape can be applied to a stained tissue slide when long image acquisition. These long acquisitions can benefit from periodic sampling to acquire data for active surveillance of instrument performance. This further enables standardization and/or normalization for longitudinal studies.

Figure 11:
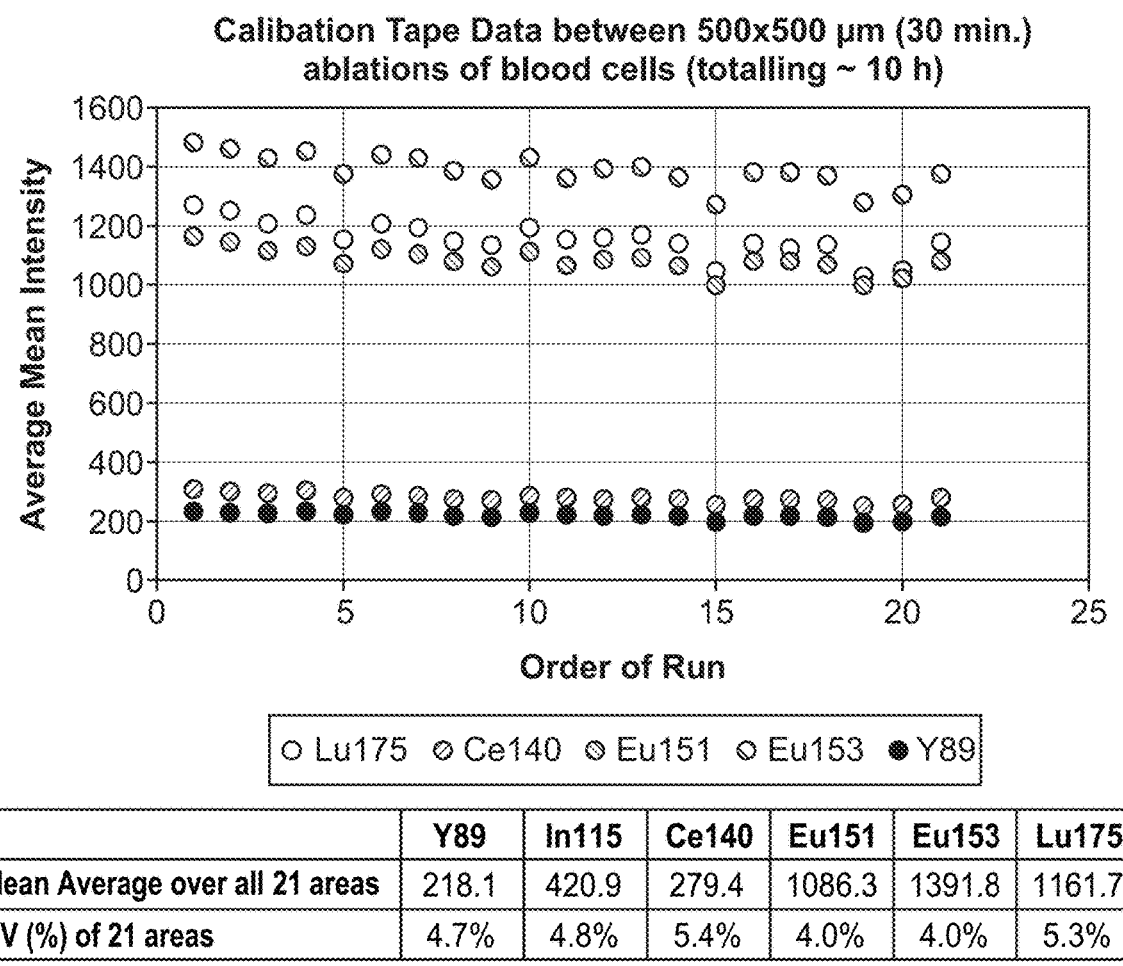
FIG. 11. Data obtained from calibrations tape: signal intensity of each elemental isotope obtained by laser ablation-ICP-MS and variance of signal across multiple areas.

In one example, as shown in FIG. 11, a long sample run alternated between the element standard film (as opposed to a tuning slide) every 30 minutes. The CV of the intensity over 21 different areas on the calibration tape comprising isotopes Y89, In 115, Ce 140, Eu 151, Eu 153 and Lu 175 were comparable to the variation in a traditional tuning slide.

Calibration Curve for Quantitation and/or Normalization

As noted above, elemental analysis, including elemental mass spectrometry such as mass cytometry and imaging mass cytometry, because of its extreme selectivity and sensitivity, has become a powerful tool for the quantitation of a broad range of bioanalytes including pharmaceuticals, metabolites, peptides and proteins. However the signal generated by the compound can vary between runs due to differences in sample introduction, ionization process, ion acceleration, ion separation, and ion detection. Thus quantitation may rely on internal standards that undergo the same processes as the analyte.

In some embodiments, to enable quantitation of the analytes in the sample, the measurement from the sample is compared to known standards. Standards can be used to form a calibration curve for the ion counts of labelling atoms (e.g., for quantitating ion counts from the sample), and from that absolute quantitation of an analyte can be calculated.

In some embodiments, the calibration curve comprises at least two points, such as at least 3, at least 4, at least 5, at least 6, at least 7, at least 8, at least 9, or 10 or more points. Typically, at least 3 repeats of each point are performed.

The calibration curve may be determined prior to analysis of the sample, during the analysis of the sample, or after analysis of the sample. In some instances, calibration may be performed before and after, before and during, during and after or before, during and after the analysis of the sample.

The form of the standards is varied, and can be determined as appropriate by the skilled person based on the particular experimental being performed.

In one embodiment, the standard is in the form of a set of doped polystyrene beads, with different beads being doped with different known levels of a labelling atom. From this, a calibration curve correlating the known level with the ion count can be generated. In some embodiments, a different kind of bead is used for each different mass channel (i.e. the standards for each labelling atom are discrete). In some embodiments, each bead is doped with more than one labelling atom, such that calibration curves can be generated for multiple mass channels at the same time, to maximise procedural efficiency. In some instances, all mass channels in an experiment can be obtained from the same set of doped beads. The bead standards can be fed into the same apparatus in the same way as experimental beads/nanoparticles (with sample analytes immobilised to them) or cells would be in a typical mode of operation for a mass cytometer, whereupon they are ionised and the elemental ions detected.

In one embodiment, the standard is in the form of a nanoparticle (e.g. core-shell nanoparticle), with different nanoparticles containing different known levels of a labelling atom (e.g. crystals of the labelling atom element/isotope). From this, a calibration curve correlating the known level with the ion count can be generated. In some embodiments, a different kind of nanoparticle is used for each different mass channel (i.e. the standards for each labelling atom are discrete). In some embodiments, each nanoparticle comprises crystals of one labelling atom, such that calibration curves can be generated for multiple mass channels at the same time, to maximise procedural efficiency. In some instances, all mass channels in an experiment can be obtained from the same set of nanoparticles. The nanoparticle standards can be fed into the same apparatus in the same way as experimental beads/nanoparticles (with sample analytes immobilised to them) or cells would be in a typical mode of operation for a mass cytometer, whereupon they are ionised and the elemental ions detected.

In one embodiment, the standard is in the form of a series of deposited spots on a planar mass cytometry sample carrier, with different spots containing different known levels of a labelling atom. From this, a calibration curve correlating the known level with the ion count can be generated. In some embodiments, a different kind of spot is used for each different mass channel (i.e. the standards for each labelling atom are discrete). In some embodiments, each spot comprises crystals of one labelling atom, such that calibration curves can be generated for multiple mass channels at the same time, to maximise procedural efficiency. In some instances, all mass channels in an experiment can be obtained from the same set of spots. The spots would be read in the same way as for e.g. a stained tissue section on a slide; the spots would be sampled and ionised, such as by laser ablation and ICP, LDI or SIMS, whereupon the elemental ions detected.

Accordingly, in some embodiments, the quantitation method of the invention comprises the step of generating a calibration curve from a set of standards comprising known quantities of labelling atoms. The method may also comprise calculating the quantity of an analyte in the sample based on a calibration curve.

Calibration may include on or more of adjusting a z-position of the slide, laser energy, rate of laser pulses, laser optics, gas flow, ion optics, and/or a voltage applied to a detector.

Kits, and Use Thereof to Produce Immobilised Labelled Samples

The invention also provides a series of kits of use in performing methods as disclosed herein. For instance, the kits may comprise at least two series of particulate mass cytometry sample carriers (e.g. beads or crystalline particles) each series of which comprises an elemental coding distinct from the other series of mass cytometry sample carriers (the elemental coding before formed of labelling atoms, and combinations thereof, as described above) wherein the particulate beads comprise (i) a surface assembled monolayer, (ii) a 3D polymer, to which capture elements can be conjugated. Alternatively, the kits of the invention may comprise at least two series of particulate mass cytometry sample carriers (e.g. beads or crystalline particles) each series of which comprises an elemental coding distinct from the other series of mass cytometry sample carriers (the elemental coding formed of labelling atoms, and combinations thereof, as described above) wherein the particulate beads comprise (i) a surface assembled monolayer, (ii) a 3D polymer, to which capture elements have been conjugated. In some instances, the above kits can further comprise reagents for generating mass-tagged SBPs (e.g. the mass tag components, which can be reacted with SBPs as desired by the end user).

Use of these kits on a sample thus will result in a variety of immobilised samples. The invention therefore provides an immobilised sample, in which one or more analytes are immobilised to a mass cytometry sample carrier via one or more capture elements on the mass cytometry sample carrier, and wherein the sample is labelled with one or more mass-tagged SBPs.

Applications of the Quantitation Methods of the Invention

The invention can quantify one or more analytes of interest even from samples and mixtures containing a high number of other biomolecules. As such the invention is particularly useful in quantitation of analytes from biological sample which typically contain a multitude of other species; such as the validation or quantitation of biomarkers from biological samples.

As used herein "biomarker" refers to a protein or polypeptide which is differentially present in samples from subjects having a genotype or phenotype of interest and/or who have been exposed to a condition of interest, as compared to equivalent samples from control subjects not having said genotype or phenotype and/or not having been exposed to said condition.

Particularly relevant phenotypes may be pathological conditions in patients, such as, e.g., cancer, an inflammatory disease, autoimmune disease, metabolic disease, CNS disease, ocular disease, cardiac disease, pulmonary disease, hepatic disease, gastrointestinal disease, neurodegenerative disease, genetic disease, infectious disease or viral infection; visa-vis the absence thereof in healthy controls. Other comparisons may be envisaged between samples from, e.g., stressed vs. non-stressed conditions/subjects, drug-treated vs. non drug-treated conditions/subjects, benign vs. malignant diseases, adherent vs. non-adherent conditions, infected vs. uninfected conditions/subjects, transformed vs. untransformed cells or tissues, different stages of development, conditions of overexpression vs. normal expression of one or more genes, conditions of silencing or knock-out vs. normal expression of one or more genes, and so on.

For example, a protein may be denoted as differentially present between two samples or between two sample groups if the protein's quantity in one sample or one sample group is at least about 1.2-fold, at least about 1.3-fold, at least about 1.5-fold, at least about 1.8-fold, at least about 2-fold, at least about 3-fold, at least about 5-fold, at least about 7-fold, at least about 9-fold or at least about 10-fold of its quantity in the other sample or the other sample group; or if the protein is detectable in one sample or one sample group but not detectable in the other sample or the other sample group.

Accordingly, the invention provides a method of diagnosing a condition or disease in a subject, comprising the steps of:

a. providing a sample, immobilised to a mass cytometry sample carrier comprising one or more capture elements specific for one or more biomarkers of the disease, obtained from the subject, wherein the sample has been labelled with one or more mass-tagged SBPs specific for one or more biomarkers of the disease;
b. performing mass cytometry on the sample to determine the level of the one or more labelling atoms in the mass tag;
c. comparing the level of the one or more labelling atoms with the level determined from a healthy control, wherein a difference in the level of one or more labelling atoms between the subject and control indicates that the subject is suffering from the disease or condition. In some instances, the disease state is indicated by an increase in the level of biomarker vis-à-vis the healthy control. In some instances, the disease state is indicated by a decrease in the level of biomarker vis-à-vis the healthy control. As a person of skill in the art will appreciate, the specific difference will vary (increase or decrease) and will depend both on the biomarker and the disease. In some instances, a conclusion will be drawn on the basis of the relative levels of at least 3, such as at least 5 biomarkers.

Accordingly, the invention provides a method of predicting the likelihood that a treatment for a disease will be successful in a subject, comprising the steps of:
a. providing a sample, immobilised to a mass cytometry sample carrier comprising one or more capture elements specific for one or more biomarkers of the disease, obtained from the subject, wherein the sample has been labelled with one or more mass-tagged SBP specific for one or more biomarkers of the disease;
b. performing mass cytometry on the sample to determine the level of the one or more labelling atoms in the mass tag;
c. comparing the level of the one or more labelling atoms with the level determined from a treatment responsive control, wherein a difference in the level of one or more labelling atoms between the subject and control indicates that the subject is unlikely to respond to the treatment. In some instances, the level between the sample and the control can differ, with the control level setting an upper or lower limit which is used to determine the likelihood of an effective treatment. For instance, in some embodiments, the sample may be deemed to indicate that the treatment would be effective in the subject if the level of a biomarker is the same as or below the level of the responsive control. In some embodiments, the sample may be deemed to indicate that the treatment would be effective in the subject if the level of a biomarker is the same as or above the level of the responsive control. In some instances, a conclusion will be drawn on the basis of the relative levels of at least 3, such as at least 5 biomarkers.

The invention also provides a method of determining the efficacy of therapy in the treatment of a disease or condition in a subject, comprising the steps of:
a. providing a sample, immobilised to amass cytometry sample carrier comprising one or more capture elements specific for one or more biomarkers of the disease, obtained from the subject, wherein the sample has been labelled with a mass-tagged SBP specific for one or more biomarkers of the disease;
b. performing mass cytometry on the sample to determine the level of the one or more labelling atoms in the mass tag;
c. comparing the level of the one or more labelling atoms with the level determined from an earlier time in the therapy, such as prior to initiation of therapy, wherein a difference in the level of one or more labelling atoms overtime indicates the response of the subject to the therapy. In some instances, response to therapy is indicated by an increase in the level of biomarker over time. In some instances, the disease state is indicated by a decrease in the level of biomarker over time. As the person of skill in the art will appreciate, the specific difference will vary (increase or decrease) and will depend both on the treatment and the disease. In some instances, a conclusion will be drawn on the basis of the relative levels of at least 3, such as at least 5 biomarkers.

Mass Tagged Detection Reagents

Mass-tagged detection reagents as used herein comprise a number of components. The first is the SBP. The second is the mass tag. The mass tag and the SBP are joined by a linker, formed at least in part of by the conjugation of the mass tag and the SBP. The linkage between the SBP and the mass tag may also comprise a spacer. The mass tag and the SBP can be conjugated together by a range of reaction chemistries. Exemplary conjugation reaction chemistries include thiol maleimide, NHS ester and amine, or click chemistry reactivities (preferably Cu(I)-free chemistries), such as strained alkyne and azide, strained alkyne and nitrone and strained alkene and tetrazine.

Mass Tags

The mass tag used in the present invention can take a number of forms. Typically, the tag comprises at least one labelling atom. A labelling atom is discussed herein below. Mass tags may also be referred to herein as element tags.

Accordingly, in its simplest form, the mass tag may comprise a metal-chelating moiety which is a metal-chelating group with a metal labelling atom co-ordinated in the ligand. In some instances, detecting only a single metal atom per mass tag may be sufficient. However, in other instances, it may be desirable of each mass tag to contain more than one labelling atom. This can be achieved in a number of ways, as discussed below.

Elemental analysis (e.g., atomic or mass analysis) can be used to detect mass tags (e.g., element tags, such as isotope specific tags) associated with an analyte. Mass tags, such as element-tagged affinity reagents or element-tagged supports or beads, can be used to label analytes based on the absence or presence of desired biomolecules in the analytes. A mass tag, or tag, is a chemical moiety which includes an element, or multiple elements, having one or many isotopes (referred to as tag atoms) attached to a supporting molecular structure, or that is capable of binding said element(s) or isotope(s). The mass tag can also comprise the means of attaching the element tag to a molecule of interest or target molecule (for example, an analyte). Different mass tags may be distinguished on the basis of the elemental composition of the tags. An mass tag can contain many copies of a given isotope and can have a reproducible copy number of each isotope in each tag. Suitable mass tags can include polymers (e.g., linear or branched polymers) with metal binding pendant groups, such as metal chelating moieties (e.g., tetraxetan (DOTA) or pentetic acid (DTPA)). Mass tags may be a nanoparticle, such metal core encased in a polymer shell. A mass tag may be functionally distinguishable from other element tags in the same sample because its elemental or isotopic composition is different from that of the other tags. A first means to generate a mass tag that can contain more than one labelling atom is the use of a polymer comprising metal-chelating ligands attached to more than one subunit of the polymer. The number of metal-chelating groups capable of binding at least one metal atom in the polymer can be between approximately 1 and 10,000, such as 5-100, 10-250, 250-5,000, 500-2,500, or 500-1,000. At least one metal atom can be bound to at least one of the metal-chelating groups. The polymer can have a degree of polymerization of between approximately 1 and 10,000, such as 5-100, 10-250, 250-5,000, 500-2,500, or 500-1,000. Accordingly, a polymer based mass tag can comprise between approximately 1 and 10,000, such as 5-100, 10-250, 250-5,000, 500-2,500, or 500-1,000 labelling atoms.

The polymer can be selected from the group consisting of linear polymers, copolymers, branched polymers, graft copolymers, block polymers, star polymers, and hyperbranched polymers. The backbone of the polymer can be derived from substituted polyacrylamide, polymethacrylate, or polymethacrylamide and can be a substituted derivative of a homopolymer or copolymer of acrylamides, methacrylamides, acrylate esters, methacrylate esters, acrylic acid or methacrylic acid. The polymer can be synthesised from the group consisting of reversible addition fragmentation polymerization (RAFT), atom transfer radical polymerization (ATRP), anionic polymerization (including single electron living radical polymerisation), nitroxide-mediated polymerisation (NMP), and photoiniferter-mediated polymerisation (PIMP). The step of providing the polymer can comprise synthesis of the polymer from compounds selected from the group consisting of N-alkyl acrylamides, N,N-dialkyl acrylamides, N-aryl acrylamides, N-alkyl methacrylamides, N,N-dialkyl methacrylamides, N-aryl methacrylamides, methacrylate esters, acrylate esters and functional equivalents thereof.

The polymer can be water soluble. This moiety is not limited by chemical content. However, it simplifies analysis if the skeleton has a relatively reproducible size (for example, length, number of tag atoms, reproducible dendrimer character, etc.). The requirements for stability, solubility, and non-toxicity are also taken into consideration. Thus, the preparation and characterization of a functional water soluble polymer by a synthetic strategy that places many functional groups along the backbone plus a different reactive group (the linking group), that can be used to attach the polymer to a molecule (for example, an SBP), through a linker and optionally a spacer. The size of the polymer is controllable by controlling the polymerisation reaction. Typically the size of the polymer will be chosen so as the radiation of gyration of the polymer is as small as possible, such as between 2 and 11 nanometres. The length of an IgG antibody, an exemplary SBP, is approximately 10 nanometres, and therefore an excessively large polymer tag in relation to the size of the SBP may sterically interfere with SBP binding to its target.

The metal-chelating group that is capable of binding at least one metal atom can comprise at least four acetic acid groups. For instance, the metal-chelating group can be a diethylenetriaminepentaacetate (DTPA) group or a 1,4,7,10-tetraazacyclododecane-1,4,7,10-tetraacetic acid (DOTA) group. Alternative groups include Ethylenediaminetetraacetic acid (EDTA) and ethylene glycol-bis(β-aminoethyl ether)-N,N,N',N'-tetraacetic acid (EGTA).

The metal-chelating group can be attached to the polymer through an ester or through an amide. Examples of suitable metal-chelating polymers include the X8 and DM3 polymers available from Fluidigm Canada, Inc.

The polymer can be water soluble. Because of their hydrolytic stability, N-alkyl acrylamides, N-alkyl methacrylamides, and methacrylate esters or functional equivalents can be used. A degree of polymerization (DP) of approximately 1 to 1000 (1 to 2000 backbone atoms) encompasses most of the polymers of interest. Larger polymers are in the scope of the invention with the same functionality and are possible as would be understood by practitioners skilled in the art. Typically the degree of polymerization will be between 1 and 10,000, such as 5-100, 10-250, 250-5,000, 500-2,500, or 500-1,000. The polymers may be amenable to synthesis by a route that leads to a relatively narrow polydispersity. The polymer may be synthesized by atom transfer radical polymerization (ATRP) or reversible addition-fragmentation (RAFT) polymerization, which should lead to values of Mw (weight average molecular weight)/Mn (number average molecular weight) in the range of 1.1 to 1.2. An alternative strategy involving living anionic polymerization, where polymers with Mw/Mn of approximately 1.02 to 1.05 are obtainable. Both methods permit control over end groups, through a choice of initiating or terminating agents. This allows synthesizing polymers to which the linker can be attached. A strategy of preparing polymers containing functional pendant groups in the repeat unit to which the ligated transition metal unit (for example a Ln unit) can be attached in a later step can be adopted. This embodiment has several advantages. It avoids complications that might arise from carrying out polymerizations of ligand containing monomers.

To minimize charge repulsion between pendant groups, the target ligands for ($M^{3+}$) should confer a net charge of $-1$ on the chelate.

Polymers that be used in the invention include:
random copolymer poly(DMA-co-NAS): The synthesis of a 75/25 mole ratio random copolymer of N-acryloxysuccinimide (NAS) with N,N-dimethyl acrylamide (DMA) by RAFT with high conversion, excellent molar mass control in the range of 5000 to 130,000, and with Mw/Mn≈1.1 is reported in Relógio et al. (2004) (Polymer, 45, 8639-49). The active NHS ester is reacted with a metal-chelating group bearing a reactive amino group to yield the metal-chelating copolymer synthesised by RAFT polymerization.

poly(NMAS): NMAS can be polymerised by ATRP, obtaining polymers with a mean molar mass ranging from 12 to 40 KDa with Mw/Mn of approximately 1.1 (see e.g. Godwin et al., 2001; Angew. Chem. Int. Ed, 40: 594-97).

poly(MAA): polymethacrylic acid (PMAA) can be prepared by anionic polymerization of its t-butyl or trimethylsilyl (TMS) ester.

poly(DMAEMA): poly(dimethylaminoethyl methacrylate) (PDMAEMA) can be prepared by ATRP (see Wang et al, 2004, J. Am. Chem. Soc, 126, 7784-85). This is a well-known polymer that is conveniently prepared with mean Mn values ranging from 2 to 35 KDa with Mw/Mn of approximately 1.2 This polymer can also be synthesized by anionic polymerization with a narrower size distribution.

polyacrylamide, or polymethacrylamide.

The metal-chelating groups can be attached to the polymer by methods known to those skilled in the art, for example, the pendant group may be attached through an ester or through an amide. For instance, to a methylacrylate based polymer, the metal-chelating group can be attached to the polymer backbone first by reaction of the polymer with ethylenediamine in methanol, followed by subsequent reaction of DTPA anhydride under alkaline conditions in a carbonate buffer.

A second means is to generate nanoparticles which can act as mass tags. A first pathway to generating such mass tags is the use of nanoscale particles of the metal which have been coated in a polymer. Here, the metal is sequestered and shielded from the environment by the polymer, and does not react when the polymer shell can be made to react e.g. by functional groups incorporated into the polymer shell. The functional groups can be reacted with linker components (optionally incorporating a spacer) to attach click chemistry reagents, so allowing this type of mass tag to plug in to the synthetics strategies discussed above in a simple, modular fashion.

Grafting-to and grafting-from are the two principle mechanism for generating polymer brushes around a nanoparticle. In grafting to, the polymers are synthesised separately, and so synthesis is not constrained by the need to keep the nanoparticle colloidally stable. Here reversible addition-fragmentation chain transfer (RAFT) synthesis has excelled due to a large variety of monomers and easy functionalization. The chain transfer agent (CTA) can be readily used as functional group itself, a functionalized CTA can be used or the polymer chains can be post-functionalized. A chemical reaction or physisorption is used to attach the polymers to the nanoparticle. One drawback of grafting-to is the usually lower grafting density, due to the steric repulsion of the coiled polymer chains during attachment to the particle surface. All grafting-to methods suffer from the drawback that a rigorous workup is necessary to remove the excess of free ligand from the functionalized nanocomposite particle. This is typically achieved by selective precipitation and centrifugation. In the grafting-from approach molecules, like initiators for atomic transfer radical polymerization (ATRP) or CTAs for (RAFT) polymerizations, are immobilized on the particle surface. The drawbacks of this method are the development of new initiator coupling reactions. Moreover, contrary to grafting-to, the particles have to be colloidally stable under the polymerization conditions.

An additional means of generating a mass tag is via the use of doped beads. Chelated lanthanide (or other metal) ions can be employed in miniemulsion polymerization to create polymer particles with the chelated lanthanide ions embedded in the polymer. The chelating groups are chosen, as is known to those skilled in the art, in such a way that the metal chelate will have negligible solubility in water but reasonable solubility in the monomer for miniemulsion polymerization. Typical monomers that one can employ are styrene, methylstyrene, various acrylates and methacrylates, among others as is known to those skilled in the art. For mechanical robustness, the metal-tagged particles have a glass transition temperature (Tg) above room temperature. In some instances, core-shell particles are used, in which the metal-containing particles prepared by miniemulsion polymerization are used as seed particles for a seeded emulsion polymerization to control the nature of the surface functionality. Surface functionality can be introduced through the choice of appropriate monomers for this second-stage polymerization. Additionally, acrylate (and possible methacrylate) polymers are advantageous over polystyrene particles because the ester groups can bind to or stabilize the unsatisfied ligand sites on the lanthanide complexes. An exemplary method for making such doped beads is: (a) combining at least one labelling atom-containing complex in a solvent mixture comprising at least one organic monomer (such as styrene and/or methyl methacrylate in one embodiment) in which the at least one labelling atom-containing complex is soluble and at least one different solvent in which said organic monomer and said at least one labelling atom-containing complex are less soluble, (b) emulsifying the mixture of step (a) for a period of time sufficient to provide a uniform emulsion; (c) initiating polymerization and continuing reaction until a substantial portion of monomer is converted to polymer, and (d) incubating the product of step (c) for a period of time sufficient to obtain a latex suspension of polymeric particles with the at least one labelling atom-containing complex incorporated in or on the particles therein, wherein said at least one labelling atom-containing complex is selected such that upon interrogation of the polymeric mass tag, a distinct mass signal is obtained from said at least one labelling atom. By the use of two or more complexes comprising different labelling atoms, doped beads can be made comprising two or more different labelling atoms. Furthermore, controlling the ration of the complexes comprising different labelling atoms, allows the production of doped beads with different ratios of the labelling atoms. By use of multiple labelling atoms, and in different radios, the number of distinctively identifiable mass tags is increased. In core-shell beads, this may be achieved by incorporating a first labelling atom-containing complex into the core, and a second labelling atom-containing complex into the shell.

A yet further means is the generation of a polymer that include the labelling atom in the backbone of the polymer rather than as a co-ordinated metal ligand. For instance, Carerra and Seferos (Macromolecules 2015, 48, 297-308) disclose the inclusion of tellurium into the backbone of a polymer. Other polymers incorporating atoms capable as functioning as labelling atoms tin-, antimony- and bismuth-incorporating polymers. Such molecules are discussed inter alia in Priegert et al., 2016 (Chem. Soc. Rev., 45, 922-953).

Thus the mass tag can comprise at least two components: the labelling atoms, and a polymer, which either chelates, contains or is doped with the labelling atom. In addition, the mass tag comprises an attachment group (when not-conjugated to the SBP), which forms part of the chemical linkage between the mass tag and the SBP following reaction of the two components, in a click chemistry reaction in line with the discussion above.

Labelling Atom

Labelling atoms that can be used with the disclosure include any species that are detectable by MS or OES and that are substantially absent from the unlabelled tissue sample. Thus, for instance, $^{12}C$ atoms would be unsuitable as labelling atoms because they are naturally abundant, whereas $^{11}C$ could in theory be used for MS because it is an artificial isotope which does not occur naturally. Often the labelling atom is a metal In preferred embodiments, however, the labelling atoms are transition metals, such as the rare earth metals (the 15 lanthanides, plus scandium and yttrium). These 17 elements (which can be distinguished by OES and MS) provide many different isotopes which can be easily distinguished (by MS). A wide variety of these elements are available in the form of enriched isotopes e.g. samarium has 6 stable isotopes, and neodymium has 7 stable isotopes, all of which are available in enriched form. The 15 lanthanide elements provide at least 37 isotopes that have non-redundantly unique masses. Examples of elements that are suitable for use as labelling atoms include Lanthanum (La), Cerium (Ce), Praseodymium (Pr), Neodymium (Nd), Promethium (Pm), Samarium (Sm), Europium (Eu), Gadolinium, (Gd), Terbium (Tb), Dysprosium (Dy), Holmium (Ho), Erbium (Er), Thulium (Tm), Ytterbium (Yb), Lutetium (Lu), Scandium (Sc), and Yttrium (Y). In addition to rare earth metals, other metal atoms are suitable for detection e.g. gold (Au), platinum (Pt), iridium (Ir), rhodium (Rh), bismuth (Bi), etc. The use of radioactive isotopes is not preferred as they are less convenient to handle and are unstable e.g. Pm is not a preferred labelling atom among the lanthanides.

In order to facilitate time-of-flight (TOF) analysis (as discussed herein) it is helpful to use labelling atoms with an atomic mass within the range 80-250 e.g. within the range 80-210, or within the range 100-200. This range includes all of the lanthanides, but excludes Sc and Y. The range of 100-200 permits a theoretical 101-plex analysis by using different labelling atoms, while taking advantage of the high spectral scan rate of TOF MS. As mentioned above, by choosing labelling atoms whose masses lie in a window above those seen in an unlabelled sample (e.g. within the range of 100-200), TOF detection can be used to provide rapid imaging at biologically significant levels.

Various numbers of labelling atoms can be attached to a single SBP member dependent upon the mass tag used (and so the number of labelling atoms per mass tag) and the number of mass tags that are attached to each SBP). Greater sensitivity can be achieved when more labelling atoms are attached to any SBP member. For example, greater than 10, 20, 30, 40, 50, 60, 70, 80, 90 or 100 labelling atoms can be attached to a SBP member, such as up to 10,000, for instance as 5-100, 10-250, 250-5,000, 500-2,500, or 500-1,000 labelling atoms. As noted above, monodisperse polymers containing multiple monomer units may be used, each containing a chelator such as diethylenetriaminepentaacetic acid (DTPA) or DOTA. DTPA, for example, binds 3 lanthanide ions with a dissociation constant of around $10^{-6}$ M. These polymers can terminate in a thiol which can be used for attaching to a SBP via reaction of that with a maleimide to attach a click chemistry reactivity in line with those discussed above. Other functional groups can also be used for conjugation of these polymers e.g. amine-reactive groups such as N-hydroxy succinimide esters, or groups reactive against carboxyls or against an antibody's glycosylation. Any number of polymers may bind to each SBP. Specific examples of polymers that may be used include straight-chain ("X8") polymers or third-generation dendritic ("DN3") polymers, both available as MaxPar™ reagents. Use of metal nanoparticles can also be used to increase the number of atoms in a label, as also discussed above.

In some embodiments, all labelling atoms in a mass tag are of the same atomic mass. Alternatively, a mass tag can comprise labelling atoms of differing atomic mass. Accordingly, in some instances, a labelled sample may be labelled with a series of mass-tagged SBPs each of which comprises just a single type of labelling atom (wherein each SBP binds its cognate target and so each kind of mass tag is localised on the sample to a specific e.g. antigen). Alternatively, in some instance, a labelled sample may be labelled with a series of mass-tagged SBPs each of which comprises a mixture of labelling atoms. In some instances, the mass-tagged SBPs used to label the sample may comprise a mix of those with single labelling atom mass tags and mixes of labelling atoms in their mass tags.

Spacer

As noted above, in some instances, the SBP is conjugated to a mass tag through a linker which comprises a spacer. There may be a spacer between the SBP and the click chemistry reagent (e.g. between the SBP and the strained cycloalkyne (or azide); strained cycloalkene (or tetrazine); etc.). There may be a spacer between the between the mass tag and the click chemistry reagent (e.g. between the mass tag and the azide (or strained cycloalkyne); tetrazine (or strained cycloalkene); etc.). In some instances there may be a spacer both between the SNP and the click chemistry reagent, and the click chemistry reagent and the mass tag.

The spacer might be a polyethylene glycol (PEG) spacer, a poly(N-vinylpyrolide) (PVP) spacer, a polyglycerol (PG) spacer, poly(N-(2-hydroxylpropyl)methacrylamide) spacer, or a polyoxazoline (POZ, such as polymethyloxazoline, polyethyloxazoline or polypropyloxazoline) or a C5-C20 non-cyclic alkyl spacer. For example, the spacer may be a PEG spacer with 3 or more, 4 or more, 5 or more, 6 or more, 7 or more, 8 or more, 9 or more, 10 or more, 11 or more, 12 or more, 15 or more of 20 or more EG (ethylene glycol) units. The PEG linker may have from 3 to 12 EG units, from 4 to 10, or may have 4, 5, 6, 7, 8, 9, or 10 EG units. The linker may include cystamine or derivatives thereof, may include one or more disulfide groups, or may be any other suitable linker known to one of skill in the art.

Spacers may be beneficial to minimize the steric effect of the mass tag on the SBP to which is conjugated. Hydrophilic spacers, such as PEG based spacers, may also act to improve the solubility of the mass-tagged SBP and act to prevent aggregation.

SBPs

Mass cytometry, including imaging mass cytometry is based on the principle of specific binding between members of specific binding pairs. The mass tag is linked to a specific binding pair member, and this localises the mass tag to the target/analyte which is the other member of the pair. Specific binding does not require binding to just one molecular species to the exclusion of others, however. Rather it defines that the binding is not-nonspecific, i.e. not a random interaction. An example of an SBP that binds to multiple targets would therefore be an antibody which recognises an epitope that is common between a number of different proteins. Here, binding would be specific, and mediated by the CDRs of the antibody, but multiple different proteins would be detected by the antibody. The common epitopes may be naturally occurring, or the common epitope could be an artificial tag, such as a FLAG tag. Similarly, for nucleic acids, the a nucleic acid of defined sequence may not bind exclusively to a fully complementary sequence, but varying tolerances of mismatch can be introduced under the use of hybridisation conditions of a differing stringencies, as would be appreciated by one of skill in the art. Nonetheless, this hybridisation is not non-specific, because it is mediated by homology between the SBP nucleic acid and the target analyte. Similarly, ligands can bind specifically to multiple receptors, a facile example being TNFα which binds to both TNFR1 and TNFR2.

The SBP may comprise any of the following: a nucleic acid duplex; an antibody/antigen complex: a receptor/ligand pair; or an aptamer/target pair. Thus a labelling atom can be attached to a nucleic acid probe which is then contacted with a tissue sample so that the probe can hybridise to complementary nucleic acid(s) therein e.g. to form a DNA/DNA duplex, a DNA/RNA duplex, or a RNA/RNA duplex. Similarly, a labelling atom can be attached to an antibody which is then contacted with a tissue sample so that it can bind to its antigen. A labelling atom can be attached to a ligand which is then contacted with a tissue sample so that it can bind to its receptor. A labelling atom can be attached to an aptamer ligand which is then contacted with a tissue sample so that it can bind to its target. Thus, labelled SBP members can be used to detect a variety of targets in a sample, including DNA sequences, RNA sequences, proteins, sugars, lipids, or metabolites.

The mass-tagged SBP therefore can be a protein or peptide, or a polynucleotide or oligonucleotide.

Examples of protein SBPs include an antibody or antigen binding fragment thereof, a monoclonal antibody, a polyclonal antibody, a bispecific antibody, a multispecific antibody, an antibody fusion protein, scFv, antibody mimetic, avidin, streptavidin, neutravidin, biotin, or a combination thereof, wherein optionally the antibody mimetic comprises a nanobody, affibody, affilin, affimer, affitin, alphabody, anticalin, avimer, DARPin, Fynomer, kunitz domain peptide, monobody, or any combination thereof, a receptor, such as a receptor-Fc fusion, a ligand, such as a ligand-Fc fusion, a lectin, for example an agglutinin such as wheat germ agglutinin.

The peptide may be a linear peptide, or a cyclical peptide, such as a bicyclic peptide. One example of a peptide that can be used is Phalloidin.

A polynucleotide or oligonucleotide generally refers to a single- or double-stranded polymer of nucleotides containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding.

Antibody SBP Members

In a typical embodiment, the labelled SBP member is an antibody. Labelling of the antibody can be achieved through conjugation of one or more labelling atom binding molecules to the antibody, by attachment of a mass tag using e.g. NHS-amine chemistry, sulfhydryl-maleimide chemistry, or the click chemistry (such as strained alkyne and azide, strained alkyne and nitrone, strained alkene and tetrazine etc.). Antibodies which recognise cellular proteins that are useful for imaging are already widely available for IHC usage, and by using labelling atoms instead of current labelling techniques (e.g. fluorescence) these known antibodies can be readily adapted for use in methods disclosure herein, but with the benefit of increasing multiplexing capability. Antibodies can recognise targets on the cell surface or targets within a cell. Antibodies can recognise a variety of targets e.g. they can specifically recognise individual proteins, or can recognise multiple related proteins which share common epitopes, or can recognise specific post-translational modifications on proteins (e.g. to distinguish between tyrosine and phosphor-tyrosine on a protein of interest, to distinguish between lysine and acetyl-lysine, to detect ubiquitination, etc.). After binding to its target, labelling atom(s) conjugated to an antibody can be detected to reveal the location of that target in a sample.

The labelled SBP member will usually interact directly with a target SBP member in the sample. In some embodiments, however, it is possible for the labelled SBP member to interact with a target SBP member indirectly e.g. a primary antibody may bind to the target SBP member, and a labelled secondary antibody can then bind to the primary antibody, in the manner of a sandwich assay. Usually, however, the method relies on direct interactions, as this can be achieved more easily and permits higher multiplexing. In both cases, however, a sample is contacted with a SBP member which can bind to a target SBP member in the sample, and at a later stage label attached to the target SBP member is detected.

Nucleic Acid SBPs, and Labelling Methodology Modifications

RNA is another biological molecule which the methods and apparatus disclosed herein are capable of detecting in a specific, sensitive and if desired quantitative manner. In the same manner as described above for the analysis of proteins, RNAs can be detected by the use of a SBP member labelled with an elemental tag that specifically binds to the RNA (e.g. an poly nucleotide or oligonucleotide of complementary sequence as discussed above, including a locked nucleic acid (LNA) molecule of complementary sequence, a peptide nucleic acid (PNA) molecule of complementary sequence, a plasmid DNA of complementary sequence, an amplified DNA of complementary sequence, a fragment of RNA of complementary sequence and a fragment of genomic DNA of complementary sequence). RNAs include not only the mature mRNA, but also the RNA processing intermediates and nascent pre-mRNA transcripts.

In certain embodiments, both RNA and protein are detected using methods of the claimed invention.

To detect RNA, cells in biological samples as discussed herein may be prepared for analysis of RNA and protein content using the methods and apparatus described herein. In certain aspects, cells are fixed and permeabilized prior to the hybridization step. Cells may be provided as fixed and/or permeabilized. Cells may be fixed by a crosslinking fixative, such as formaldehyde, glutaraldehyde. Alternatively or in addition, cells may be fixed using a precipitating fixative, such as ethanol, methanol or acetone. Cells may be permeabilized by a detergent, such as polyethylene glycol (e.g., Triton X-100), Polyoxyethylene (20) sorbitan monolaurate (Tween-20), Saponin (a group of amphipathic glycosides), or chemicals such as methanol or acetone. In certain cases, fixation and permeabilization may be performed with the same reagent or set of reagents. Fixation and permeabilization techniques are discussed by Jamur et al. in "Permeabilization of Cell Membranes" (Methods Mol. Biol., 2010).

Detection of target nucleic acids in the cell, or "in-situ hybridization" (ISH), has previously been performed using fluorophore-tagged oligonucleotide probes. As discussed herein, mass-tagged oligonucleotides, coupled with ionization and mass spectrometry, can be used to detect target nucleic acids in the cell. Methods of in-situ hybridization are known in the art (see Zenobi et al. "Single-Cell Metabolomics: Analytical and Biological Perspectives," Science vol. 342, no. 6163, 2013). Hybridization protocols are also described in U.S. Pat. No. 5,225,326 and US Pub. No. 2010/0092972 and 2013/0164750, which are incorporated herein by reference.

Prior to hybridization, cells present in suspension or immobilized on a solid support may be fixed and permeabilized as discussed earlier. Permeabilization may allow a cell to retain target nucleic acids while permitting target hybridization nucleotides, amplification oligonucleotides, and/or mass-tagged oligonucleotides to enter the cell. The cell may be washed after any hybridization step, for example, after hybridization of target hybridization oligonucleotides to nucleic acid targets, after hybridization of amplification oligonucleotides, and/or after hybridization of mass-tagged oligonucleotides.

Cells can be in suspension for all or most of the steps of the method, for ease of handling. However, the methods are also applicable to cells in solid tissue samples (e.g., tissue sections) and/or cells immobilized on a solid support (e.g., a slide or other surface). Thus, sometimes, cells can be in suspension in the sample and during the hybridization steps. Other times, the cells are immobilized on a solid support during hybridization.

Target nucleic acids include any nucleic acid of interest and of sufficient abundance in the cell to be detected by the subject methods. Target nucleic acids may be RNAs, of which a plurality of copies exist within the cell. For example, 10 or more, 20 or more, 50 or more, 100 or more, 200 or more, 500 or more, or 1000 or more copies of the target RNA may be present in the cell. A target RNA may be a messenger NA (mRNA), ribosomal RNA (rRNA), transfer RNA (tRNA), small nuclear RNA (snRNA), small interfering RNA (siRNA), long noncoding RNA (lncRNA), or any other type of RNA known in the art. The target RNA may be 20 nucleotides or longer, 30 nucleotides or longer, 40 nucleotides or longer, 50 nucleotides or longer, 100 nucleotides or longer, 200 nucleotides or longer, 500 nucleotides or longer, 1000 nucleotides or longer, between 20 and 1000 nucleotides, between 20 and 500 nucleotides in length, between 40 and 200 nucleotides in length, and so forth.

In certain embodiments, a mass-tagged oligonucleotide may be hybridized directly to the target nucleic acid sequence. However, hybridization of additional oligonucleotides may allow for improved specificity and/or signal amplification.

In certain embodiments, two or more target hybridization oligonucleotides may be hybridized to proximal regions on the target nucleic acid, and may together provide a site for hybridization of an additional oligonucleotides in the hybridization scheme.

In certain embodiments, the mass-tagged oligonucleotide may be hybridized directly to the two or more target hybridization oligonucleotides. In other embodiments, one or more amplification oligonucleotides may be added, simultaneously or in succession, so as to hybridize the two or more target hybridization oligonucleotides and provide multiple hybridization sites to which the mass-tagged oligonucleotide can bind. The one or more amplification oligonucleotides, with or without the mass-tagged oligonucleotide, may be provided as a multimer capable of hybridizing to the two or more target hybridization oligonucleotides.

While the use of two or more target hybridization oligonucleotides improves specificity, the use of amplification oligonucleotides increases signal. Two target hybridization oligonucleotides are hybridized to a target RNA in the cell. Together, the two target hybridization oligonucleotides provide a hybridization site to which an amplification oligonucleotide can bind. Hybridization and/or subsequent washing of the amplification oligonucleotide may be performed at a temperature that allows hybridization to two proximal target hybridization oligonucleotides, but is above the melting temperature of the hybridization of the amplification oligonucleotide to just one target hybridization oligonucleotide. The first amplification oligonucleotide provides multiple hybridization sites, to which second amplification oligonucleotides can be bound, forming a branched pattern. Mass-tagged oligonucleotides may bind to multiple hybridization sites provided by the second amplification nucleotides. Together, these amplification oligonucleotides (with or without mass-tagged oligonucleotides) are referred to herein as a "multimer". Thus the term "amplification oligonucleotide" includes oligonucleotides that provides multiple copies of the same binding site to which further oligonucleotides can anneal. By increasing the number of binding sites for other oligonucleotides, the final number of labels that can be found to a target is increased. Thus, multiple labelled oligonucleotides are hybridized, indirectly, to a single target RNA. This is enables the detection of low copy number RNAs, by increasing the number of detectable atoms of the element used per RNA.

One particular method for performing this amplification comprises using the RNAscope® method from Advanced cell diagnostics, as discussed in more detail below. A further alternative is the use of a method that adapts the QuantiGene® FlowRNA method (Affymetrix eBioscience). The assay is based on oligonucleotide pair probe design with branched DNA (bDNA) signal amplification. There are more than 4,000 probes in the catalog or custom sets can be requested at no additional charge. In line with the previous paragraph, the method works by hybridization of target hybridization oligonucleotides to the target, followed by the formation of a branched structure comprising first amplification oligonucleotides (termed preamplification oligonucleotides in the QuantiGene® method) to form a stem to which multiple second amplification oligonucleotides can anneal (termed simply amplification oligonucleotides in the QuantiGene® method). Multiple mass-tagged oligonucleotides can then bind.

Another means of amplification of the RNA signal relies on the rolling circle means of amplification (RCA). There are various means why which this amplification system can be introduced into the amplification process. In a first instance, a first nucleic acid is used as the hybridisation nucleic acid wherein the first nucleic acid is circular. The first nucleic acid can be single stranded or may be double-stranded. It comprises as sequence complementary to the target RNA. Following hybridisation of the first nucleic acid to the target RNA, a primer complementary to the first nucleic acid is hybridised to the first nucleic acid, and used for primer extension using a polymerase and nucleic acids, typically exogenously added to the sample. In some instances, however, when the first nucleic acid is added to sample, it may already have the primer for extension hybridised to it. As a result of the first nucleic acid being circular, once the primer extension has completed a full round of replication, the polymerase can displace the primer and extension continues (i.e. without 5'→3' exonuclease activity), producing linked further and further chained copies of the complement of the first nucleic acid, thereby amplifying that nucleic acid sequence. Oligonucleotides comprising an elemental tag (RNA or DNA, or LNA or PNA and the like) as discussed above) may therefore be hybridised to the chained copies of the complement of the first nucleic acid. The degree of amplification of the RNA signal can therefore be controlled by the length of time allotted for the step of amplification of the circular nucleic acid.

In another application of RCA, rather than the first, e.g., oligonucleotide that hybridises to the target RNA being circular, it may be linear, and comprise a first portion with a sequence complementary to its target and a second portion which is user-chosen. A circular RCA template with sequence homologous to this second portion may then be hybridised to this the first oligonucleotide, and RCA amplification carried out as above. The use of a first, e.g., oligonucleotide having a target specific portion and user-chosen portion is that the user-chosen portion can be selected so as to be common between a variety of different probes. This is reagent-efficient because the same subsequent amplification reagents can be used in a series of reactions detecting different targets. However, as understood by the skilled person, when employing this strategy, for individual detection of specific RNAs in a multiplexed reaction, each first nucleic acid hybridising to the target RNA will need to have a unique second sequence and in turn each circular nucleic acid should contain unique sequence that can be hybridised by the labelled oligonucleotide. In this manner, signal from each target RNA can be specifically amplified and detected.

Other configurations to bring about RCA analysis will be known to the skilled person. In some instances, to prevent the first, e.g., oligonucleotide dissociating from the target during the following amplification and hybridisation steps, the first, e.g., oligonucleotide may be fixed following hybridisation (such as by formaldehyde).

Further, hybridisation chain reaction (HCR) may be used to amplify the RNA signal (see, e.g., Choi et al., 2010, Nat. Biotech, 28:1208-1210). Choi explains that an HCR amplifier consists of two nucleic acid hairpin species that do not polymerise in the absence of an initiator. Each HCR hairpin consists of an input domain with an exposed single-stranded toehold and an output domain with a single-stranded toehold hidden in the folded hairpin. Hybridization of the initiator to the input domain of one of the two hairpins opens the hairpin to expose its output domain. Hybridization of this (previously hidden) output domain to the input domain of the second hairpin opens that hairpin to expose an output domain identical in sequence to the initiator. Regeneration of the initiator sequence provides the basis for a chain reaction of alternating first and second hairpin polymerization steps leading to formation of a nicked double-stranded 'polymer'. Either or both of the first and second hairpins can be labelled with an elemental tag in the application of the methods and apparatus disclosed herein. As the amplification procedure relies on output domains of specific sequence, various discrete amplification reactions using separate sets of hairpins can be performed independently in the same process. Thus this amplification also permits amplification in multiplex analyses of numerous RNA species. As Choi notes, HCR is an isothermal triggered self-assembly process. Hence, hairpins should penetrate the sample before undergoing triggered self-assembly in situ, suggesting the potential for deep sample penetration and high signal-to-background ratios.

Hybridization may include contacting cells with one or more oligonucleotides, such as target hybridization oligonucleotides, amplification oligonucleotides, and/or mass-tagged oligonucleotides, and providing conditions under which hybridization can occur. Hybridization may be performed in a buffered solution, such as saline sodium-citrate (SCC) buffer, phosphate-buffered saline (PBS), saline-sodium phosphate-EDTA (SSPE) buffer, TNT buffer (having Tris-HCl, sodium chloride and Tween 20), or any other suitable buffer. Hybridization may be performed at a temperature around or below the melting temperature of the hybridization of the one or more oligonucleotides.

Specificity may be improved by performing one or more washes following hybridization, so as to remove unbound oligonucleotide. Increased stringency of the wash may improve specificity, but decrease overall signal. The stringency of a wash may be increased by increasing or decreasing the concentration of the wash buffer, increasing temperature, and/or increasing the duration of the wash. RNAse inhibitor may be used in any or all hybridization incubations and subsequent washes.

A first set of hybridization probes, including one or more target hybridizing oligonucleotides, amplification oligonucleotides and/or mass-tagged oligonucleotides, may be used to label a first target nucleic acid. Additional sets of hybridization probes may be used to label additional target nucleic acids. Each set of hybridization probes may be specific for a different target nucleic acid. The additional sets of hybridization probes may be designed, hybridized and washed so as to reduce or prevent hybridization between oligonucleotides of different sets. In addition, the mass-tagged oligonucleotide of each set may provide a unique signal. As such, multiple sets of oligonucleotides may be used to detect 2, 3, 5, 10, 15, 20 or more distinct nucleic acid targets.

Sometimes, the different nucleic acids detected are splice variants of a single gene. The mass-tagged oligonucleotide can be designed to hybridize (directly or indirectly through other oligonucleotides as explained below) within the sequence of the exon, to detect all transcripts containing that exon, or may be designed to bridge the splice junctions to detect specific variants (for example, if a gene had three exons, and two splice variants—exons 1-2-3 and exons 1-3—then the two could be distinguished: variant 1-2-3 could be detected specifically by hybridizing to exon 2, and variant 1-3 could be detected specifically by hybridizing across the exon 1-3 junction.

Histochemical Stains

The histochemical stain reagents having one or more intrinsic metal atoms may be combined with other reagents and methods of use as described herein. For example, histochemical stains may be colocalized (e.g., at cellular or subcellular resolution) with metal containing drugs, metal-labelled antibodies, and/or accumulated heavy metals. In certain aspects, one or more histochemical stains may be used at lower concentrations (e.g., less than half, a quarter, a tenth, etc.) from what is used for other methods of imaging (e.g., fluorescence microscopy, light microscopy, or electron microscopy).

To visualize and identify structures, a broad spectrum of histological stains and indicators are available and well characterized. The metal-containing stains have a potential to influence the acceptance of the imaging mass cytometry by pathologists. Certain metal containing stains are well known to reveal cellular components, and are suitable for use in the subject invention. Additionally, well defined stains can be used in digital image analysis providing contrast for feature recognition algorithms. These features are strategically important for the development of imaging mass cytometry.

Often, morphological structure of a tissue section can be contrasted using affinity products such as antibodies. They are expensive and require additional labelling procedure using metal-containing tags, as compared to using histochemical stains. This approach was used in pioneering works on imaging mass cytometry using antibodies labelled with available lanthanide isotopes thus depleting mass (e.g. metal) tags for functional antibodies to answer a biological question.

The subject invention expands the catalog of available isotopes including such elements as Ag, Au, Ru, W, Mo, Hf, Zr (including compounds such as Ruthenium Red used to identify mucinous stroma, Trichrome stain for identification of collagen fibers, osmium tetroxide as cell counterstain).

Silver staining is used in karyotyping. Silver nitrate stains the nucleolar organization region (NOR)-associated protein, producing a dark region wherein the silver is deposited and denoting the activity of rRNA genes within the NOR. Adaptation to IMC may require that the protocols (e.g., oxidation with potassium permanganate and a silver concentration of 1% during) be modified for use lower concentrations of silver solution, e.g., less than 0.5%, 0.01%, or 0.05% silver solution.

Autometallographic amplification techniques have evolved into an important tool in histochemistry. A number of endogenous and toxic heavy metals form sulfide or selenide nanocrystals that can be autocatalytically amplified by reaction with Ag ions. The larger Ag nanocluster can then be readily visualized by IMC. At present, robust protocols for the silver amplified detection of Zn—S/Se nanocrystals have been established as well as detection of selenium through formation of silver-selenium nanocrystals. In addition, commercially available quantum dots (detection of Cd) are also autocatalytically active and may be used as histochemical labels.

Aspects of the subject invention may include histochemical stains and their use in imaging by elemental mass spectrometry. Any histochemical stain resolvable by elemental mass spectrometry may be used in the subject invention. In certain aspects, the histochemical stain includes one or more atoms of mass greater than a cut-off of the elemental mass spectrometer used to image the sample, such as greater than 60 amu, 80 amu, 100 amu, or 120 amu. For example, the histochemical stain may include a metal tag (e.g., metal atom) as described herein. The metal atom may be chelated to the histochemical stain, or covalently bound within the chemical structure of the histochemical stain. In certain aspects, the histochemical stain may be an organic molecule. Histochemical stains may be polar, hydrophobic (e.g., lipophilic), ionic or may comprise groups with different properties. In certain aspects, a histochemical stain may comprise more than one chemical.

Histochemical stains include small molecules of less than 2000, 1500, 1000, 800, 600, 400, or 200 amu. Histochemical stains may bind to the sample through covalent or non-covalent (e.g., ionic or hydrophobic) interactions. Histochemical stains may provide contrast to resolve the morphology of the biological sample, for example, to help identify individual cells, intracellular structures, and/or extracellular structures. Intracellular structures that may be resolved by histochemical stains include cell membrane, cytoplasm, nucleus, Golgi body, ER, mitochondria, and other cellular organelles. Histochemical stains may have an affinity for a type of biological molecule, such as nucleic acids, proteins, lipids, phospholipids or carbohydrates. In certain aspects, a histochemical stain may bind a molecule other than DNA. Suitable histochemical stains also include stains that bind extracellular structures (e.g., structures of the extracellular matrix), including stroma (e.g., mucosal stroma), basement membrane, interstitial stroma, proteins such as collage or elastin, proteoglycans, non-proteoglycan polysaccharides, extracellular vesicles, fibronectin, laminin, and so forth.

In certain aspects, histochemical stains and/or metabolic probes may indicate a state of a cell or tissue. For example, histochemical stains may include vital stains such as cisplatin, eosin, and propidium iodide. Other histochemical stains may stain for hypoxia, e.g., may only bind or deposit under hypoxic conditions. Probes such as Iododeoxyuridine (IdU) or a derivative thereof, may stain for cell proliferation. In certain aspects, the histochemical stain may not indicate the state of the cell or tissue. Probes that detect cell state (e.g., viability, hypoxia and/or cell proliferation) but are administered in-vivo (e.g., to a living animal or cell culture) be used in any of the subject methods but do not qualify as histochemical stains.

Histochemical stains may have an affinity for a type of biological molecule, such as nucleic acids (e.g., DNA and/or RNA), proteins, lipids, phospholipids, carbohydrates (e.g., sugars such as mono-saccharides or di-saccharides or polyols; oligosaccharides; and/or polysaccharides such as starch or glycogen), glycoproteins, and/or glycolipids. In certain aspects the histochemical stain may be a counterstain.

The following are examples of specific histochemical stains and their use in the subject methods:

Ruthenium Red stain as a metal-containing stain for mucinous stroma detection may be used as follows: Immunostained tissue (e.g., de-paraffinized FFPE or cryosection) may be treated with 0.0001-0.5%, 0.001-0.05%, less than 0.1%, less than 0.05%, or around 0.0025% Ruthenium Red (e.g., for at least 5 minutes, at least 10 minutes, at least 30 minutes, or around 30 min at 4-42° C., or around room temperature). The biological sample may be rinsed, for example with water or a buffered solution. Tissue may then be dried before imaging by elemental mass spectrometry.

Phosphotungstic Acid (e.g., as a Trichrome stain) may be used as a metal-containing stain for collagen fibers. Tissue sections on slides (de-paraffinized FFPE or cryosection) may be fixed in Bouin's fluid (e.g., for at least 5 minutes, at least 10 minutes, at least 30 minutes, or around 30 minutes at 442° C. or around room temperature). The sections may then be treated with 0.0001%-0.01%, 0.0005%-0.005%, or around 0.001% Phosphotangstic Acid for (e.g., for at least 5 minutes, at least 10 minutes, at least 30 minutes, or around 15 minutes at 442° C. or around room temperature). Sample may then be rinsed with water and/or buffered solution, and optionally dried, prior to imaging by elemental mass spectrometry. Triichrome stain may be used at a dilution (e.g., 5 fold, 10 fold, 20 fold, 50 fold or great dilution) compared to concentrations used for imaging by light (e.g., fluorescence) microscopy.

In some embodiments, the histochemical stain is an organic molecule. In some embodiments, the second metal is covalently bound. In some embodiments, the second metal is chelated. In some embodiments, the histochemical stain specifically binds cell membrane. In some embodiments, the histochemical stain is osmium tetroxide. In some embodiments, the histochemical stain is lipophilic. In some embodiments, the histochemical stain specifically binds an extracellular structure. In some embodiments, the histochemical stain specifically binds extracellular collagen. In some embodiments, the histochemical stain is a trichrome stain comprising phosphotungstic/phosphomolybdic acid. In some embodiments, trichrome stain is used after contacting the sample with the antibody, such as at a lower concentration than would be used for optical imaging, for instance wherein the concentration is a 50 fold dilution of trichrome stain or greater.

Metal-Containing Drugs

Metals in medicine is a new and exciting field in pharmacology. Little is known about the cellular structures that are involved in transiently storing metal ions prior to their incorporation into metalloproteins, nucleic acid metal complexes or metal-containing drugs or the fate of metal ions upon protein or drug degradation. An important first step towards unravelling the regulatory mechanisms involved in trace metal transport, storage, and distribution represents the identification and quantitation of the metals, ideally in context of their native physiological environment in tissues, cells, or even at the level of individual organelles and subcellular compartments. Histological studies are typically carried out on thin sections of tissue or with cultured cells.

A number of metal-containing drugs are being used for treatment of various diseases, however not enough is known about their mechanism of action or biodistribution: cisplatin, ruthenium imidazole, metallocene-based anti-cancer agents with Mo, tungstenocenes with W, B-diketonate complexes with Hf or Zr, auranofin with Au, polyoxomolybdate drugs. Many metal complexes are used as MRI contrast agents (Gd(III) chelates). Characterization of the uptake and biodistribution of metal-based anti-cancer drugs is of critical importance for understanding and minimizing the underlying toxicity.

The atomic masses of certain metals present in drugs fall into the range of mass cytometry. Specifically, cisplatin and others with Pt complexes (iproplatin, lobplatin) are extensively used as a chemotherapeutic drug for treating a wide range of cancers. The nephrotoxicity and myelotoxicity of platinum-based anti-cancer drugs is well known. With the methods and reagents described herein, their subcellular localization within tissue sections, and colocalization with mass- (e.g. metal-) tagged antibodies and/or histochemical stains can now be examined. Chemoterepeutic drugs may be toxic to certain cells, such as proliferating cells, through direct DNA damage, inhibition of DNA damage repair pathways, radioactivity, and so forth. In certain aspects, chemotherapeutic drugs may be targeted to tumor through an antibody intermediate.

In certain aspects, the metal containing drug is a chemotherapeutic drug. Subject methods may include administering the metal containing drug to a living animal, such as an animal research model or human patient as previously described, prior to obtaining the biological sample. The biological sample may be, for example, a biopsy of cancerous tissue or primary cells. Alternatively, the metal containing drug may be added directly to the biological sample, which may be an immortalized cell line or primary cells. When the animal is a human patient, the subject methods may include adjusting a treatment regimen that includes the metal containing drug, based on detecting the distribution of the metal containing drug.

The method step of detecting the metal containing drug may include subcellular imaging of the metal containing drug by elemental mass spectrometry, and may include detecting the retention of the metal containing drug in an intracellular structure (such as membrane, cytoplasm, nucleus, Golgi body, ER, mitochondria, and other cellular organelles) and/or extracellular structure (such as including stroma, mucosal stroma, basement membrane, interstitial stroma, proteins such as collage or elastin, proteoglycans, non-proteoglycan polysaccharides, extracellular vesicles, fibronectin, laminin, and so forth).

A histochemical stain and/or mass- (e.g. metal-) tagged SBP that resolves (e.g., binds to) one or more of the above structures may be colocalized with the metal containing drug to detected retention of the drug at specific intracellular or extracellular structures. For example, a chemotherapeutic drug such as cisplatin may be colocalized with a structure such as collagen. Alternatively or in addition, the localization of the drug may be related to presence of a marker of cell viability, cell proliferation, hypoxia, DNA damage response, or immune response.

In some embodiments, the metal containing drug comprises a non-endogenous metal, such as wherein the non-endogenous metal is platinum, palladium, cerium, cadmium, silver or gold. In certain aspects, the metal containing drug is one of cisplatin, ruthenium imidazole, metallocene-based anti-cancer agents with Mo, tungstenocenes with W, B-diketonate complexes with Hf or Zr, auranofin with Au, polyoxomolybdate drugs, N-myristoyltransferase-1 inhibitor (Tris(dibenzylideneacetone) dipalladium) with Pd, or a derivative thereof. For example the drug may comprise Pt, and may be, for example, cisplatin, carboplatin, oxaliplatin, iproplatin, lobaplatin or a derivative thereof. The metal containing drug may include a non-endogenous metal, such as platinum (Pt), ruthenium (Ru), molybdenum (Mo), tungsten (W), hafnium (Hf), zirconium (Zr), gold (Au), gadolinium (Gd), palladium (Pd) or an isotope thereof. Gold compounds (Auranofin, for example) and gold nanoparticle bioconjugates for photothermal therapy against cancer can be identified in tissue sections.

Accumulated Heavy Metals

Exposure to heavy metals can occur though injection of food or water, contact through skin, or aerosol intake. Heavy metals may accumulate in soft tissues of the body, such that prolonged exposure has serious health effects. In certain aspect, the heavy metal may be accumulated in vivo, either through controlled exposure in an animal research model or though environmental exposure in a human patient. The heavy metal may be a toxic heavy metal, such as Arsenic (As), Lead (Pb), Antimony (Sb), Bismuth (Bi), Cadmium (Cd), Osmium (Os), Thallium (Tl), or Mercury (Hg).

The subject methods may be used to diagnose and/or characterize heavy metal poisoning in a human patient, determine a treatment regimen for a human patient, or characterize accumulation and/or treatment of heavy metals in an animal research model.

Samples

Certain aspects of the disclosure provide a method of analysing a biological sample, such as imaging a biological sample. Such samples can comprise a plurality of cells, a plurality of these cells can be subjected to mass cytometry, such as imaging mass cytometry (IMC) in order to provide an image of these cells in the sample. In general, the invention can be used to analyse tissue samples which are now studied by FACS or immunohistochemistry (IHC) techniques, but with the use of labelling atoms which are suitable for detection by mass spectrometry (MS) or optical emission spectrometry (OES).

Any suitable tissue sample can be used in the methods described herein. For example, the tissue can include tissue from one or more of epithelium, muscle, nerve, skin, intestine, pancreas, kidney, brain, liver, blood, bone marrow, buccal swipes, cervical swipes, or any other tissue. Other bodily fluids can be a sample too, such as ascites, lung fluid, spinal fluid, amniotic fluid, blood plasma, blood serum, extracellular fluid, exudate, faeces, urine. Cell lysates can also be analysed as can cell culture supernatants, bacterial culture and/or lysate, viral culture and or culture supernatant. The biological sample may be an immortalized cell line or primary cells obtained from a living subject. For diagnostic, prognostic or experimental (e.g., drug development) purposes the tissue can be from a tumor. In some embodiments, a sample may be from a known tissue, but it might be unknown whether the sample contains tumor cells. Imaging can reveal the presence of targets which indicate the presence of a tumor, thus facilitating diagnosis. Tissue from a tumor may comprise immune cells that are also characterized by the subject methods, and may provide insight into the tumor biology. The tissue sample may comprise formalin-fixed, paraffin-embedded (FFPE) tissue. The tissues can be obtained from any living multicellular organism, such as a mammal, an animal research model (e.g., of a particular disease, such as an immunodeficient rodent with a human tumor xenograft), or a human patient.

The tissue sample may be a section e.g. having a thickness within the range of 2-10 μm, such as between 4-6 μm. Techniques for preparing such sections are well known from the field of IHC e.g. using microtomes, including dehydration steps, fixation, embedding, permeabilization, sectioning etc. Thus, a tissue may be chemically fixed and then sections can be prepared in the desired plane. Cryosectioning or laser capture microdissection can also be used for preparing tissue samples. Samples may be permeabilised e.g. to permit of reagents for labelling of intracellular targets (see above).

The size of a tissue sample to be analysed will be similar to current IHC methods, although the maximum size will be dictated by the laser ablation apparatus, and in particular by the size of sample which can fit into its sample chamber. A size of up to 5 mm×5 mm is typical, but smaller samples (e.g. 1 mm×1 mm) are also useful (these dimensions refer to the size of the section, not its thickness).

In addition to being useful for imaging tissue samples, the disclosure can instead be used for imaging of cellular samples such as monolayers of adherent cells or of cells which are immobilised on a solid surface (as in conventional immunocytochemistry). These embodiments are particularly useful for the analysis of adherent cells that cannot be easily solubilized for cell-suspension mass cytometry. Thus, as well as being useful for enhancing current immunohistochemical analysis, the disclosure can be used to enhance immunocytochemistry.

Antibodies and/or histochemical stains, as described above, may allow monitoring of tissue state, such as cell proliferation (e.g., using the target Ki-67 or marker IdU), DNA damage response (e.g., using a marker such as γH2AX), hypoxia (e.g., using the tracer EF5, either as a metal-containing derivative or coupled to a metal-tagged EF5 specific antibody). As described below, the tissue state may be correlated with the presence and/or distribution of metal containing drugs or accumulated heavy metals.

When detecting metal-containing drugs and/or accumulated heavy metals as described below, the biological sample may be obtained from an animal subject. Specifically, the animal subject may be mammalian (e.g., rodent or human), such as an animal research model or a human patient.

Animal research models include any animal genetically engineered and/or put under conditions (e.g., xenograft of a human tumor, exposure to a carcinogen, or exposure to a toxic heavy metal) to induce a diseased state, such as cancer or heavy metal poisoning. In other embodiments, the biological sample is obtained from a human patient, such as a person having or being tested for a cancer or toxic exposure to heavy metal. In either case, the animal subject may be exposed to a chemotherapeutic drug or heavy metal prior to the biological sample being obtained from the animal subject.

Multiplexed detection of metal tags, as described herein, may be used in pulse chase type experiments. Specifically, exposing a living animal or biological sample to metal containing drugs or toxic heavy metals comprising different metal isotope of the same element at different timepoints can be used to monitor the progression of metal retention and/or clearance. In certain aspects, a treatment or change in exposure may coincide with one or more timepoints.

Labelling of the Tissue Sample

The disclosure produces samples which have been labelled with labelling atoms, for example a plurality of different labelling atoms, wherein the labelling atoms are detected by an apparatus capable of sampling specific, preferably subcellular, areas of a sample (the labelling atoms therefore represent an elemental tag). The reference to a plurality of different atoms means that more than one atomic species is used to label the sample. These atomic species can be distinguished using a mass detector (e.g. they have different m/Q ratios), such that the presence of two different labelling atoms within a plume gives rise to two different MS signals. The atomic species can also be distinguished using an optical spectrometer (e.g. different atoms have different emission spectra), such that the presence of two different labelling atoms within a plume gives rise to two different emission spectral signals.

The methods herein are suitable for the simultaneous detection of many more than two different labelling atoms, permitting multiplex label detection e.g. at least 3, 4, 5, 10, 20, 30, 32, 40, 50 or even 100 different labelling atoms. Labelling atoms can also be used in a combinatorial manner to even further increase the number of distinguishable labels, if a combination of labelling atoms can be individually resolved. Giesen et al. 2014 demonstrates the use of 32 different labelling atoms in an imaging method, but laser ablation inductively coupled plasma mass spectrometry (LA-ICP-MS) is intrinsically suitable for parallel detection of higher numbers of different atoms e.g. even over 100 different atomic species, as are the other techniques discussed herein. By labelling different targets with different labelling atoms it is possible to determine the cellular location of multiple targets in a single image.

Labelling the tissue sample generally requires that the labelling atoms are attached to one member of a specific binding pair (SBP). This labelled SBP is contacted with a tissue sample such that it can interact with the other member of the SBP (the target SBP member) if it is present, thereby localising the labelling atom to a specific location in the sample. The method of the disclosure then detects the presence of the labelling atom at this specific location and translates this information into an image in which the target SBP member is present at that location. Rare earth metals and other labelling atoms can be conjugated to SBP members by known techniques e.g. Bruckner et al. (2013; Anal. Chem. 86:585-91) describes the attachment of lanthanide atoms to oligonucleotide probes for ICP-MS detection, Gao & Yu (2007; Biosensor Bioelectronics 22:933-40) describes the use of ruthenium to label oligonucleotides, and Fluidigm Canada sells the MaxPar™ metal labelling kits which can be used to conjugate over 30 different labelling atoms to proteins (e.g., antibodies including fragments thereof).

As mentioned above, a mass tag comprising one or more labelling atoms is attached to a SBP member, and this mass-tagged SBP member is contacted with the tissue sample where it can find the target SBP member (if present), thereby forming a labelled target SBP (aka a labelled analyte). The target member can comprise any chemical structure that is suitable for attaching to a labelling atom and then for imaging according to the disclosure.

In general terms, methods of the disclosure can be based on any SBP which is already known for use in determining the location of target molecules in tissue samples (e.g. as used in IHC or fluorescence in situ hybridisation, FISH), but the SBP member which is contacted with the sample will carry a labelling atom which is detectable by a detector system as described above. Thus the disclosure can readily be implemented by using available IHC and FISH reagents, merely by modifying the labels which have previously been used e.g. to modify a FISH probe to carry a label which can be detected.

The common structure of the mass-tagged SBPs resulting from the commonality of the reaction chemistries used to conjugate the SBPs and mass tags can also have advantages in terms of ensuring that the mass tags are ionised comparably to generate elemental ions when different mass-tagged SBPs are deployed together in a multiplexed reaction. Use of a common conjugation chemistry benefits the highly multiplexed analysis uniquely offered by imaging mass cytometry, as different labelling atoms can be more easily attached to different types of SBPs, allowing for a more customizable and flexible assay design. Accordingly, the invention enables the production of labelled samples in which two or more of the mass-tagged SBP reagents have the same linkage between the mass tag and SBP components of the reagent. Accordingly, the invention provides a labelled samples in which two or more of the mass-tagged SBP reagents have the same linkage between the mass tag and SBP components of the reagent. Sometimes, at least 3, at least 4, at least 5, at least 6, at least 7, at least 8, at least 9, at least 10, at least 20, at least 30, at least 40, at least 50, or at least 100 of the mass-tagged SBPs used to stain the stained sample have the same linkage between the mass tag and SBP components of the reagents.

Target Elements and Detecting the Distribution of Mass (e.g Metal) Tags

Methods may include detecting the distribution of mass (e.g. metal) tags as described herein. In certain aspects, detecting may include constructing an image (as described further herein) that renders the spatial distribution of the mass (e.g. metal) tags.

Certain methods, kits and/or biological samples may include a plurality of mass (e.g. metal) tags, such as 3 or more, 5 or more, 10 or more, 20 or more, 30 or more, 40 or more, or 50 or more metal tags.

In summary of the above in imaging mass spectrometry, the distribution of one or more target elements (i.e., elements or elemental isotopes) may be of interest. In certain aspects, target elements are labelling atoms as described herein. On other instances, the target element may be an atom that is naturally present in the sample, e.g. the target element may be a metal that is naturally coordinated in the active site of certain enzymes. A labelling atom may be directly added to the sample alone or covalently bound to or within a biologically active molecule. In certain embodiments, labelling atoms (e.g., metal tags) may be conjugated to a member of a specific binding pair (SBP), such as an antibody (that binds to its cognate antigen), aptamer or oligonucleotide for hybridizing to a DNA or RNA target, as describe herein. Labelling atoms may be attached to an SBP by any method known in the art, including the method of the invention. In certain aspects, the labelling atoms are a metal element, such as a lanthanide or transition element or another metal tag as described herein. The metal element may have a mass greater than 60 amu, greater than 80 amu, greater than 100 amu, or greater than 120 amu. Mass spectrometers described herein may deplete elemental ions below the masses of the metal elements, so that abundant lighter elements do not create space-charge effects and/or overwhelm the mass detector.

Multiplexed Analysis

One feature of the disclosure is its ability to detect multiple (e.g. 10 or more, 20 or more, 30 or more, 40 or more or 50 or more, and even up to 100 or more) different target SBP members in a sample e.g. to detect multiple different proteins and/or multiple different nucleic acid sequences. To permit differential detection of these target SBP members their respective SBP members should carry different labelling atoms such that their signals can be distinguished. For instance, where ten different proteins are being detected, ten different antibodies (each specific for a different target protein) can be used, each of which carries a unique label, such that signals from the different antibodies can be distinguished. In some embodiments, it is desirable to use multiple different antibodies against a single target e.g. which recognise different epitopes on the same protein. Thus, a method may use more antibodies than targets due to redundancy of this type. In general, however, the disclosure will use a plurality of different labelling atoms to detect a plurality of different targets.

If more than one labelled antibody is used with the disclosure, it is preferable that the antibodies should have similar affinities for their respective antigens, as this helps to ensure that the relationship between the quantity of labelling atoms detected and the abundance of the target antigen in the tissue sample will be more consistent across different SBPs (particularly at high scanning frequencies). Similarly, it is preferable if the labelling of the various antibodies has the same efficiency, so that the antibodies each carry a comparable quantity of the labelling atom.

In some instances, the SBP may carry a fluorescent label as well as an elemental tag. Fluorescence of the sample may then be used to determine regions of the sample, e.g. a tissue section, comprising material of interest which can then be sampled for detection of labelling atoms. E.g. a fluorescent label may be conjugated to an antibody which binds to an antigen abundant on cancer cells, and any fluorescent cell may then be targeted to determine expression of other cellular proteins that are about by SBPs conjugated to labelling atoms. Where a SBP carries a fluorescent tag in addition to a mass tag, the fluorescent and mass tags may be conjugated to the SBP by different chemistries. For instance, the mass tag may be conjugated using a click chemistry reaction of the invention; and the fluorescent tag may be conjugated by the prior art maleimide chemistry to conjugate the fluorescent tag to a sulfhydryl on the SBP. Alternatively, both the fluorescent and mass tags may be conjugated to the SBP by click chemistry. If a target SBP member is located intracellularly, it will typically be necessary to permeabilize cell membranes before or during contacting of the sample with the labels. For example, when the target is a DNA sequence but the labelled SBP member cannot penetrate the membranes of live cells, the cells of the tissue sample can be fixed and permeabilised. The labelled SBP member can then enter the cell and form a SBP with the target SBP member. In this respect, known protocols for use with IHC and FISH can be utilised.

A method may be used to detect at least one intracellular target and at least one cell surface target. In some embodiments, however, the disclosure can be used to detect a plurality of cell surface targets while ignoring intracellular targets. Overall, the choice of targets will be determined by the information which is desired from the method, as the disclosure will provide an image of the locations of the chosen targets in the sample.

As described further herein, specific binding partners (i.e., affinity reagents) comprising labelling atoms may be used to stain (contact) a biological sample. Suitable specific binging partners include antibodies (including antibody fragments). Labelling atoms may be distinguishable by mass spectrometry (i.e., may have different masses). Labelling atoms may be referred to herein as mass (e.g. metal) tags when they include one or more metal atoms. Mass (e.g. metal) tags may include a polymer with a carbon backbone and a plurality of pendant groups that each bind a metal atom (i.e. metal-chelating groups loaded with a metal atom). Alternatively, or in addition, metal tags may include a metal nanoparticle. Antibodies may be tagged with a mass (e.g. metal) tag by a covalent or non-covalent interaction.

Antibody stains may be used to image proteins at cellular or subcellular resolution. Aspects of the invention include contacting the sample with one or more antibodies that specifically bind a protein expressed by cells of the biological sample, wherein the antibody is tagged with a first mass (e.g. metal) tag. For example, the sample may be contacted with 5 or more, 10 or more, 15 or more, 20 or more, 30 or more, 40 or more, 50 or more antibodies, each with a distinguishable mass (e.g. metal) tag. The sample may further be contacted with one or more histochemical stains before, during (e.g., for ease of workflow), or after (e.g., to avoid altering antigen targets of antibodies) staining the sample with antibodies. The sample may further comprise one or more metal containing drugs and/or accumulated heavy metals as described herein.

Mass- (e.g. metal-) tagged antibodies for use in the subject inventions may specifically bind a metabolic probe that does not comprise a metal (e.g., EF5). Other mass- (e.g. metal-) tagged antibodies may specifically bind a target (e.g., of epithelial tissue, stromal tissue, nucleus, etc.) of traditional stains used in fluorescence and light microscopy. Such antibodies include anti-cadherin, anti-collagen, anti-keratin, anti-EFS, anti-Histone H3 antibodies, and a number of other antibodies known in the art.

Alternatively or in addition, detecting the distribution of mass (e.g. metal) tags may include measuring the extent of colocalization of two or more mass (e.g. metal) tags (e.g., assigning a value to the degree to which mass (e.g. metal) tags occupy the same or similar location). Such analysis can be useful for identifying subcellular structures at which mass (e.g. metal) tags are accumulated, which may inform understanding of the biology of exposure to the mass (e.g. metal) tags (or chemicals containing the mass (e.g. metal) tags). In certain aspects, the detection of the spatial distribution of mass (e.g. metal) tags may be at subcellular resolution. In certain aspects, some or all of the mass (e.g. metal) tags may not be endogenous to the biological sample.

Single Cell Analysis

Methods of the disclosure include laser ablation of multiple cells in a sample, and thus plumes from multiple cells are analysed and their contents are mapped to specific locations in the sample to provide an image. In most cases a user of the method will need to localise the signals to specific cells within the sample, rather than to the sample as a whole. To achieve this, the boundaries of cells (e.g. the plasma membrane, or in some cases the cell wall) in the sample can be demarcated.

Demarcation of cellular boundaries can be achieved in various ways. For instance, a sample can be studied using conventional techniques which can demarcate cellular boundaries, such as microscopy as discussed above. When performing these methods, therefore, an analysis system comprising a camera as discussed above is particularly useful. An image of this sample can then be prepared using a method of the disclosure, and this image can be superimposed on the earlier results, thereby permitting the detected signals to be localised to specific cells. Indeed, as discussed above, in some cases the laser ablation may be directed only to a subset of cells in the sample as determined to be of interest by the use of microscopy based techniques.

To avoid the need to use multiple techniques, however, it is possible to demarcate cellular boundaries as part of the imaging method of the disclosure. Such boundary demarcation strategies are familiar from IHC and immunocytochemistry, and these approaches can be adapted by using labels which can be detected. For instance, the method can involve labelling of target molecule(s) which are known to be located at cellular boundaries, and signal from these labels can then be used for boundary demarcation. Suitable target molecules include abundant or universal markers of cell boundaries, such as members of adhesion complexes (e.g. β-catenin or E-cadherin). Some embodiments can label more than one membrane protein in order to enhance demarcation.

In addition to demarcating cell boundaries by including suitable labels, it is also possible to demarcate specific organelles in this way. For instance, antigens such as histones (e.g. H3) can be used to identify the nucleus, and it is also possible to label mitochondrial-specific antigens, cytoskeleton-specific antigens, Golgi-specific antigens, ribosome-specific antigens, etc., thereby permitting cellular ultrastructure to be analysed by methods of the disclosure.

Signals which demarcate the boundary of a cell (or an organelle) can be assessed by eye, or can be analysed by computer using image processing. Such techniques are known in the art for other imaging techniques e.g. Arce et al. (2013; *Scientific Reports* 3, article 2266) describes a segmentation scheme that uses spatial filtering to determine cell boundaries from fluorescence images, reference Ali et al. (2011; *Mach Vis Appl* 23:607-21) discloses an algorithm which determines boundaries from brightfield microscopy images, reference Pound et al. (2012; *The Plant Cell* 24:1353-61) discloses the CellSeT method to extract cell geometry from confocal microscope images, and reference Hodneland et al. (2013; *Source Code for Biology and Medicine* 8:16) discloses the CellSegm MATLAB toolbox for fluorescence microscope images. A method which is useful with the disclosure uses watershed transformation and Gaussian blurring. These image processing techniques can be used on their own, or they can be used and then checked by eye.

Once cellular boundaries have been demarcated it is possible to allocate signal from specific target molecules to individual cells. It can also be possible to quantify the amount of a target analyte(s) in an individual cell e.g. by calibrating the methods against quantitative standards.

Mass Cytometry Sample Carrier

In certain embodiments, the sample may be immobilized on a solid support (i.e. a sample carrier), to position it for imaging mass spectrometry. The mass cytometry sample carrier may be optically transparent, for example made of glass or plastic. Where the mass cytometry sample carrier is optically transparent, it enables ablation of the sample material through the support. For example, the solid support may include a tissue slide. Sometimes, the mass cytometry sample carrier will comprise features that act as reference points for use with the apparatus and methods described herein, for instance to allow the calculation of the relative position of features/regions of interest that are to be ablated or desorbed and analysed.

Reference Particles

As described herein, reference particles of known elemental or isotopic composition may be added to the sample (or the sample support) for use as a reference during detection of target elemental ions in the sample. In certain embodiments, reference particles comprise metal elements or isotopes, such as transition metals or lanthanides. For example, reference particles may comprise elements or isotopes of mass greater than 60 amu, greater than 80 amu, greater than 100 amu, or greater than 120 amu.

Target elements, such as labelling atoms, can be normalized within a sample run based on elemental ions detected from individual reference particles. For example, the subject methods may include switching between detecting elemental ions from individual reference particles and detecting only target elemental ions.

Apparatus and Techniques for Use with the Invention

In general terms, the analyser apparatus disclosed herein comprises two broadly characterised systems for performing imaging elemental mass spectrometry.

The first is a sampling and ionisation system. This system contains a sample chamber, which is the component in which the sample is placed when it is subjected to analysis. The sample chamber comprises a stage, which holds the sample (typically the sample is on a mass cytometry sample carrier, such as a microscope slide, e.g. a tissue section, a monolayer of cells or individual cells, such as where a cell suspension has been dropped onto the microscope slide, and the slide is placed on the stage). The sampling and ionisation system acts to remove material from the sample in the sample chamber (the removed material being called sample material herein) which is converted into ions, either as part of the process that causes the removal of the material from the sample or via a separate ionisation system, downstream of the sampling system.

The ionised material is then analysed by the second system which is the detector system. The detector system can take different forms depending upon the particular characteristic of the ionised sample material being determined, for example a mass detector or an optical emission detector in mass spectrometry-based and optical spectrometer-based analyser apparatus, respectively.

Thus, in operation, the sample is taken into the apparatus, is sampled to generate ionised material (sampling may generate vaporous/particular material, which is subsequently ionised by the ionisation system), and the ions of the sample material are passed into the detector system. Although the detector system can detect many ions, most of these will be ions of the atoms that naturally make up the sample. In some applications, for example analysis of minerals, such as in geological or archaeological applications, this may be sufficient.

In some cases, for example when analysing biological samples, the native element composition of the sample may not be suitably informative. This is because, typically, all proteins and nucleic acids are comprised of the same main constituent atoms, and so while it is possible to tell regions which contain protein/nucleic acid from those that do not contain such proteinaceous or nucleic acid material, it is not possible to differentiate a particular protein from all other proteins. However, by labelling the sample with atoms not present in the material being analysed under normal conditions, or at least not present in significant amounts (for example certain transition metal atoms, such as rare earth metals, see section on labelling below for further detail), specific characteristics of the sample can be determined. In common with IHC and FISH, the detectable labels can be attached to specific targets on or in the sample (such as fixed cells or a tissue sample on a slide), inter alia through the use of SBPs such as antibodies or nucleic acids targeting molecules on or in the sample. In order to detect the ionised label, the detector system is used, as it would be to detect ions from atoms naturally present in the sample. By linking the detected signals to the known positions of the sampling of the sample which gave rise to those signals it is possible to generate an image of the atoms present at each position, both the native elemental composition and any labelling atoms. In aspects where native elemental composition of the sample is depleted prior to detection, the image may only be of labelling atoms. The technique allows the analysis of many labels in parallel (also termed multiplexing), which is a great advantage in the analysis of biological samples.

Thus various types of analyser apparatus can be used in practising the disclosure, a number of which are discussed in detail below. The invention provide analysers comprising an immobilised sample according to the invention, such as immobilised to a mass cytometry sample carrier comprising a polydopamine layer and/or 3D polymer such as a 3D polymer brush (e.g., of a gel such as a hydrogel).

Analyser Apparatus Based on Mass-Detection

1. Sampling and Ionisation System a. Laser Ablation Sampling and Ionising System A laser ablation based analyser typically comprises three components. The first is a laser ablation sampling system for the generation of plumes of vaporous and particulate material from the sample for analysis. Before the atoms in the plumes of ablated sample material (including any detectable labelling atoms as discussed below) can be detected by the detector system—a mass spectrometer component (MS component; the third component), the sample must be ionised (and atomised). Accordingly, the apparatus comprises a second component which is an ionisation system that ionises the atoms to form elemental ions to enable their detection by the MS component based on mass/charge ratio (some ionisation of the sample material may occur at the point of ablation, but space charge effects result in the almost immediate neutralisation of the charges). The laser ablation sampling system is connected to the ionisation system by a transfer conduit.

Laser Ablation Sampling System

In brief summary, the components of a laser ablation sampling system include a laser source that emits a beam of laser radiation that is directed upon a sample. The sample is positioned on a stage within a chamber in the laser ablation sampling system (the sample chamber). The stage is usually a translation stage, so that the sample can be moved relative to the beam of laser radiation whereby different locations on the sample can be sampled for analysis. As discussed below in more detail, gas is flowed through the sample chamber, and the flow of gas carries away the plumes of aerosolised material generated when the laser source ablates the sample, for analysis and construction of an image of the sample based on its elemental composition (including labelling atoms such as labelling atoms from elemental tags). As explained further below, in an alternative mode of action, the laser system of the laser ablation sampling system can also be used to desorb material from the sample.

For biological samples (cells, tissues sections etc.) in particular, the sample is often heterogeneous (although heterogeneous samples are known in other fields of application of the disclosure, i.e. samples of a non-biological nature). A heterogeneous sample is a sample containing regions composed of different materials, and so some regions of the sample can ablate at lower threshold fluence at a given wavelength than the others. The factors that affect ablation thresholds are the absorbance coefficient of the material and mechanical strength of material. For biological tissues, the absorbance coefficient will have a dominant effect as it can vary with the laser radiation wavelength by several orders of magnitude. For instance, in a biological sample, when utilising nanosecond laser pulses a region that contains proteinaceous material will absorb more readily in the 200-230 nm wavelength range, while a region containing predominantly DNA will absorb more readily in the 260-280 nm wavelength range.

It is possible to conduct laser ablation at a fluence near the ablation threshold of the sample material. Ablating in this manner often improves aerosol formation which in turn can help improve the quality of the data following analysis. Often to obtain the smallest crater, to maximise the resolution of the resulting image, a Gaussian beam is employed. A cross section across a Gaussian beam records an energy density profile that has a Gaussian distribution. In that case, the fluence of the beam changes with the distance from the centre. As a result, the diameter of the ablation spot size is a function of two parameters: (i) the Gaussian beam waist ($1/e^2$), and (ii) the ratio between the fluence applied and the threshold fluence.

Thus, in order to ensure consistent removal of a reproducible quantity of material with each ablative laser pulse, and thus maximise the quality of the imaging data, it is useful to maintain a consistent ablation diameter which in turn means adjusting the ratio of the energy supplied by the laser pulse to the target to the ablation threshold energy of the material being ablated. This requirement represents a problem when ablating a heterogeneous sample where the threshold ablation energy varies across the sample, such as a biological tissue where the ratio of DNA and protein material varies, or in a geological sample, where it varies with the particular composition of the mineral in the region of the sample. To address this, more than one wavelength of laser radiation can be focused onto the same ablation location on a sample, to more effectively ablate the sample based on the composition of the sample at that location.

Laser Scanning System

The laser scanning system directs laser radiation onto the sample to be ablated. As the laser scanner is capable of redirecting the positon of laser focus on the sample much more quickly than moving the sample stage relative to a stationary laser beam (due to much lower or no inertia in the operative components of the scanning system), it enables ablation of discrete spots on the sample to be performed more quickly. This quicker speed can enable a significantly greater area to be ablated and recorded as a single pixel, or the speed of the laser spot movement can simply translate to, e.g., an increase in pixel acquisition rate, or a combination of both. In addition, the rapid change in the location of the spot onto which a pulse of laser radiation can be directed permits the ablation of arbitrary patterns, for instance so that a whole cell of non-uniform shape is ablated, by a burst of pulses/shots of laser radiation in rapid succession directed onto locations on the sample by the laser scanner system, and then ionised and detected as a single cloud of material, thus enabling single cell analysis. A similar rapid-burst technique can also be deployed in methods using desorption to remove sample material from a mass cytometry sample carrier, i.e. cell LIFTing.

To enable rapid scanning, the laser scanning system must be able to rapidly switch the position at which the laser radiation is being directed on the sample. The time taken to switch the ablating position of the laser radiation is termed the response time of the laser scanning system. The laser scanning system can direct the laser beam in at least one direction relative to the sample stage on which the sample is positioned during ablation. In some instances, the laser scanning system can direct the laser radiation in two directions relative to the sample stage. By way of example, the sample stage may be used to move the sample incrementally in the X-axis, and the laser may be swept across the sample in the Y axis.

In some instances, the laser scanning system directs the laser beam in both the X and Y axes. Accordingly, in this instance more advanced ablation patterns can be generated. For instance, when the laser scanning system can direct the laser radiation in both the X and Y axes, the sample stage may be moved at constant speed in the X axis (thereby eliminating inefficiencies associated with the inertia of the sample stage during the movement across each row other than acceleration/deceleration at the start/end of the row), while the laser scanning system directs laser radiation pulses up and down columns on the sample whilst compensating for the movement of the sample stage.

Another application is arbitrary ablation area shaping. If a high repetition rate laser is used, it is possible to deliver a burst of closely-spaced laser pulses in the same time that a nanosecond laser would deliver one pulse. By quickly adjusting the X and Y positions of the ablation spot during a burst of laser pulses, ablation craters of arbitrary shape and size (down to the diffraction limit of the light) can be created. Sometimes, the laser scanning system further comprises a second positioner capable of imparting a second relative movement of the laser beam with respect to the sample stage, wherein the first and second relative movements are not parallel, such as wherein the relative movements are orthogonal.

Laser Scanning System Components

Any component which can rapidly direct laser radiation to different locations on the sample can be used as a positioner in the laser scanning system. The various types of positioner discussed below are commercially available, and can be selected by the skilled person as appropriate for the particular application for which an apparatus is to be used, as each has inherent strengths and limitations.

Galvanometer Mirror Positioner

Galvanometer motors on the shaft of which a mirror is mounted can be used to deflect the laser radiation onto different locations on the sample. Movement can be achieved by using a stationary magnet and a moving coil, or a stationary coil and a moving magnet. The arrangement of a stationary coil and moving magnet produces quicker response times. Typically sensors are present in the motor to sense the position of the shaft and the mirror, thereby providing feedback to the controller of the motor. One galvanometer mirror can direct the laser beam within one axis, and accordingly pairs of galvanometer mirrors are used to enable direction of the beam in both X and Y axes using this technology.

Galvanometer mirror systems and components are commercially available from various manufacturers such as Thorlabs (NJ, USA), Laser2000 (UK), ScanLab (Germany), and Cambridge Technology (MA, USA).

Piezoelectric Mirror Positioners

Similarly, piezoelectric actuators on the shaft of which a mirror is mounted can be used as positioners to deflect the laser radiation onto different locations on the sample. In piezoelectric mirrors based on a tilt-tip mirror arrangement, direction of the laser radiation onto the sample in the X and Y axes is provided in a single component.

Piezoelectric mirrors are commercially available from suppliers such as Physik Instrumente (Germany).

MFAS Mirror Positioner

A third kind of positioner which is dependent on physical movement of the surface directing the laser radiation onto a sample is a MEMS (Micro-Electro Mechanical System) mirror. The micro mirror in this component can be actuated by electrostatic, electromechanic and piezoelectric effects.

MEMS mirrors are commercially available from suppliers such as Mirrorcle Technologies (CA, USA), Hamamatsu (Japan) and Preciseley Microtechnology Corporation (Canada).

Polygon Scanner

A further kind of positioner which is dependent on physical movement of the surface directing the laser radiation onto a sample is a polygon scanner. Here, a reflective polygon or multifaceted mirror spins on a mechanical axis, and every time a flat facet of the polygon is traversing the incoming beam an angular deflected scanning beam is produced. Polygon scanners are one dimensional scanners, can direct the laser beam along a scanned line (and so a secondary positioner is needed in order to introduce a second relative movement in the laser beam with respect to the sample, or the sample needs to be moved on the sample stage). In contrast to the back-and-forward motion of e.g. a galvanometer based scanner, once the end of one line of the raster scan has been reached, the beam is directed back to the position at the start of the scan row. Polygon scanners are commercially available for example from Precision Laser Scanning (AZ, USA), II-VI (PA, USA), Nidec Copal Electronics Corp (Japan) inter alia.

Electro-Optical Deflector (EOD) Positioner

Unlike the preceding types for laser scanner system component, EODs are solid state components—i.e. they comprise no moving parts. Accordingly, they do not experience mechanical inertia in deflecting laser radiation and so have very fast response times, of the order of 1 ns. They also do not suffer from wear as mechanical components do. An EOD is formed of an optically transparent material (e.g. a crystal) that has a refractive index which varies dependent on the electric field applied across it, which in turn is controlled by the application of an electric voltage over the medium. The refraction of the laser radiation is caused by the introduction of a phase delay across the cross section of the beam. To place an electric field across the EOD, electrodes are bonded to opposing sides of the optically transparent material that acts as the medium. Bonding one set of opposed electrodes generates a 1-dimensional scanning EOD. Bonding a second set of electrodes orthogonally to the first set electrodes generates a 2-dimensional (X, Y) scanner.

The deflection angle of EODs is lower than galvanometer mirrors, for instance, but by placing several EODs in sequence, the angle can be increased, if required for a given apparatus set up. Exemplary materials for the refractive medium in the EOD include Potassium Tantalate Niobate KTN ($KTa_xNb_{1-x}O_3$), $LiTaO_3$, $LiNbO_3$, $BaTiO_3$, $SrTiO_3$, SBN ($Sr_{1-x}Ba_xNb_2O_6$) and $KTiOPO_4$ with KTN displaying greater deflection angles at the same field strength.

Acousto-Optical Deflector (AOD) Positioner

This class of positioner is also a solid state component. The deflection of the component is based on propagating sound waves in an optically transparent material to induce a periodically changing refractive index. The changing refractive index occurs because of compression and rarefaction of the material (i.e. changing density) due to the sound waves propagating through the material. The periodically changing refractive index diffracts a laser beam traveling through the material by acting like an optical grating.

The AOD is generated by bonding a transducer (typically a piezoelectric element) to an acousto-optic crystal (e.g. $TeO_2$). The transducer, driven by an electrical amplifier, introduces acoustic waves into the refractive medium. At the opposite end, the crystal is typically skew cut and fitted with an acoustic absorbing material to avoid reflection of the acoustic wave back into the crystal. As the waves propagate in one direction through the crystal, this forms a 1-dimensional scanner. By placing two AODs orthogonally in series, or by bonding two transducers on orthogonal crystal faces, a 2-dimensional scanner can be generated.

Exemplary materials for use as the refractive medium of the AOD include tellurium dioxide, fused silica, crystalline quartz, sapphire, AMTIR, GaP, GaAs, InP, SF6, lithium niobate, $PbMoO_4$, arsenic trisulfide, tellurite glass, lead silicate, $Ge_{55}As_{12}S_{33}$, mercury (I) chloride, and lead (II) bromide.

Combinations of Positioners

In the preceding paragraphs, two types of laser scanning system positioners are discussed: mirror based, comprising moving parts, and solid state positioners. The former are characterised by high angles of deflection, but comparatively slow response times due to inertia. In contrast, solid state positioners have a lower deflection angle range, but much quicker response times. Accordingly, sometimes, the laser scanning system includes both mirror based and solid state components in series. This arrangement takes advantages of the strengths of both, e.g. the large range provided by the mirror-based components, but accommodating the inertia of the mirror-based components. See, for instance, Matsumoto et al., 2013 (Journal of Laser Micro/Nanoengineering 8:315:320).

Accordingly, a solid state positioner (i.e. AOD or EOD) can be used for instance to correct for errors in the mirror-based scanner components. In this case, positional sensors relating to mirror-position feedback to the solid state component, and the angle of deflection introduced into the beam of laser radiation by the solid state component can be altered appropriately to correct for positional error of the mirror-based scanner components. Laser system of the laser ablation sampling system.

The laser system can be set up to produce single or multiple (i.e. two or more) wavelengths of laser radiation. Typically, the wavelengths of laser radiation discussed refer to the wavelength which has the highest intensity (the "peak" wavelength). If the system produces different wavelengths, they can be used for different purposes, for example, for targeting different materials in a sample (by targeting here is meant that the wavelength chosen is one which is absorbed well by a material).

Where multiple wavelengths are used, at least two of the two or more wavelengths of the laser radiation can be discrete wavelengths. Thus when a first laser source emits a first wavelength of radiation that is discrete from a second wavelength of radiation, it means that no, or a very low level of radiation of the second wavelength is produced by the first laser source in a pulse of the first wavelength, for example, less than 10% of the intensity at the first wavelength, such as less than 5%, less than 4%, less than 3%, less than 2%, or less than 1%. Typically, when different wavelengths of laser radiation are produced by harmonics generation, or other non-linear frequency conversion processes, then when a specific wavelength is referred to herein, it will be understood by the skilled person that there will be some degree of variation about the specified wavelength in the spectrum produced by the laser. For example, a reference to X nm encompasses a laser producing a spectrum in the range X±10 nm, such as X±5 nm, for example X±3 nm.

Lasers

Generally, the choice of wavelength and power of the laser used for ablation of the sample can follow normal usage in cellular analysis. The laser must have sufficient fluence to cause ablation to a desired depth, without substantially ablating the mass cytometry sample carrier. A laser fluence of between 0.1-5 J/cm$^2$ is typically suitable e.g. from 3-4 J/cm$^2$ or about 3.5 J/cm$^2$, and the laser will ideally be able to generate a pulse with this fluence at a rate of 200 Hz or greater. In some instances, a single laser pulse from such a laser should be sufficient to ablate cellular material for analysis, such that the laser pulse frequency matches the frequency with which ablation plumes are generated. In general, to be a laser useful for imaging biological samples, the laser should produce a pulse with duration below 100 ns (preferably below 1 ns) which can be focused to, for example, the specific spot sizes discussed below. In some embodiments of the present invention, to take advantage of the use of the laser scanning system discussed above, the ablation rate (i.e. the rate at which the laser ablates a spot on the surface of the sample) is 200 Hz or greater, such as 500 Hz or greater, 750 Hz or greater, 1 kHz or greater, 1.5 kHz or greater, 2 kHz or greater, 2.5 kHz or greater, 3 kHz or greater, 3.5 kHz or greater, 4 kHz or greater, 4.5 kHz or greater, 5 kHz or greater, 10 kHz or greater, 100 kHz or greater, 1 MHz or greater, 10 MHz or greater, or 100 MHz or greater. Many lasers have a repetition rate in excess of the laser ablation frequency, and so appropriate components, such as pulse pickers etc. can be employed to control the rate of ablation as appropriate. Accordingly, in some embodiments, the laser repetition rate is at least 1 kHz, such as at least 10 kHz, at least 100 kHz, at least 1 MHz, at least 10 MHz, around 80 MHz, or at least 100 MHz, optionally wherein the sampling system further comprises a pulse picker, such as wherein the pulse picker is controlled by the control module that also controls the movement of the sample stage and/or the positioner(s) of the laser scanning system. In other instances, multiple closely spaced pulse bursts (for example a train of 3 closely spaced pulses) can be used to ablate one single spot. As an example a 10×10 µm area may be ablated by using 100 bursts of 3 closely spaced pulses in each spot; this can be useful for lasers which have limited ablation depth, for example femtosecond lasers, and can generate a continuous plume of ablated cellular material without losing resolution. Accordingly, in some embodiments, the laser scanning system is adapted to ablate a sample using a method in which 3 temporally close pulses are used to ablate each spot on a sample (for instance wherein the pulses are less than 1 µs apart, such as less than 1 ns, or less than 1 ps apart).

For instance, the frequency of ablation by the laser system is within the range 200 Hz-100 MHz, 200 Hz-10 MHz, 200 Hz-1 MHz, 200 Hz-100 kHz, within the range 500-50 kHz, or within the range 1 kHz-10 kHz. The ablation frequency of the laser should be matched to the scanning rate of the laser scanning system as discussed above.

At these frequencies the instrumentation must be able to analyse the ablated material rapidly enough to avoid substantial signal overlap between consecutive ablations, if it is desired to resolve each ablated plume individually (which as set out below may not necessarily be desired when firing a burst of pulses at a sample) It is preferred that the overlap between signals originating from consecutive plumes is <10% in intensity, more preferably <5%, and ideally <2%. The time required for analysis of a plume will depend on the washout time of the sample chamber (see sample chamber section below), the transit time of the plume aerosol to and through the laser ionisation system, and the time taken to analyse the ionised material. Each laser pulse can be correlated to a pixel on the image of the sample that is subsequently built up, as discussed in more detail below.

In some embodiments, the laser source comprises a laser with a nanosecond pulse duration or an ultrafast laser (pulse duration of 1 ps ($10^{-12}$ s) or quicker, such as a femtosecond laser. Ultrafast pulse durations provide a number of advantages, because they limit heat diffusion from the ablated zone, and thereby provide more precise and reliable ablation craters, as well as minimising scattering of debris from each ablation event.

In some instances a femtosecond laser is used as the laser source. A femtosecond laser is a laser which emits optical pulses with a duration below 1 ps. The generation of such short pulses often employs the technique of passive mode locking. Femtosecond lasers can be generated using a number of types of laser. Typical durations between 30 fs and 30 ps can be achieved using passively mode-locked solid-state bulk lasers. Similarly, various diode-pumped lasers, e.g. based on neodymium-doped or ytterbium-doped gain media, operate in this regime. Titanium-sapphire lasers with advanced dispersion compensation are even suitable for pulse durations below 10 fs, in extreme cases down to approximately 5 fs. The pulse repetition rate is in most cases between 10 MHz and 500 MHz, though there are low repetition rate versions with repetition rates of a few megahertz for higher pulse energies (available from e.g. Lumentum (CA, USA), Radiantis (Spain), Coherent (CA, USA)). This type of laser can come with an amplifier system which increases the pulse energy.

There are also various types of ultrafast fiber lasers, which are also in most cases passively mode-locked, typically offering pulse durations between 50 and 500 fs, and repetition rates between 10 and 100 MHz. Such lasers are commercially available from e.g. NKT Photonics (Denmark; formerly Fianium), Amplitude Systems (France), Laser-Femto (CA, USA). The pulse energy of this type of laser can also be increased by an amplifier, often in the form of an integrated fiber amplifier.

Some mode-locked diode lasers can generate pulses with femtosecond durations. Directly at the laser output, the pulse duration is usually around several hundred femtoseconds (available e.g. from Coherent (CA, USA)).

In some instances, a picosecond laser is used. Many of the types of lasers already discussed in the preceding paragraphs can also be adapted to produce pulses of picosecond range duration. The most common sources are actively or passively mode-locked solid-state bulk lasers, for example a passively mode-locked Nd-doped YAG, glass or vanadate laser. Likewise, picosecond mode-locked lasers and laser diodes are commercially available (e.g. NKT Photonics (Denmark), EKSPLA (Lithuania)).

Nanosecond pulse duration lasers (gain switched and Q switched) can also find utility in particular apparatus set ups (Coherent (CA, USA), Thorlabs (NJ, USA)).

Alternatively, a continuous wave laser may be used, externally modulated to produce nanosecond or shorter duration pulses.

Typically, the laser beam used for ablation in the laser systems discussed herein has a spot size, i.e., at the sampling location, of 100 µm or less, such as 50 µm or less, 25 µm or less, 20 µm or less, 15 µm or less, or 10 µm or less, such as about 3 µm or less, about 2 µm or less, about 1 µm or less, about 500 nm or less, about 250 nm or less. The distance referred to as spot size corresponds to the longest internal dimension of the beam, e.g. for a circular beam it is the beam diameter, for a square beam it corresponds to the length of the diagonal between opposed corners, for a quadrilateral it is the length of the longest diagonal etc. (as noted above, the diameter of a circular beam with a Gaussian distribution is defined as the distance between the points at which the fluence has decreased to $1/e^2$ times the peak fluence). As an alternative to the Gaussian beam, beam shaping and beam masking can be employed to provide the desired ablation spot. For example, in some applications, a square ablation spot with a top hat energy distribution can be useful (i.e. a beam with near uniform fluence as opposed to a Gaussian energy distribution). This arrangement reduces the dependence of the ablation spot size on the ratio between the fluence at the peak of the Gaussian energy distribution and the threshold fluence. Ablation at close to the threshold fluence provides more reliable ablation crater generation and controls debris generation. Accordingly, the laser system may comprise beam masking and/or beam shaping components, such as a diffractive optical element, arranged in a Gaussian beam to re-shame the beam and produce a laser focal spot of uniform or near-uniform fluence, such as a fluence that varies across the beam by less than ±25%, such as less than ±20%, ±15%, ±10% or less than ±5%. Sometimes, the laser beam has a square cross-sectional shape. Sometimes, the beam has a top hat energy distribution.

When used for analysis of biological samples, in order to analyse individual cells the spot size of laser beam used will depend on the size and spacing of the cells. For example, where the cells are tightly packed against one another (such as in a tissue section) one or more laser sources in the laser system can have a spot size which is no larger than these cells. This size will depend on the particular cells in a sample, but in general the laser spot will have a diameter of less than 4 μm e.g. about 3 μm or less, about 2 μm or less, about 1 μm or less, about 500 nm or less, about 250 nm or less, or between 300 nm and 1 sm. In order to analyse given cells at a subcellular resolution the system uses a laser spot size which is no larger than these cells, and more specifically uses a laser spot size which can ablate material with a subcellular resolution. Sometimes, single cell analysis can be performed using a spot size larger than the size of the cell, for example where cells are spread out on the slide, with space between the cells. Here, a larger spot size can be used and single cell characterisation achieved, because the additional ablated area around the cell of interest does not comprise additional cells. The particular spot size used can therefore be selected appropriately dependent upon the size of the cells being analysed. In biological samples, the cells will rarely all be of the same size, and so if subcellular resolution imaging is desired, the ablation spot size should be smaller than the smallest cell, if constant spot size is maintained throughout the ablation procedure. Small spot sizes can be achieved using focusing of laser beams. A laser spot diameter of 1 μm corresponds to a laser focus point (i.e. the diameter of the laser beam at the focal point of the beam) of 1 μm, but the laser focus point can vary by +20% or more due to spatial distribution of energy on the target (for instance, Gaussian beam shape) and variation in total laser energy with respect to the ablation threshold energy. Suitable objectives for focusing a laser beam include a reflecting objective, such as an objective of a Schwarzschild Cassegrain design (reverse Cassegrain). Refracting objectives can also be used, as can combination reflecting-refracting objectives. A single aspheric lens can also be used to achieve the required focusing. A solid-immersion lens or diffractive optic can also be used to focus the laser beam. Another means for controlling the spot size of the laser, which can be used alone or in combination with the above objectives is to pass the beam through an aperture prior to focusing. Different beam diameters can be achieved by passing the beam through apertures of different diameter from an array of diameters. In some instances, there is a single aperture of variable size, for example when the aperture is a diaphragm aperture. Sometimes, the diaphragm aperture is an iris diaphragm. Variation of the spot size can also be achieved through dithering of the optics. The one or more lenses and one or more apertures are positioned between the laser and the sample stage.

For completeness, the standard lasers for LA at subcellular resolution, as known in the art (e.g. [5]), are excimer or exciplex lasers. Suitable results can be obtained using an argon fluoride laser ($\lambda=193$ nm). Pulse durations of 10-15 ns with these lasers can achieve adequate ablation.

Overall, the laser pulse frequency and strength are selected in combination with the response characteristics of the MS detector to permit distinct detection of individual laser ablation plumes. In combination with using a small laser spot and a sample chamber having a short washout time, rapid and high resolution imaging is now feasible.

If the laser system emits laser radiation of two or more wavelengths, this may be achieved by the use of two or more laser sources, wherein each laser source is adapted to emit laser radiation at a wavelength that differs from the wavelength of laser radiation emitted be the other laser source(s) in the laser system.

Thus, the laser system may comprise a first laser source that emits laser radiation at a wavelength of 213 nm, and a second laser source that emits laser radiation at 266 nm (so that the first laser source ablates principally proteinaceous material, and the second ablates principally DNA material). If ablation at a third wavelength of laser radiation is desired, a third laser source is used in the laser system, and so on.

Sometimes, the laser system for emitting multiple wavelengths of laser radiation comprises a single laser source adapted to emit multiple wavelengths of laser radiation (i.e. one laser emits multiple wavelengths of laser radiation, the laser system may include further laser sources). Some laser sources emit laser radiation at a desired wavelength using wavelength conversion methods such as harmonics or sum-frequency generation, by super-continuum generation, by an optical parametric amplifier or oscillator (OPA/OPO) technique, or by a combination of several techniques, as standard in the art. For instance, an Nd-YAG laser generates laser radiation at 1064 nm wavelength, which is called its fundamental frequency. This wavelength can be converted into shorter wavelengths (when needed) by the method of harmonics generation. The $4^{th}$ harmonic of that laser radiation would be at 266 nm (1064 nm÷4) and the $5^{th}$ harmonic would be at 213 nm. Thus, the $4^{th}$ harmonic can target the optical band of high absorption for DNA material while the $5^{th}$ harmonic would target the band of high absorption for proteins. In many laser arrangements generation of the $5^{th}$ harmonic is based on the generation of the $4^{th}$ harmonic. Thus the $4^{th}$ harmonic will be already present in the laser generating the $5^{th}$ harmonics output, although often the lower harmonics (with longer wavelength) are filtered out in the laser. Removal of the appropriate filters thus enables the emission of multiple wavelengths of laser radiation. Examples of such lasers are commercially available from Coherent, Inc, RP Photonics, Lee Laser etc.

Another useful pair of harmonic frequencies is the $4^{th}$ and the $3^{rd}$ harmonics of a laser with a fundamental wavelength at around 800 nm. The $4^{th}$ and the $3^{rd}$ harmonics here would have wavelengths of 200 nm and 266 nm respectively. Examples of such lasers are commercially available (Coherent, Inc., Spectra Physics).

In some situations, where the first wavelength of laser radiation and the second wavelength of laser radiation are produced by the same laser source, the wavelengths are not produced via harmonics, but from a laser with a broad emission spectrum. The emission spectrum of the laser can be at least 10 nm, such as at least 30 nm, at least 50 nm or at least 100 nm. Multiple wavelengths of light are produced by a white light laser or a supercontinuum laser.

Laser Ablation Focal Point

To maximise the efficiency of a laser to ablate material from a sample, the sample should be at a suitable position with regard to the laser's focal point, for example at the focal point, as the focal point is where the laser beam will have the smallest diameter and so most concentrated energy. This can be achieved in a number of ways. A first way is that the sample can be moved in the axis of the laser light directed upon it (i.e. up and down the path of the laser light/towards and away from the laser source) to the desired point at which the light is of sufficient intensity to effect the desired ablation. Alternatively, or additionally, lenses can be used to move the focal point of the laser light and so its effective ability to ablate material at the location of the sample, for example by demagnification. The one or more lenses are positioned between the laser and the sample stage. A third way, which can be used alone or in combination with either or both of the two preceding ways, is to alter the position of the laser.

To assist the user of the system in placing the sample at the most suitable location for ablation of material from it, a camera can be directed at the stage holding the sample (discussed in more detail below). Accordingly, the disclosure provides a laser ablation sampling system comprising a camera directed on the sample stage. The image detected by the camera can be focused to the same point at which the laser is focused. This can be accomplished by using the same objective lens for both laser ablation and optical imaging. By bringing the focal point of two into accordance, the user can be sure that laser ablation will be most effective when the optical image is in focus. Precise movement of the stage to bring the sample into focus can be effected by use of piezo activators, as available from Physik Instrumente, Cedrattechnologies, Thorlabs and other suppliers.

In a further mode of operation, the laser ablation is directed to the sample through the mass cytometry sample carrier. In this instance, the sample support should be chosen so that it is transparent (at least partially) to the frequency of laser radiation being employed to ablate the sample. Ablation through the sample can have advantages in particular situations, because this mode of ablation can impart additional kinetic energy to the plume of material ablated from the sample, driving the ablated material further away from the surface of the sample, so facilitating the ablated material's being transported away from the sample for analysis in the detector. Likewise, desorption based methods which remove slugs of sample material can also be mediated by laser radiation which passes through the carrier. The additional kinetic energy provided to the slug of material being desorbed can assist in catapulting the slug away from the mass cytometry sample carrier, and so facilitating the slug's being entrained in the carrier gas being flowed through the sample chamber.

In order to achieve 3D-imaging of the sample, the sample, or a defined area thereof, can be ablated to a first depth, which is not completely through the sample. Following this, the same area can be ablated again to a second depth, and so on to third, fourth, etc. depths. This way a 3D image of the sample can be built up. In some instances, it may be preferred to ablate all of the area for ablation to a first depth before proceeding to ablate at the second depth. Alternatively, repeated ablation at the same spot may be performed to ablate through different depths before proceeding onto the next location in the area for ablation. In both instances, deconvolution of the resulting signals at the MS to locations and depths of the sample can be performed by the imaging software.

Laser System Optics for Multiple Modes of Operation

As a matter of routine arrangement, optical components can be used to direct laser radiation, optionally of different wavelengths, to different relative locations. Optical components can also be arranged in order to direct laser radiation, optionally of different wavelengths, onto the sample from different directions. For example one or more wavelengths can be directed onto the sample from above, and one or more wavelengths of laser radiation (optionally different wavelengths) can be directed from below (i.e. through the substrate, such as a microscope slide, which carries the sample, also termed the mass cytometry sample carrier), or indeed the same wavelength can be directed from above and/or below. This enables multiple modes of operation for the same apparatus. Accordingly, the laser system can comprise an arrangement of optical components, arranged to direct laser radiation, optionally of different wavelengths, onto the sample from different directions. Thus optical components may be arranged such that the arrangement directs laser radiation, optionally of different wavelengths, onto the sample from opposite directions. "Opposite" directions in this context is not limited to laser radiation directed perpendicularly onto the sample from above and below (which would be 1800 opposite), but includes arrangements which direct laser radiation onto the sample at angles other than perpendicular to the sample. There is no requirement for the laser radiation directed onto the sample from different directions to be parallel. Sometimes, when the sample is on a mass cytometry sample carrier, the reflector arrangement can be arranged to direct laser radiation of a first wavelength directly onto the sample and to direct laser radiation of a second wavelength to the sample through the mass cytometry sample carrier.

Directing laser radiation through the mass cytometry sample carrier to the sample can be used to ablate the sample. In some systems, however, directing the laser radiation through the carrier can be used for "LIFTing" modes of operation, as discussed below in more detail in relation to desorption based sampling systems (although as will be appreciated by one of skill in the art, ablation and LIFTing can be performed by the same apparatus, and so what is termed herein a laser ablation sampling system can also act as a desorption based sampling system). The NA (numerical aperture) of the lens used to focus the laser radiation onto the sample from the first direction may be different from the NA of the lens used to focus the laser radiation (optionally at a different wavelength) onto the sample from the second direction. The lifting operation (e.g. where laser radiation is directed through the mass cytometry sample carrier) often employs a spot size of greater diameter than when ablation is being performed.

Sample Chamber of the Laser Ablation Sampling System

The sample is placed in the sample chamber when it is subjected to laser ablation. The sample chamber comprises a stage, which holds the sample (typically the sample is on a mass cytometry sample carrier). When ablated, the material in the sample forms plumes, and the flow of gas passed through the sample chamber from a gas inlet to a gas outlet carries away the plumes of aerosolised material, including any labelling atoms that were at the ablated location. The gas carries the material to the ionisation system, which ionises the material to enable detection by the detector. The atoms, including the labelling atoms, in the sample can be distinguished by the detector and so their detection reveals the presence or absence of multiple targets in a plume and so a determination of what targets were present at the ablated locus on the sample. Accordingly, the sample chamber plays a dual role in hosting the solid sample that is analysed, but also in being the starting point of the transfer of aerosolised material to the ionisation and detection systems. This means that the gas flow through the chamber can affect how spread out the ablated plume of material becomes as it passes through the system. A measure of how spread out the ablated plume becomes is the washout time of the sample chamber. This figure is a measure of how long it takes material ablated from the sample to be carried out of the sample chamber by the gas flowing through it.

The spatial resolution of the signals generated from laser ablation (i.e. when ablation is used for imaging rather than exclusively for clearing, as discussed below) in this way depends on factors including: (i) the spot size of the laser, as signal is integrated over the total area which is ablated; and the speed with which plumes are generated versus the movement of the sample relative to the laser, and (ii) the speed at which a plume can be analysed, relative to the speed at which plumes are being generated, to avoid overlap of signal from consecutive plumes as mentioned above. Accordingly, being able to analyse a plume in the shortest time possible minimises the likelihood of plume overlap (and so in turn enables plumes to be generated more frequently), if individual analysis of plumes is desired.

Accordingly, a sample chamber with a short washout time (e.g. 100 ms or less) is advantageous for use with the apparatus and methods disclosed herein. A sample chamber with a long washout time will either limit the speed at which an image can be generated or will lead to overlap between signals originating from consecutive sample spots (e.g. Kindness et al. (2003; *Clin Chem* 49:1916-23), which had signal duration of over 10 seconds). Therefore aerosol washout time is a key limiting factor for achieving high resolution without increasing total scan time. Sample chambers with washout times of ≤100 ms are known in the art. For example, Gurevich & Hergenröder (2007; *J. Anal. At. Spectrom.,* 22:1043-1050) discloses a sample chamber with a washout time below 100 ms. A sample chamber was disclosed in Wang et al. (2013; *Anal. Chem.* 85:10107-16) (see also WO 2014/146724) which has a washout time of 30 ms or less, thereby permitting a high ablation frequency (e.g. above 20 Hz) and thus rapid analysis. Another such sample chamber is disclosed in WO 2014/127034. The sample chamber in WO 2014/127034 comprises a sample capture cell configured to be arranged operably proximate to the target, the sample capture cell including: a capture cavity having an opening formed in a surface of the capture cell, wherein the capture cavity is configured to receive, through the opening, target material ejected or generated from the laser ablation site and a guide wall exposed within the capture cavity and configured to direct a flow of the carrier gas within the capture cavity from an inlet to an outlet such that at least a portion of the target material received within the capture cavity is transferrable into the outlet as a sample. The volume of the capture cavity in the sample chamber of WO 2014/127034 is less than 1 $cm^3$ and can be below 0.005 $cm^3$. Sometimes the sample chamber has a washout time of 25 ms or less, such as 20 ms, 10 ms or less, 5 ms or less, 2 ms or less, 1 ms, less or 500 μs or less, 200 μs or less, 100 μs or less, 50 μs or less, or 25 μs or less. For example, the sample chamber may have a washout time of 10 μs or more. Typically, the sample chamber has a washout time of 5 ms or less.

For completeness, sometimes the plumes from the sample can be generated more frequently than the washout time of the sample chamber, and the resulting images will smear accordingly (e.g. if the highest possible resolution is not deemed necessary for the particular analysis being undertaken).

The sample chamber typically comprises a translation stage which holds the sample (and mass cytometry sample carrier) and moves the sample relative to the beams of laser radiation. When a mode of operation is used which requires the direction of laser radiation through the mass cytometry sample carrier to the sample, e.g. as in the lifting methods discussed herein, the stage holding the mass cytometry sample carrier should also be transparent to the laser radiation used.

Thus, the sample may be positioned on the side of the mass cytometry sample carrier (e.g., glass slide) facing the laser radiation as it is directed onto the sample, such that ablation plumes are released on, and captured from, the same side as that from which the laser radiation is directed onto the sample. Alternatively, the sample may be positioned on the side of the mass cytometry sample carrier opposite to the laser radiation as it is directed onto the sample (i.e. the laser radiation passes through the mass cytometry sample carrier before reaching the sample), and ablation plumes are released on, and captured from, the opposite side to the laser radiation.

One feature of a sample chamber, which is of particular use where specific portions in various discrete areas of sample are ablated, is a wide range of movement in which the sample can be moved in the x and y (i.e. horizontal) axes in relation to the laser (where the laser beam is directed onto the sample in the z axis), with the x and y axes being perpendicular to one another. More reliable and accurate relative positions are achieved by moving the stage within the sample chamber and keeping the laser's position fixed in the laser ablation sampling system of the apparatus. The greater the range of movement, the more distant the discrete ablated areas can be from one another. The sample is moved in relation to the laser by moving the stage on which the sample is placed. Accordingly, the sample stage can have a range of movement within the sample chamber of at least 10 mm in the x and y axes, such as 20 mm in the x and y axes, 30 mm in the x and y axes, 40 mm in the x and y axes, 50 mm in the x and y axes, such as 75 mm in the x and y axes. Sometimes, the range of movement is such that it permits the entire surface of a standard 25 mm by 75 mm microscope slide to be analysed within the chamber. Of course, to enable subcellular ablation to be achieved, in addition to a wide range of movement, the movement should be precise. Accordingly, the stage can be configured to move the sample in the x and y axes in increments of less than 10 μm, such as less than 5 μm, less than 4 μm, less than 3 μm, less than 2 μm, 1 μm, or less than 1 μm, such as less than 500 nm, less than 200 nm, less than 100 nm. For example, the stage may be configured to move the sample in increments of at least 50 nm. Precise stage movements can be in increments of about 1 μm, such as 1 μm±0.1 μm. Commercially available microscope stages can be used, for example as available from Thorlabs, Prior Scientific, and Applied Scientific Instrumentation. Alternatively, the motorised stage can be built from components, based on positioners providing the desired range of movement and suitably fine precision movement, such as the SLC-24 positioners from Smaract.

Naturally, when a sample stage in a sample chamber has a wide range of movement, the sample must be sized appropriately to accommodate the movements of the stage. Sizing of the sample chamber is therefore dependent on size of the sample to be involved, which in turn determines the size of the mobile sample stage. Exemplary sizes of sample chamber have an internal chamber of 10×10 cm, 15×15 cm or 20×20 cm. The depth of the chamber may be 3 cm, 4 cm or 5 cm. The skilled person will be able to select appropriate dimensions following the teaching herein. The internal dimensions of the sample chamber for analysing biological samples using a laser ablation sampler must be bigger than the range of movement of the sample stage, for example at least 5 mm, such as at least 10 mm. This is because if the walls of the chamber are too close to the edge of the stage, the flow of the carrier gas passing through the chamber which takes the ablated plumes of material away from the sample and into the ionisation system can become turbulent. Turbulent flow disturbs the ablated plumes, and so instead of remaining as a tight cloud of ablated material, the plume of material begins to spread out after it has been ablated and carried away to the ionisation system of the apparatus. A broader peak of the ablated material has negative effects on the data produced by the ionisation and detection systems because it leads to interference due to peak overlap, and so ultimately, less spatially resolved data, unless the rate of ablation is slowed down to such a rate that it is no longer experimentally of interest.

As noted above, the sample chamber comprises a gas inlet and a gas outlet that takes material to the ionisation system. However, it may contain further ports acting as inlets or outlets to direct the flow of gas in the chamber and/or provide a mix of gases to the chamber, as determined to be appropriate by the skilled artisan for the particular ablative process being undertaken.

Camera

In addition to identifying the most effective positioning of the sample for laser ablation, the inclusion of a camera (such as a charged coupled device image sensor based (CCD) camera or an active pixel sensor based camera), or any other light detecting means in a laser ablation sampling system enables various further analyses and techniques. A CCD is a means for detecting light and converting it into digital information that can be used to generate an image. In a CCD image sensor, there are a series of capacitors that detect light, and each capacitor represents a pixel on the determined image. These capacitors allow the conversion of incoming photons into electrical charges. The CCD is then used to read out these charges, and the recorded charges can be converted into an image. An active-pixel sensor (APS) is an image sensor consisting of an integrated circuit containing an array of pixel sensors, each pixel containing a photodetector and an active amplifier, e.g. a CMOS sensor.

A camera can be incorporated into any laser ablation sampling system discussed herein, or a secondary ion mass spectrometry (SIMS) or matrix-assisted laser desorption ionization (MALDI) system as described herein. The camera can be used to scan the sample to identify cells of particular interest or regions of particular interest (for example cells of a particular morphology), or for fluorescent probes specific for an antigen, or an intracellular or structure. In certain embodiments, the fluorescent probes are histochemical stains or antibodies that also comprise a detectable mass tag.

Once such cells have been identified, then laser pulses can be directed at these particular cells to ablate material for analysis, for example in an automated (where the system both identifies and ablates the features/regions(s), such as cells(s), of interest) or semi-automated process (where the user of the system, for example a clinical pathologist, identifies the features/regions(s) of interest, which the system then ablates in an automated fashion). This enables a significant increase in the speed at which analyses can be conducted, because instead of needing to ablate the entire sample to analyse particular cells, the cells of interest can be specifically ablated. This leads to efficiencies in methods of analysing biological samples in terms of the time taken to perform the ablation, but in particular in the time taken to interpret the data from the ablation, in terms of constructing images from it. Constructing images from the data is one of the more time-consuming parts of the imaging procedure, and therefore by minimising the data collected to the data from relevant parts of the sample, the overall speed of analysis is increased.

The camera may record the image from a confocal microscope. Confocal microscopy is a form of optical microscopy that offers a number of advantages, including the ability to reduce interference from background information (light) away from the focal plane. This happens by elimination of out-of-focus light or glare. Confocal microscopy can be used to assess unstained samples for the morphology of the cells, or whether a cell is a discrete cell or part of a clump of cells. Often, the sample is specifically labelled with fluorescent markers (such as by labelled antibodies or by labelled nucleic acids). These fluorescent makers can be used to stain specific cell populations (e.g. expressing certain genes and/or proteins) or specific morphological features on cells (such as the nucleus, or mitochondria) and when illuminated with an appropriate wavelength of light, these regions of the sample are specifically identifiable. Some systems described herein therefore can comprise a laser for exciting fluorophores in the labels used to label the sample. Alternatively, an LED light source can be used for exciting the fluorophores. Non-confocal (e.g. wide field) fluorescent microscopy can also be used to identify certain regions of the biological sample, but with lower resolution than confocal microscopy.

An alternative imaging technique is two-photon excitation microscopy (also referred to as non-linear or multiphoton microscopy). The technique commonly employs near-IR light to excite fluorophores. Two photons of IR light are absorbed for each excitation event. Scattering in the tissue is minimized by IR. Further, due to the multiphoton absorption, the background signal is strongly suppressed. The most commonly used fluorophores have excitation spectra in the 400-500 nm range, whereas the laser used to excite the two-photon fluorescence lies in near-IR range. If the fluorophore absorbs two infrared photons simultaneously, it will absorb enough energy to be raised into the excited state. The fluorophore will then emit a single photon with a wavelength that depends on the type of fluorophore used that can then be detected.

When a laser is used to excite fluorophores for fluorescence microscopy, sometimes this laser is the same laser that generates the laser light used to ablate material from the biological sample, but used at a power that is not sufficient to cause ablation of material from the sample. Sometimes the fluorophores are excited by the wavelength of light that the laser then ablates the sample with. In others, a different wavelength may be used, for example by generating different harmonics of the laser to obtain light of different wavelengths, or exploiting different harmonics generated in a harmonic generation system, discussed above, apart from the harmonics which are used to ablate the sample. For example, if the fourth and/or fifth harmonic of a Nd:YAG laser are used, the fundamental harmonic, or the second to third harmonics, could be used for fluorescence microscopy.

As an example technique combining fluorescence and laser ablation, it is possible to label the nuclei of cells in the biological sample with an antibody or nucleic acid conjugated to a fluorescent moiety. Accordingly, by exciting the fluorescent label and then observing and recording the positions of the fluorescence using a camera, it is possible to direct the ablating laser specifically to the nuclei, or to areas not including nuclear material. The division of the sample into nuclei and cytoplasmic regions will find particular application in field of cytochemistry. By using an image sensor (such as a CCD detector or an active pixel sensor, e.g. a CMOS sensor), it is possible to entirely automate the process of identifying features/regions of interest and then ablating them, by using a control module (such as a computer or a programmed chip) which correlates the location of the fluorescence with the x,y coordinates of the sample and then directs the ablation laser to that location. As part of this process the first image taken by the image sensor may have a low objective lens magnification (low numerical aperture), which permits a large area of the sample to be surveyed. Following this, a switch to an objective with a higher magnification can be used to home in on the particular features of interest that have been determined to fluoresce by higher magnification optical imaging. These features recorded to fluoresce may then be ablated by a laser. Using a lower numerical aperture lens first has the further advantage that the depth of field is increased, thus meaning features buried within the sample may be detected with greater sensitivity than screening with a higher numerical aperture lens from the outset.

In methods and systems in which fluorescent imaging is used, the emission path of fluorescent light from the sample to the camera may include one or more lenses and/or one or more optical filters. By including an optical filter adapted to pass a selected spectral bandwidth from one or more of the fluorescent labels, the system is adapted to handle chromatic aberrations associated with emissions from the fluorescent labels. Chromatic aberrations are the result of the failure of lenses to focus light of different wavelengths to the same focal point. Accordingly, by including an optical filter, the background in the optical system is reduced, and the resulting optical image is of higher resolution. A further way to minimise the amount of emitted light of undesired wavelengths that reaches the camera is to exploit chromatic aberration of lenses deliberately by using a series of lenses designed for the transmission and focus of light at the wavelength transmitted by the optical filter, akin to the system explained in WO 2005/121864.

A higher resolution optical image is advantageous in this coupling of optical techniques and laser ablation sampling, because the accuracy of the optical image then determines the precision with which the ablating laser can be directed to ablate the sample.

Accordingly, in some embodiments disclosed herein, the apparatus of the invention comprises a camera. This camera can be used on-line to identify features/areas of the sample, e.g. specific cells, which can then be ablated (or desorbed by LIFTing—see below).

In a further mode of operation combining both fluorescence analysis and laser ablation sampling, instead of analysing the entire slide for fluorescence before targeting laser ablation to those locations, it is possible to fire a pulse from the laser at a spot on the sample (at low energy so as only to excite the fluorescent moieties in the sample rather than ablate the sample) and if a fluorescent emission of expected wavelength is detected, then the sample at the spot can be ablated by firing the laser at that spot at full energy, and the resulting plume analysed by a detector as described below. This has the advantage that the rastering mode of analysis is maintained, but the speed is increased, because it is possible to pulse and test for fluorescence and obtain results immediately from the fluorescence (rather than the time taken to analyse and interpret ion data from the detector to determine if the region was of interest), again enabling only the loci of importance to be targeted for analysis. Accordingly, applying this strategy in imaging a biological sample comprising a plurality of cells, the following steps can be performed: (i) labelling a plurality of different target molecules in the sample with one or more different labelling atoms and one or more fluorescent labels, to provide a labelled sample; (ii) illuminating a known location of the sample with light to excite the one or more fluorescent labels; (iii) observing and recording whether there is fluorescence at the location; (iv) if there is fluorescence, directing laser ablation at the location, to form a plume; (v) subjecting the plume to inductively coupled plasma mass spectrometry, and (vi) repeating steps (ii)-(v) for one or more further known locations on the sample, whereby detection of labelling atoms in the plumes permits construction of an image of the sample of the areas which have been ablated.

In some instances, the sample, or the mass cytometry sample carrier, may be modified so as to contain optically detectable (e.g., by optical or fluorescent microscopy) moieties at specific locations. The fluorescent locations can then be used to positionally orient the sample in the apparatus. The use of such marker locations finds utility, for example, where the sample may have been examined visually "offline"—i.e. in a piece of apparatus other than the apparatus of the invention. Such an optical image can be marked with feature(s)/region(s) of interest, corresponding to particular cells by, say, a physician, before the optical image with the feature(s)/region(s) of interest highlighted and the sample are transferred to an apparatus according to the invention. Here, by reference to the marker locations in the annotated optical image, the apparatus of the invention can identify the corresponding fluorescent positions by use of the camera and calculate an ablative and/or desorptive (LIFTing) plan for the positions of the laser pulses accordingly. Accordingly, in some embodiments, the invention comprises an orientation controller module capable of performing the above steps.

In some instances, selection of the features/regions of interest may performed using the apparatus of the invention, based on an image of the sample taken by the camera of the apparatus of the invention.

Transfer Conduit

The transfer conduit forms a link between the laser ablation sampling system and the ionisation system, and allows the transportation of plumes of sample material, generated by the laser ablation of the sample, from the laser ablation sampling system to the ionisation system. Part (or all) of the transfer conduit may be formed, for example, by drilling through a suitable material to produce a lumen (e.g., a lumen with a circular, rectangular or other cross-section) for transit of the plume. The transfer conduit sometimes has an inner diameter in the range 0.2 mm to 3 mm. Sometimes, the internal diameter of the transfer conduit can be varied along its length. For example, the transfer conduit may be tapered at an end. A transfer conduit sometimes has a length in the range of 1 centimeter to 100 centimeters. Sometimes the length is no more than 10 centimeters (e.g., 1-10 centimeters), no more than 5 centimeters (e.g., 1-5 centimeters), or no more than 3 cm (e.g., 0.1-3 centimeters). Sometimes the transfer conduit lumen is straight along the entire distance, or nearly the entire distance, from the ablation system to the ionisation system. Other times the transfer conduit lumen is not straight for the entire distance and changes orientation. For example, the transfer conduit may make a gradual 90 degree turn. This configuration allows for the plume generated by ablation of a sample in the laser ablation sampling system to move in a vertical plane initially while the axis at the transfer conduit inlet will be pointing straight up, and move horizontally as it approaches the ionisation system (e.g. an ICP torch which is commonly oriented horizontally to take advantage of convectional cooling). The transfer conduit can be straight for a distance of least 0.1 centimeters, at least 0.5 centimeters or at least 1 centimeter from the inlet aperture though which the plume enters or is formed. In general terms, typically, the transfer conduit is adapted to minimize the time it takes to transfer material from the laser ablation sampling system to the ionisation system.

Transfer Conduit Inlet, Including Sample Cone

The transfer conduit comprises an inlet in the laser ablation sampling system (in particular within the sample chamber of the laser ablation sampling system; it therefore also represents the principal gas outlet of the sample chamber). The inlet of the transfer conduit receives sample material ablated from a sample in the laser ablation sampling system, and transfers it to the ionisation system. In some instances, the laser ablation sampling system inlet is the source of all gas flow along the transfer conduit to the ionisation system. In some instances, the laser ablation sampling system inlet that receives material from the laser ablation sampling system is an aperture in the wall of a conduit along which a second "transfer" gas is flowed (as disclosed, for example in WO2014/146724 and WO2014/147260) from a separate transfer flow inlet. In this instance, the transfer gas forms a significant proportion, and in many instances the majority of the gas flow to the ionisation system. The sample chamber of the laser ablation sampling system contains a gas inlet. Flowing gas into the chamber through this inlet creates a flow of gas out of the chamber though the inlet of the transfer conduit. This flow of gas captures plumes of ablated material, and entrains it as it into the transfer conduit (typically the laser ablation sampling system inlet of the transfer conduit is in the shape of a cone, termed herein the sample cone) and out of the sample chamber into the conduit passing above the chamber. This conduit also has gas flowing into it from the separate transfer flow inlet (left hand side of the figure, indicated by the transfer flow arrow). The component comprising the transfer flow inlet, laser ablation sampling system inlet and which begins the transfer conduit which carries the ablated sample material towards the ionisation system can also termed a flow cell (as it is in WO2014/146724 and WO2014/147260).

The transfer flow fulfils at least three roles: it flushes the plume entering the transfer conduit in the direction of the ionisation system, and prevents the plume material from contacting the side walls of the transfer conduit; it forms a "protection region" above the sample surface and ensures that the ablation is carried out under a controlled atmosphere; and it increases the flow speed in the transfer conduit. Usually, the viscosity of the capture gas is lower than the viscosity of the primary transfer gas. This helps to confine the plume of sample material in the capture gas in the center of the transfer conduit and to minimize the diffusion of the plume of sample material downstream of the laser ablation sampling system (because in the center of the flow, the transport rate is more constant and nearly flat). The gas(es) may be, for example, and without limitation, argon, xenon, helium, nitrogen, or mixtures of these. A common transfer gas is argon. Argon is particularly well-suited for stopping the diffusion of the plume before it reaches the walls of the transfer conduit (and it also assists improved instrumental sensitivity in apparatus where the ionisation system is an argon gas-based ICP). The capture gas is preferably helium. However, the capture gas may be replaced by or contain other gases, e.g., hydrogen, nitrogen, or water vapor. At 25° C., argon has a viscosity of 22.6 µPas, whereas helium has a viscosity of 19.8 µPas. Sometimes, the capture gas is helium and the transfer gas is argon.

As described in WO2014/169394, the use of a sample cone minimizes the distance between the target and the laser ablation sampling system inlet of the transfer conduit. Because of the reduced distance between the sample and the point of the cone through which the capture gas can flow cone, this leads to improved capture of sample material with less turbulence, and so reduced spreading of the plumes of ablated sample material. The inlet of the transfer conduit is therefore the aperture at the tip of the sample cone. The cone projects into the sample chamber.

An optional modification of the sample cone is to make it asymmetrical. When the cone is symmetrical, then right at the center the gas flow from all directions neutralizes, so the overall flow of gas is zero along the surface of the sample at the axis of the sample cone. By making the cone asymmetrical, a non-zero velocity along the sample surface is created, which assists in the washout of plume materials from the sample chamber of the laser ablation sampling system.

In practice, any modification of the sample cone that causes a non-zero vector gas flow along the surface of the sample at the axis of the cone may be employed. For instance, the asymmetric cone may comprise a notch or a series of notches, adapted to generate non-zero vector gas flow along the surface of the sample at the axis of the cone. The asymmetric cone may comprise an orifice in the side of the cone, adapted to generate non-zero vector gas flow along the surface of the sample at the axis of the cone. This orifice will imbalance gas flows around the cone, thereby again generating a non-zero vector gas flow along the surface of the sample at the axis of the cone at the target. The side of the cone may comprise more than one orifice and may include both one or more notches and one or more orifices. The edges of the notch(es) and/or orifice(s) are typically smoothed, rounded or chamfered in order to prevent or minimize turbulence.

Different orientations of the asymmetry of the cone will be appropriate for different situations, dependent on the choice of capture and transfer gas and flow rates thereof, and it is within the abilities of the skilled person to appropriately identify the combinations of gas and flow rate for each orientation.

All of the above adaptations may be present in a single asymmetric sample cone as use in the invention. For example, the cone may be asymmetrically truncated and formed from two different elliptical cone halves, the cone may be asymmetrically truncated and comprise one of more orifices and so on.

The sample cone is therefore adapted to capture a plume of material ablated from a sample in the laser ablation sampling system. In use, the sample cone is positioned operably proximate to the sample, e.g. by manoeuvring the sample within the laser ablation sampling system on a movable mass cytometry sample carrier tray, as described already above. As noted above, plumes of ablated sample material enter the transfer conduit through an aperture at the narrow end of the sample cone. The diameter of the aperture can be a) adjustable; b) sized to prevent perturbation to the ablated plume as it passes into the transfer conduit; and/or c) about the equal to the cross-sectional diameter of the ablated plume.

Tapered Conduits

In tubes with a smaller internal diameter, the same flow rate of gas moves at a higher speed. Accordingly, by using a tube with a smaller internal diameter, a plume of ablated sample material carried in the gas flow can be transported across a defined distance more rapidly at a given flow rate (e.g. from the laser ablation sampling system to the ionisation system in the transfer conduit). One of the key factors in how quickly an individual plume can be analysed is how much the plume has diffused during the time from its generation by ablation through to the time its component ions are detected at the mass spectrometer component of the apparatus (the transience time at the detector). Accordingly, by using a narrow transfer conduit, the time between ablation and detection is reduced, thereby meaning diffusion is decreased because there is less time in which it can occur, with the ultimate result that the transience time of each ablation plume at the detector is reduced. Lower transience times mean that more plumes can be generated and analyzed per unit time, thus producing images of higher quality and/or faster.

The taper may comprise a gradual change in the internal diameter of the transfer conduit along said portion of the length of the transfer conduit (i.e. the internal diameter of the tube were a cross section taken through it decreases along the portion from the end of the portion towards the inlet (at the laser ablation sampling system end) to the outlet (at the ionisation system end). Usually, the region of the conduit near where ablation occurs has a relatively wide internal diameter. The larger volume of the conduit before the taper facilitates the confinement of the materials generated by ablation. When the ablated particles fly off from the ablated spot they travel at high velocities. The friction in the gas slows these particles down but the plume can still spread on a sub-millimeter to a millimeter scale. Allowing for sufficient distances to the walls helps with the containment of the plume near the center of the flow.

Because the wide internal diameter section is only short (of the order of 1-2 mm), it does not contribute significantly to the overall transience time providing the plume spends more time in the longer portion of the transfer conduit with a narrower internal diameter. Thus, a larger internal diameter portion is used to capture the ablation product and a smaller internal diameter conduit is used to transport these particles rapidly to the ionisation system.

The diameter of the narrow internal diameter section is limited by the diameter corresponding to the onset of turbulence. A Reynolds number can be calculated for a round tube and a known flow. In general a Reynolds number above 4000 will indicate a turbulent flow, and thus should be avoided. A Reynolds number above 2000 will indicate a transitional flow (between non-turbulent and turbulent flow), and thus may also be desired to be avoided. For a given mass flow of gas the Reynolds number is inversely proportional to the diameter of the conduit. The internal diameter of the narrow internal diameter section of the transfer conduit commonly is narrower than 2 mm, for example narrower than 1.5 mm, narrower than 1.25 mm, narrower than 1 mm, but greater than the diameter at which a flow of helium at 4 liters per minute in the conduit has a Reynolds number greater than 4000.

Rough or even angular edges in the transitions between the constant diameter portions of the transfer conduit and the taper may cause turbulence in the gas flow, and typically are avoided.

Sacrificial Flow

At higher flows, the risk of turbulence occurring in the conduit increases. This is particularly the case where the transfer conduit has a small internal diameter (e.g. 1 mm). However, it is possible to achieve high speed transfer (up to and in excess of 300 m/s) in transfer conduits with a small internal diameter if a light gas, such as helium or hydrogen, is used instead of argon which is traditionally used as the transfer flow of gas.

High speed transfer presents problems insofar as it may cause the plumes of ablated sample material to be passed through the ionisation system without an acceptable level of ionisation occurring. The level of ionisation can drop because the increased flow of cool gas reduces the temperature of the plasma at the end of the torch. If a plume of sample material is not ionised to a suitable level, information is lost from the ablated sample material—because its components (including any labelling atoms/elemental tags) cannot be detected by the mass spectrometer. For example, the sample may pass so quickly through the plasma at the end of the torch in an ICP ionisation system that the plasma ions do not have sufficient time to act on the sample material to ionise it. This problem, caused by high flow, high speed transfer in narrow internal diameter transfer conduits can be solved by the introduction of a flow sacrificing system at the outlet of the transfer conduit. The flow sacrificing system is adapted to receive the flow of gas from the transfer conduit, and pass only a portion of that flow (the central portion of the flow comprising any plumes of ablated sample material) onwards into the injector that leads to the ionisation system. To facilitate dispersion of gas from the transfer conduit in the flow sacrificing system, the transfer conduit outlet can be flared out.

The flow sacrificing system is positioned close to the ionisation system, so that the length of the tube (e.g. injector) that leads from the flow sacrificing system to the ionisation system is short (e.g. ~1 cm long; compared to the length of the transfer conduit which is usually of a length of the order of tens of cm, such as ~50 cm). Thus the lower gas velocity within the tube leading from the flow sacrificing system to the ionisation system does not significantly affect the total transfer time, as the relatively slower portion of the overall transport system is much shorter.

In most arrangements, it is not desirable, or in some cases possible, to significantly increase the diameter of the tube (e.g. the injector) which passes from the flow sacrificing system to the ionisation system as a way of reducing the speed of the gas at a volumetric flow rate. For example, where the ionisation system is an ICP, the conduit from the flow sacrificing system forms the injector tube in the center of the ICP torch. When a wider internal diameter injector is used, there is a reduction in signal quality, because the plumes of ablated sample material cannot be injected so precisely into the center of the plasma (which is the hottest and so the most efficiently ionising part of the plasma). The strong preference is for injectors of 1 mm internal diameter, or even narrower (e.g. an internal diameter of 800 μm or less, such as 600 μm or less, 500 μm or less or 400 μm or less). Other ionisation techniques rely on the material to be ionised within a relatively small volume in three dimensional space (because the necessary energy density for ionisation can only be achieved in a small volume), and so a conduit with a wider internal diameter means that much of the sample material passing through the conduit is outside of the zone in which energy density is sufficient to ionise the sample material. Thus narrow diameter tubes from the flow sacrificing system into the ionisation system are also employed in apparatus with non-ICP ionisation systems. As noted above, if a plume of sample material is not ionised to a suitable level, information is lost from the ablated sample material—because its components (including any labelling atoms/elemental tags) cannot be detected by the mass spectrometer.

Pumping can be used to help ensure a desired split ratio between the sacrificial flow and the flow passing into the inlet of the ionisation system. Accordingly, sometimes, the flow sacrificing system comprises a pump attached to the sacrificial flow outlet. A controlled restrictor can be added to the pump to control the sacrificial flow. Sometimes, the flow sacrificing system also comprises a mass flow controller, adapted to control the restrictor.

Where expensive gases are used, the gas pumped out of the sacrificial flow outlet can be cleaned up and recycled back into the same system using known methods of gas purification. Helium is particularly suited as a transport gas as noted above, but it is expensive; thus, it is advantageous to reduce the loss of helium in the system (i.e. when it is passed into the ionisation system and ionised). Accordingly, sometimes a gas purification system is connected to the sacrificial flow outlet of the flow sacrificing system.

Ionisation System

In order to generate elemental ions, it is necessary to use a hard ionisation technique that is capable of vaporising, atomising and ionising the atomised sample.

Inductively Coupled Plasma Torch

Commonly, an inductively coupled plasma is used to ionise the material to be analysed before it is passed to the mass detector for analysis. It is a plasma source in which the energy is supplied by electric currents produced by electromagnetic induction. The inductively coupled plasma is sustained in a torch that consists of three concentric tubes, the innermost tube being known as the injector.

The induction coil that provides the electromagnetic energy that maintains the plasma is located around the output end of the torch. The alternating electromagnetic field reverses polarity many millions of times per second. Argon gas is supplied between the two outermost concentric tubes. Free electrons are introduced through an electrical discharge and are then accelerated in the alternating electromagnetic field whereupon they collide with the argon atoms and ionise them. At steady state, the plasma consists of mostly of argon atoms with a small fraction of free electrons and argon ions.

The ICP can be retained in the torch because the flow of gas between the two outermost tubes keeps the plasma away from the walls of the torch. A second flow of argon introduced between the injector (the central tube) and the intermediate tube keeps the plasma clear of the injector. A third flow of gas is introduced into the injector in the centre of the torch. Samples to be analysed are introduced through the injector into the plasma.

The ICP can comprise an injector with an internal diameter of less than 2 mm and more than 250 µm for introducing material from the sample into the plasma. The diameter of the injector refers to the internal diameter of the injector at the end proximal to the plasma. Extending away from the plasma, the injector may be of a different diameter, for example a wider diameter, wherein the difference in diameter is achieved through a stepped increase in diameter or because the injector is tapered along its length. For instance, the internal diameter of the injector can be between 1.75 mm and 250 µm, such as between 1.5 mm and 300 µm in diameter, between 1.25 mm and 300 µm in diameter, between 1 mm and 300 µm in diameter, between 900 µm and 300 µm in diameter, between 900 µm and 400 µm in diameter, for example around 850 µm in diameter. The use of an injector with an internal diameter less than 2 mm provides significant advantages over injectors with a larger diameter. One advantage of this feature is that the transience of the signal detected in the mass detector when a plume of sample material is introduced into the plasma is reduced with a narrower injector (the plume of sample material being the cloud of particular and vaporous material removed from the sample by the laser ablation sampling system). Accordingly, the time taken to analyse a plume of sample material from its introduction into the ICP for ionisation until the detection of the resulting ions in the mass detector is reduced. This decrease in time taken to analyse a plume of sample material enables more plumes of sample material to be detected in any given time period. Also, an injector with a smaller internal diameter results in the more accurate introduction of sample material into the centre of the induction coupled plasma, where more efficient ionisation occurs (in contrast to a larger diameter injector which could introduce sample material more towards the fringe of the plasma, where ionisation is not as efficient).

ICP torches (Agilent, Varian, Nu Instruments, Spectro, Leeman Labs, PerkinElmer, Thermo Fisher etc.) and injectors (for example from Elemental Scientific and Meinhard) are available.

Other Ionisation Techniques

Electron Ionisation

Electron ionisation involves bombarding a gas-phase sample with a beam of electrons. An electron ionisation chamber includes a source of electrons and an electron trap. A typical source of the beam of electrons is a rhenium or tungsten wire, usually operated at 70 electron volts energy. Electron beam sources for electron ionisation are available from Markes International. The beam of electrons is directed towards the electron trap, and a magnetic field applied parallel to the direction of the electrons travel causes the electrons to travel in a helical path. The gas-phase sample is directed through the electron ionisation chamber and interacts with the beam of electrons to form ions. Electron ionisation is considered a hard method of ionisation since the process typically causes the sample molecules to fragment. Examples of commercially available electron ionisation systems include the Advanced Markus Electron Ionisation Chamber.

Optional Further Components of the Laser Ablation Based Sampling and Ionisation System Ion Deflector Mass spectrometers detect ions when they hit a surface of their detector. The collision of an ion with the detector causes the release of electrons from the detector surface. These electrons are multiplied as they pass through the detector (the first released electron knocks out further electrons in the detector, these electrons then hit secondary plates which further amplify the number of electrons). The number of electrons hitting the anode of the detector generates a current. The number of electrons hitting the anode can be controlled by altering the voltage applied to the secondary plates. The current is an analog signal that can then be convened into a count of the ions hitting the detector by an analog-digital converter. When the detector is operating in its linear range, the current can be directly correlated to the number of ions. The quantity of ions that can be detected at once has a limit (which can be expressed as the number of ions detectable per second). Above this point, the number electrons released by ions hitting the detector is no longer correlated to the number of ions. This therefore places an upper limit on the quantitative capabilities of the detector.

When ions hit the detector, its surface becomes damaged by contamination. Over time, this irreversible contamination damage results in fewer electrons being released by the detector surface when an ion hits the detector, with the ultimate result that the detector needs replacing. This is termed "detector aging", and is a well-known phenomenon in MS.

Detector life can therefore be lengthened by avoiding the introduction of overloading quantities of ions into the MS. As noted above, when the total number of ions hitting the MS detector exceeds the upper limit of detection, the signal is not as informative as when the number of ions is below the upper limit because it is no longer quantitative. It is therefore desirable to avoid exceeding the upper limit of detection as it results in accelerated detector aging without generating useful data.

Analysis of large packets of ions by mass spectrometry involves a particular set of challenges not found in normal mass spectrometry. In particular, typical MS techniques involve introducing a low and constant level of material into the detector, which should not approach the upper detection limit or cause accelerated aging of the detector. On the other hand, laser ablation- and desorption-based techniques analyse a relatively large amount of material in a very short time window in the MS: e.g. the ions from a cell-sized patch of a tissue sample which is much larger than the small packets of ions typically analysed in MS. In effect, it is a deliberate almost overloading of the detector with analysed packed of ions resulting from ablation or lifting. In between the analysis events the signal is at baseline (a signal that is close to zero because no ions from labelling atoms are deliberately being entering into the MS from the sampling and ionisation system; some ions will inevitably be detected because the MS is not a complete vacuum).

Thus in apparatus described herein, there is an elevated risk of accelerated detector aging, because the ions from packets of ionised sample material labelled with a large number of detectable atoms can exceed the upper limit of detection and damage the detector without providing useful data.

To address these issues, the apparatus can comprise an ion deflector positioned between the sampling and ionisation system and the detector system (a mass spectrometer), operable to control the entry of ions into the mass spectrometer. In one arrangement, when the ion deflector is on, the ions received from the sampling and ionisation system are deflected (i.e. the path of the ions is changed and so they do not reach the detector), but when the deflector is off the ions are not deflected and reach the detector. How the ion deflector is deployed will depend on the arrangement of the sampling and ionisation system and MS of the apparatus. E.g. if the portal through which the ions enter the MS is not directly in line with the path of ions exiting the sampling and ionisation system, then by default the appropriately arranged ion deflector will be on, in order to direct ions from the sampling and ionisation system into the MS. When an event resulting from the ionisation a packet of ionised sample material considered likely to overload the MS is detected (see below), the ion deflector is switched off, so that the rest of the ionised material from the event is not deflected into the MS and can instead simply hit an internal surface of the system, thereby preserving the life of the MS detector. The ion deflector is returned to its original state after the ions from the damaging event have been prevented from entering the MS, thereby allowing the ions from subsequent packets of ionised sample material to enter the MS and be detected.

Alternatively, in arrangements where (under normal operating conditions) there is no change in the direction of the ions emerging from the sampling and ionisation system before they enter the MS the ion deflector will be off, and the ions from the sampling and ionisation system will pass through it to be analysed in the MS. To prevent damage when a potential overload of the detector is detected, in this configuration the ion deflector is turned on, and so diverts ions so that they do not enter the detector in order to prevent damage to the detector.

The ions entering the MS from ionisation of sample material (such as a plume of material generated by laser ablation or desorption) do not enter the MS all at the same time, but instead enter as a peak with a frequency that follows a probability distribution curve about a maximum frequency: from baseline, at first a small number of ions enters the MS and are detected, and then the frequency of ions increases to a maximum before the number decreases again and trails off to baseline. An event likely to damage the detector can be identified because instead of a slow increase in the frequency of ions at the leading edge of the peak, there is a very quick increase in counts of ions hitting the detector.

The flow of ions hitting the detector of a TOF MS, a particular type of detector as discussed below, is not continual during the analysis of the ions in a packet of ionised sample material. The TOF comprises a pulser which releases the ions periodically into the flight chamber of the TOF MS in pulsed groups. By releasing the ions all at the known same time, the time of flight mass determination is enabled. The time between the releases of pulses of ions for time of flight mass determination is known as an extraction or push of the TOF MS. The push is in the order of microseconds. The signal from one or more packets of ions from the sampling and ionisation system therefore covers a number of pushes.

Accordingly, when the ion count reading jumps from the baseline to a very high count within one push (i.e. the first portion of the ions from a particular packet of ionised sample material) then it can be predicted that the main body of ions resulting from ionisation of the packet of sample material will be even greater, and so exceed the upper detection limit. It is at this point that an ion deflector can be operated to ensure that the damaging bulk of the ions are directed away from the detector (by being activated or deactivated, depending on the arrangement of the system, as discussed above).

Suitable ion deflectors based on quadrupoles are available in the art (e.g. from Colutron Research Corporation and Dreebit GmbH).

b. Desorption Based Sampling and Ionising System

A desorption based analyser typically comprises three components. The first is a desorption system for the generation of slugs of sample material from the sample for analysis. Before the atoms in the slugs of desorbed sample material (including any detectable labelling atoms as discussed below) can be detected, the sample must be ionised (and atomised). Accordingly, the apparatus comprises a second component which is an ionisation system that ionises the atoms to form elemental ions to enable their detection by the MS detector component (third component) based on mass/charge ratio. The desorption based sampling system and the ionisation system are connected by a transfer conduit. In many instances the desorption based sampling system is also a laser ablation based sampling system.

Desorption Sampling System

Figure 8:
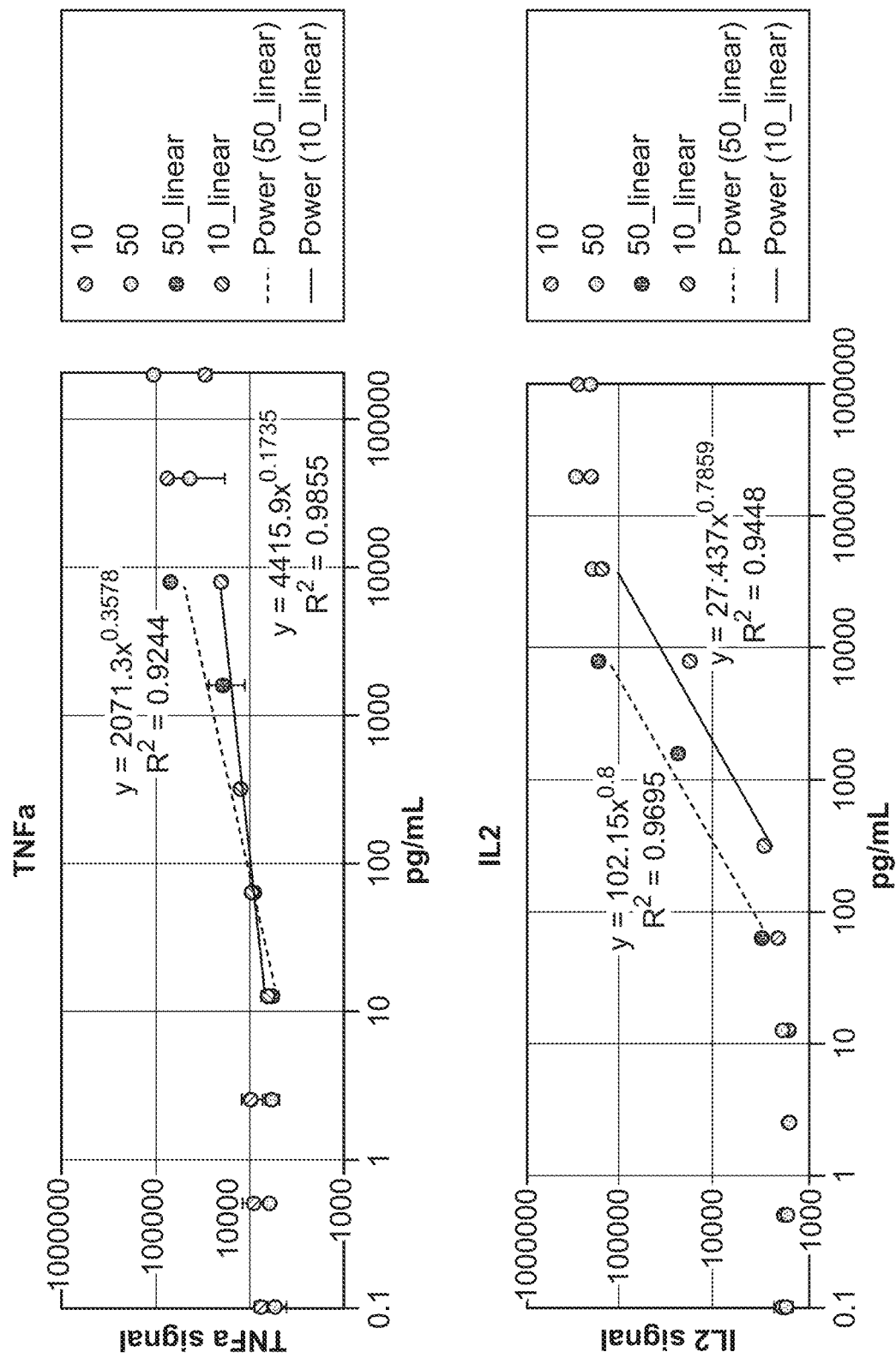
FIG. 8. Graph of the mass signal and concentration for both TNF-α and IL-2 according to embodiments of the present invention.

In some instances, rather than laser ablation being used to generate a particulate and/or vaporised plume of sample material, a bulk mass of sample material is desorbed from the mass cytometry sample carrier on which it is located without substantial disintegration of the sample and its conversion into small particles and/or vaporisation (see e.g. FIG. 8 of WO2016109825, and the accompanying description, which are herein incorporated by reference). Herein, the term slug is used to refer to this desorbed material (one particular form of a packet of sample material discussed herein). The slug can have dimensions from 10 nm to 10 µm, from 100 nm to 10 µm, and in certain instances from 1 µm to 100 µm. This process can be termed sample catapulting. Commonly, the slug represents a single cell (in which case the process can be termed cell catapulting).

The slug of sample material released from the sample can be a portion of the sample which has been cut into individual slugs for desorption prior to the desorption step, optionally in a process prior to the sample being inserted into the apparatus. A sample divided into discrete slugs prior to analysis is called a structured sample. Each of these individual slugs therefore represents a discrete portion of the sample that can be desorbed, ionised and analysed in the apparatus. By analysis of slugs from the discrete sites, an image can be built up with each slug representing a pixel of the image, in the same way that each location of a sample ablated by the laser ablation sampling system described above.

A structured sample may be prepared by various methods. For instance, a mass cytometry sample carrier comprising topographic features configured to cut a biological sample may be used. Here, a biological sample is applied onto the surface of the carrier, which causes the topographic features to cut and section the sample, in turn causing the sections of biological material to be retained by the plurality of discrete sites between the features to provide a structured biological sample. Alternatively, the mass cytometry sample carrier may not comprise such topographical features (in effect, a flat surface like a microscope slide, optionally functionalised as discussed below), in which case the sample may be applied to the mass cytometry sample carrier and the sample may be sectioned to define slugs of sample that can be desorbed for ionisation and analysis. The sectioning of the sample can be accomplished by mechanical tools such as blades or stamps, if the sample is a tissue section. Alternatively, the material around the sections of the sample to be desorbed can be removed by laser ablation in the same or a separate sample preparation setup. In certain techniques, the material can be removed by a setup employing a focused electron or ion beam. The focused electron or ion beam can lead to particularly narrow cuts (potentially on the 10 nm scale) between subsections leading to a pixel size on the order of 1 µm or in certain instances, 100 nm.

The slugs of sample material can be released from the carrier and each discrete portion of sample material sequentially introduced into the detector for analysis as a discrete event (generating a pixel of an image by the techniques discussed below). The benefits of sequential introduction of discrete material as opposed to random introduction of biological samples as in conventional mass cytometry or mass spectrometry include a higher sample processing rate. This is because the slug is transported from the sample chamber to the ionisation system as preferably a single piece of matter, and so cannot spread out as a plume of ablated material would in a flow of gas (in particular a gas flow in which there is some turbulence).

Desorption for Sampling

Sample material can be desorbed from the sample by thermal energy, mechanical energy, kinetic energy, and a combination of any of the foregoing. This kind of sampling is useful in particular in analysing biological samples.

In certain instances, sample material may be released from the sample by thermal mechanisms. For example, the surface of mass cytometry sample carrier becomes sufficiently hot to desorb a slug of sample material. The mass cytometry sample carrier may be coated to facilitate the bulk desorption process, for example with polyethylene naphthalate (PEN) polymer or PMMA polymer film. Heat can be provided by a radiative source such as a laser (such as the laser of a laser ablation sampling system discussed above). The energy applied to the surface should be sufficient to desorb the biological material, preferably without altering the sample material if it is from a biological sample. Any suitable radiation wavelength can be used, which can depend in part on the absorptive properties of the mass cytometry sample carrier. A surface or layer of the mass cytometry sample carrier may be coated with or include an absorber that absorbs laser radiation for conversion to heat. The radiation may be delivered to a surface of the carrier other than the surface on which the sample is located, or it may be delivered to the surface carrying the sample, such as through the thickness of the carrier. The heated surface may be a surface layer or may be an inner layer of a multilayer structure of the mass cytometry sample carrier. One example of the use of laser radiation energy is in a technique called lifting (laser induced forward transfer; see e.g. Doraiswamy et al., 2006, Applied Surface Science, 52: 4743-4747; Fernández-Pradas, 2004, Thin Solid Films 453-454: 27-30; Kyrkis et al., in Recent Advances in Laser Processing of Materials, Eds. Perriere et al., 2006, Elsivier), in which the mass cytometry sample carrier may comprise a desorption film layer. The desorption film can absorb the radiation to cause release of the desorption film and/or the biological sample (e.g. in some instances the sample film desorbs from the mass cytometry sample carrier together with the biological sample, in other instances, the film remains attached to the mass cytometry sample carrier, and the biological sample desorbs from the desorption film).

Desorption by heating can take place on a nanosecond, picosecond or femtosecond time scale, depending on the laser used for desorption.

The sample can be desorbed by the action of a layer of an electrical conductor that heats up upon the application of a current. In such the sites from which sample material is desorbed are electrically connected to electrodes and the sites are individually addressable.

A sample may be attached to the mass cytometry sample carrier by a cleavable photoreactive moiety. Upon irradiating the cleavable photoreactive moiety with radiation (e.g. from a laser in the laser system of the laser ablation sampling system), the photoreactive moiety can cleave to release sample material. The mass cytometry sample carrier may comprise (i) a cleavable photoreactive moiety that couples the sample to the mass cytometry sample carrier and (ii) a desorption film as discussed above. In this situation, a first laser radiation pulse may be used to cause cleavage of the photoreactive moiety and a second laser radiation pulse may be used to target the desorption film to cause separation of the sample from the mass cytometry sample carrier by lifting (or a thermal energy pulse introduced by other means may be used to heat the desorption film and so cause separation of sample material from the mass cytometry sample carrier). The first and second pulses may be of different wavelengths. Thus in some methods (e.g. comprising both ablation and desorption), separation of the sample from the mass cytometry sample carrier may involve multiple laser pulses of different wavelengths. In some instances, cleavage of the photoreactive moiety and lifting may be accomplished by the same laser pulse.

The mass cytometry sample carrier may include a coating or layer of a chemically reactive species that imparts kinetic energy to the sample to release the sample from the surface. For example, a chemically reactive species may release a gas such as, for example, $H_2$, $CO_2$, $N_2$ or hydrochlorofluorocarbons. Examples of such compounds include blowing and foaming agents, which release gas upon heating. Generation of gas can be used to impart kinetic energy to desorbing sample material that can improve the reproducibility and direction of release of the material.

A mass cytometry sample carrier may comprise photoinitiated chemical reactants that undergo an exothermic reaction to generate heat for desorbing sample material. The coating of the carrier, or indeed particular chemical linkages in that carrier, discussed in the above paragraphs (that is irradiated by the laser to release the slug of sample material from the carrier) is an example of a material that can be targeted by a wavelength of laser radiation.

The sites on the mass cytometry sample carrier from which slugs of sample material are to be desorbed may be mounted and/or coupled to MEMS devices configured to facilitate release of a biological material from the discrete sites on a carrier.

A slug of the sample can be released or desorbed from a discrete site using nano-heaters, bubble jets, piezoelectrics, ultrasonics, electrostatics, or a combination of any of the foregoing.

Each, or a combination, of these techniques permits ordered detachment of a slug of sample material from the mass cytometry sample carrier. However, often, the location on the sample that is of interest does not represent a discrete entity, such as a lone cell, at a discrete site which can be easily desorbed in isolation. Instead, the cell of interest may be surrounded by other cells or material, of which analysis is not required or desired. Trying to perform desorption (e.g. lifting) of the feature/region of interest may therefore desorb both the cell of interest and surrounding material together. Atoms, such as labelling atoms which are used in elemental tags (see discussion below), from the surrounding area of the sample (e.g. from other cells which have been labelled) that are carried in a desorbed slug of material in addition to the specific feature/region (e.g. cell) of interest could therefore contaminate the reading for the location of interest.

The techniques of ablation and desorption (such as by lifting) can be combined in a single method. For example, to perform precise desorption of a feature/region (e.g. cell) of interest on a biological sample, e.g. a tissue section sample or cell suspension dispersion, on the mass cytometry sample carrier, laser ablation can be used to ablate the area around the cell of interest to clear it of other material. After clearing the surrounding area by ablation, the feature/region of interest can then be desorbed from the mass cytometry sample carrier, and then ionised and analyzed by mass spectrometry in line with standard mass cytometry or mass spectrometry procedures. In line with the above discussion, thermal, photolytic, chemical, or physical techniques can be used to desorb material from a feature/region of interest, optionally after ablation has been used to clear the area surrounding the location that will be desorbed. Often, lifting will be employed, to separate the slug of material from the mass cytometry sample carrier (e.g. a mass cytometry sample carrier which has been coated with a desorption film to assist the lifting procedure, as discussed above with regard to desorption of discrete slugs of sample material).

The feature/region of interest can be identified by another technique before the laser ablation and desorption (e.g. by lifting) is performed. The inclusion of a camera (such as a charged coupled device image sensor based (CCD) camera or a CMOS camera or an active pixel sensor based camera), or any other light detecting means as described in the preceding sections is one way of enabling these techniques, for both online and offline analyses. The camera can be used to scan the sample to identify cells of particular interest or features/regions of particular interest (for example cells of a particular morphology). Once such locations have been identified, the locations can be lifted after laser pulses have been directed at the area around the feature/region of interest to clear other material by ablation before the location (e.g. cell) is lifted. This process may be automated (where the system both identifies, ablates and lifts the feature(s)/region(s) of interest) or semi-automated process (where the user of the system, for example a clinical pathologist, identifies the feature(s)/region(s) of interest, following which the system then performs ablation and lifting in an automated fashion). This enables a significant increase in the speed at which analyses can be conducted, because instead of needing to ablate the entire sample to analyze particular cells, the cells of interest can be specifically ablated.

The camera can record the image from a microscope (e.g. a confocal microscope). The identification may be by light microscopy, for example by examining cell morphology or cell size, or on whether the cell is a discrete single cell (in contrast to a member of a clump of cells). Sometimes, the sample can be specifically labelled to identify the feature(s) (e.g. cell(s)) of interest. Often, fluorescent markers are used to specifically stain the cells of interest (such as by using labelled antibodies or labelled nucleic acids), as discussed above in relation to methods of ablating visually-identified features/regions of interest; that section is not repeated here in full in the interests of brevity, but one of skill in the art will immediately appreciate that the features of those methods can be applied to desorption based methods and that this is within the technical teaching of this document. A high resolution optical image is advantageous in this coupling of optical techniques and lifting, because the accuracy of the optical image then determines the precision with which the ablating laser source can be directed to ablate the area surrounding the cell of interest which can subsequently be ablated.

Sometimes, no data are recorded from the ablation performed to clear the area around the location to be desorbed (e.g. the cell of interest). Sometimes, data is recorded from the ablation of the surrounding area. Useful information that can be obtained from the surrounding area includes what target molecules, such as proteins and RNA transcripts, are present in the surrounding cells and intercellular milieu. This may be of particular interest when imaging solid tissue samples, where direct cell-cell interactions are common, and what proteins etc. are expressed in the surrounding cells may be informative on the state of the cell of interest.

Camera

The camera used in the desorption based sampling system can be as described above for the laser ablation based sampling system, and the discussion for the camera of the laser ablation based sampling system should be read in here.

Sample Chamber

The sample chamber used in the desorption based sampling system can be as described above for the laser ablation based sampling system. In instances where sampling of large slugs of sample material is being undertaken, the skilled practitioner will appreciate that gas flow volumes may need to be increased to ensure that the slug of material is entrained in the flow of gas and carried into the transfer conduit for transport to the ionisation system.

Transfer Conduit

The sample chamber used in the desorption based sampling system can be as described above for the laser ablation based sampling system. In instances where sampling of large slugs of sample material is being undertaken, the skilled practitioner will appreciate that the diameter of the lumen of the conduit will need to be appropriately sized to accommodate any slugs without the slug contacting the side of the lumen (because any contact may lead to fragmentation of the slug, and to the overlapping of signals—where atoms from the slug resulting the nth desorption event are spread into the detection window for the n+1th or subsequent slugs).

Ionisation System of the Desorption Based System

In many instances, the lifting techniques discussed above involve the removal of relatively large slugs of sample material (10 nm to 10 µm, from 100 nm to 10 µm, and in certain instances from 1 µm to 100 µm) which have not been converted into particulate and vaporous material. Accordingly, an ionisation technique which is capable of vaporising and atomising this relatively large quantity of material is required.

Inductively Coupled Plasma Torch

One such suitable ionisation system is an inductively coupled plasma, as already discussed above in the section beginning on page 120 in relation to laser ablation based sampling and ionisation systems.

Optional Further Components of the Desorption Based Sampling and Ionisation System Ion Deflector The ion deflector used in the desorption based sampling system can be as described above for the laser ablation based sampling system. Given the potential for desorption based sampling to remove intact large slugs of sample material, ion deflectors can be particularly useful in this kind of system for protecting the detector.

c. Laser Desorption/Ionisation Systems

A laser desorption/ionisation based analyser typically comprises two components. The first is a system for the generation of ions from the sample for analysis. In this apparatus, this is achieved by directing a laser beam onto the sample to generate ions; herein it is called a laser desorption ion generation system. These ejected sample ions (including any detectable ions from labelling atoms as discussed below) can be detected by a detector system (the second component) for instance a mass spectrometer (detectors are discussed in more detail below). This technique is known as laser desorption/ionisation mass spectrometry (LDI-MS). LDI is different from the desorption based sampling systems discussed in more detail below, because in the desorption based sampling system the sample material is desorbed as charge neutral slugs of material which are subsequently ionised to form elemental ions. On the contrary, here, ions are produced directly as a result of irradiation of the sample by the laser and no separate ionisation system is required.

The laser desorption ion generation system comprises: a laser; a sample chamber for housing the sample onto which radiation from the laser is directed; and ion optics that take ions generated from the sample and direct them to the detector for analysis. Accordingly, the invention provides an apparatus for analysing a sample comprising: a. a sample chamber to house the sample; b. a laser, adapted to desorb and ionize material from the sample, forming ions; c ion optics, arranged to sample the ions formed by desorption ionisation, and to direct them away from sample towards the detector; and d. a detector to receive ions from said ion optics and to analyse said ions. In some embodiments, the apparatus comprises a laser adapted to desorb and ionize material from the sample, forming elemental ions, and wherein the detector receives the elemental ions from said sampling and ionisation system and analyses said elemental ions.

In this process some molecules reach an energy level at which they desorb from the sample and become ionised. The ions may arise as primary ions directly as a result of the laser irradiation or as secondary ions, formed by collision of charge neutral species with the primary ions (e.g. proton transfer, cationization and electron capture). In some instances, ionisation is assisted by compounds (e.g. a matrix) added to the sample as the sample is being prepared, as discussed below.

Laser

A variety of different lasers can be used for LDI, including commercial lasers as discussed above in relation to the laser of the laser ablation sampling system, adapted as appropriate to enable desorption of ions. Accordingly, in some embodiments, the apparatus comprises a laser adapted to desorb and ionize material from the sample, forming elemental ions, and wherein the detector receives the elemental ions from said sampling and ionisation system and is adapted to analyse said elemental ions. Sometimes, the apparatus comprises a laser adapted to desorb and ionize material from the sample, forming molecular ions, and wherein the detector receives the molecular ions from said sampling and ionisation system and is adapted to detect said molecular ions. In other instances, the apparatus comprises a laser adapted to desorb and ionize material from the sample, forming both elemental and molecular ions, and wherein the detector receives the ions from said sampling and ionisation system and is adapted to detect both said elemental and said molecular ions.

Exemplary lasers include those which emit at 193 nm, 213 nm or 266 nm (deep UV lasers that can cause release of ions from the sample without requiring a matrix to promote ionization, as in MALDI). Desorption of ions representing lichen metabolites following laser irradiation of a sample is demonstrated in Le Pogam et al., 2016 (Scientific Reports 6, Article number: 37807) at 355 nm.

Femtosecond lasers as discussed above are also advantageous in particular LDI applications.

For rapid analysis of a sample a high frequency of ablation is needed, for example more than 200 Hz (i.e. more than 200 laser shots per second, giving more than 200 clouds of ions per second). Commonly, the frequency of ion cloud generation by the laser system is at least 400 Hz, such as at least 500 Hz, at least 1 kHz, at least 10 kHz, at least 100 kHz or at least 1 MHz. For instance, the frequency of ablation by the laser system is within the range 200 Hz-1 MHz, within the range 500 Hz-100 kHz, within the range 1-10 kHz.

As explained above in relation to laser ablation sampling systems, the laser radiation can be directed to the sample via various optical components, and focused to a spot size (i.e. size of the beam of laser radiation when it hits the sample) of 100 µm or less, such as 50 µm or less, 25 µm or less, 20 µm or less, 15 µm or less, or 10 µm or 1 um or less. When used for analysis of biological samples, including tissue sections, in order to analyse individual cells the spot size of laser beam used will depend on the size and spacing of the cells. For example, where the cells are tightly packed against one another (such as in a tissue section) the laser spot can have a spot size which is no larger than these cells if single cell analysis is to be conducted. This size will depend on the particular cells in a sample, but in general the laser spot for LDI will have a diameter of less than 4 µm e.g. within the range 0.1-4 µm, 0.25-3 µm, or 0.4-2 µm. In order to analyse cells at a subcellular resolution the LDI system uses a laser spot size which is no larger than these cells, and more specifically uses a laser beam spot size which can ablate material with a subcellular resolution. Sometimes, single cell analysis can be performed using a spot size larger than the size of the cell, for example where cells are spread out on the slide, with space between the cells. The particular spot size used can therefore be selected appropriately dependent upon the size of the cells being analysed. In biological samples, the cells will rarely all be of the same size, and so if subcellular resolution imaging is desired, the laser spot size should be smaller than the smallest cell, if constant spot size is maintained throughout the ion generation procedure.

Sometimes the laser can comprise a laser scanner as discussed above in relation to laser ablation sampling.

Sample Chamber

The sample chamber of the LDI system shares many features in common with the sample chamber of the laser ablation-based and desorption-based sampling systems discussed above. It comprises a stage to support the sample. The stage may be a translation stage, movable in the x-y or x-y-z axes. The sample chamber will also comprise an outlet, through which material removed from the sample by the laser radiation can be directed. The outlet is connected to the detector, enabling analysis of the sample ions.

The sample chamber can be at atmospheric pressure. LDI (in particular MALDI) at atmospheric pressure is known. Here, the ions produced by LDI are assisted in their transfer from ionisation to the high vacuum region for analysis (e.g. MS dectector) by a pneumatic stream of gas, for instance nitrogen (Laiko et al., 2000. Anal. Chem., 72:652-657).

In some instances, the sample chamber is held under a vacuum, or a partial vacuum. Accordingly, in some instances, the sample chamber pressure is lower than 50 000 Pa, lower than 10 000 Pa, lower than 5 000 Pa, lower than 1 000 Pa, lower than 500 Pa, lower than 100 Pa, lower than 10 Pa, lower than 1 Pa, around 0.1 Pa or less than 0.1 Pa, such as 0.01 Pa or lower. For instance, partial vacuum pressure may be around 200-700 Pa, and vacuum pressure 0.2 Pa or lower.

The selection of whether the sample pressure is at atmospheric pressure under a (partial) vacuum depends on the particular analysis being performed, as will be understood by one of skill in the art. For instance, at atmospheric pressure, sample handing is easier, and softer ionisation may be applied. Further, the presence of gas molecules may be desired so as to enable the phenomenon of collisional cooling to occur, which can be of interest when the label is a large molecule, the fragmentation of which is not desired, e.g. a molecular fragment comprising a labelling atom or combination thereof.

Holding the sample chamber under vacuum can prevent collisions between sample ions generated by LDI and other particles within the chamber. This, in some instances, may be preferred because collisions with gas molecules in the chamber may result in loss of charge from the generated sample ions. Loss of charge from the sample ions would result in their not being detected by the apparatus.

In some embodiments, the sample chamber comprises one or more gas ports arranged to enable delivery of one or more flows of gas to locations of laser desorption/ionisation on the sample during laser desorption/ionisation, such as wherein one or more gas ports is in the form of a nozzle. The gas ports (e.g. nozzle) are operable to deliver gas at the moment of desorption and ionisation, to provide collisional cooling for the desorbed ions, but only at that particular time. The rest of the time, they do not introduce gas into the chamber, thus reducing strain on the vacuum pump.

Ion Optics

The sample ion beams are captured from the sample via electrostatic plates positioned near to the sample, known in the art as the extraction electrode(s). The extraction electrode(s) remove(s) the sample ions desorbed by laser ablation from the locality of the sample. This is typically achieved by the sample, situated on a plate which also acts and an electrode (the sample electrode), and the extraction electrode(s) having a large difference in voltage potential. Depending on the polarity of the sample vis-à-vis the extraction electrodes, positively or negatively charged secondary ions are captured by the extraction electrodes.

In some embodiments, the charge across the electrodes is constant during laser desorption/ionisation. Sometimes, the charge is varied following the desorption/ionization, for instance delayed extraction, in which the accelerating voltage is applied after some short time delay following desorption/ionisation induced by a laser pulse. This technique produces time-of-flight compensation for ion energy spread, where ions with greater kinetic energy would move with greater velocity from the sample towards the detector than those with lower kinetic energy. Accordingly, this difference in velocity can cause lower resolution at the detector, because not all ions are moving at the same velocity. Accordingly, by delaying the application of the voltage across the sample and extraction electrodes, those ions with lower kinetic energy with have remained closer to the sample electrode when the accelerating voltage is applied and therefore start being accelerated at a greater potential compared to the ions farther from the target electrode. With the proper delay time, the slower ions are accelerated sufficiently to catch the ions that had higher kinetic energy after laser desorption/ionization after flying some distance from the pulsed acceleration system. Ions of the same mass-to-charge ratio will then drift through the flight tube to the detector in the same time. Accordingly, in some embodiments the sample and extraction electrodes are controllable to apply a charge across the electrodes at a set time following the laser short causing desorption/ionization of the sample.

The sample ions are then transferred to the detector via one or more further electrostatic lenses (known as transfer lenses in the art). The transfer lens(es) focus(es) the beam of sample ions into the detector. Typically, in systems with multiple transfer lenses, only one transfer lens is engaged in a given analysis. Each lens may provide a different magnification of the sample surface. Commonly, further ion manipulation components are present between the electrodes and the detector, for example one or more apertures, mass filters or sets of deflector plates. Together, the electrodes, transfer lens, and any further components, form the ion optics. Components for the production of an appropriate ion optics arrangement are available from commercial suppliers e.g. Agilent, Waters, Bruker, and can be positioned appropriately by one of skilled in the art, to deliver the ions to a detector as discussed herein below.

In addition to the detectors discussed below, as LDI can be performed so that it results in soft ionisation (e.g.

ionisation without breaking of bonds in the molecules being analysed), in some instances, the detector may be a tandem MS, in which a first m/z separation is performed to select ions from the sample, before the selected ions are broken down into their fragments and undergo a second m/z separation whereupon the fragments are detected.

Methods Employing LDI

The invention also provides methods for analysing biological samples using LDI. In this analysis, the cells are labelled with labels, and these labels are then detected in the ions produced following LDI of the samples. Accordingly, the invention provides a method for performing mass cytometry on a sample comprising a plurality of cells, comprising: a. labelling a plurality of different target molecules in the sample with one or more different labels, to provide a labelled sample; b. performing laser desorption/ionisation of the sample, wherein laser desorption/ionisation is performed at multiple known locations to form a plurality of individual ion clouds; and c. subjecting the ion clouds individually to mass spectrometry, whereby detection of labels in the plumes permits construction of an image of the sample.

In some embodiments, the one or more labels comprise labelling atoms. In this instance, labelling works as described below herein, whereby a member of a specific binding pair (e.g. antibody binding to a protein antigen, or a nucleic acid binding to a RNA in the sample) is attached to an elemental tag comprising one or more labelling atoms (e.g. lanthanides and actinides). The elemental tag can comprise just a single type of labelling atom (e.g. one or more atoms of a single isotope of a particular element), or can comprise different multiple kinds of labelling atom (e.g. different elements/isotopes) thereby enabling large numbers of different tags to be generated as the specific combination elements/isotopes acts as the label. In some instances, the labelling atom is detected as an elemental ion. In some embodiments, the labelling atom is emitted from the sample within a molecular ion. Thus, instead of the detection in the mass channel for the labelling atom, the presence of the labelled material in the sample will be detected in the mass channel for the molecular ion (i.e. the mass channel will simply be shifted by the mass of the molecule minus the labelling atom, vis-à-vis the labelling atom alone). In some embodiments, however, the molecule that contains the labelling atom may vary between different labelling atoms. In that case the ion containing molecular residue and labelling atom will be subjected to a fragmentation method that yields a more consistent mass peak for each reagent, such as through the application of tandem MS. The goal of all these variations and modifications to the main LDI imaging mass cytometry scheme is to maximize the number of available mass channels while simultaneously reducing the overlap between mass channels.

In some embodiments, the staining reagents can be designed to promote the release and ionization of mass tagging material and individual elemental ions or molecular ions containing a single copy of the labelling atom. The staining reagent can also be designed to promote the release and ionization of mass tagging material and individual elemental ions or molecular ions containing a several copies of the labelling atom (or combinations thereof, as discussed above). As a further alternative, the mass of the staining reagent itself can be utilized to create a detection channel for mass cytometry. In this instance, no rare-earth isotopes will be used in the staining and the mass of the staining reagent will be varied by changing the chemistry of the staining reagents to create a number of mass channels. This variation can be done with carbon, oxygen, nitrogen, sulphur, phosphorus, hydrogen and similar isotopes without the need for the rare-earth isotopes.

In some embodiments, the sample is also treated with a laser radiation absorber composition. This composition acts to enhance absorption of laser light by the sample when irradiated, and so increases transfer of energy to excite the labelling atoms (and so promote production of elemental ions or molecular ions containing a labelling atom or combination thereof).

Numbered Embodiments Relating to the LDI Aspect of the Invention

An apparatus for analysing a sample comprising, a. a sample chamber to house the sample; b. a laser, adapted to desorb and ionize material from the sample, forming ions; c. ion optics, arranged to sample the ions formed by desorption ionisation, and to direct them away from sample towards the detector; and d. a detector to receive ions from said ion optics and to analyse said ions.

The apparatus of embodiment 1, wherein the apparatus comprises a laser adapted to desorb and ionize material from the sample, forming elemental ions, and wherein the detector receives the elemental ions from said sampling and ionisation system and is adapted to analyse said elemental ions.

The apparatus of any preceding embodiment, wherein the apparatus comprises a laser adapted to desorb and ionize material from the sample, forming molecular ions, and wherein the detector receives the molecular ions from said sampling and ionisation system and is adapted to detect said molecular ions.

The apparatus of any preceding embodiment, wherein the apparatus comprises a laser adapted to desorb and ionize material from the sample, forming both elemental and molecular ions, and wherein the detector receives the ions from said sampling and ionisation system and is adapted to detect both said elemental and said molecular ions.

The apparatus of any preceding embodiment, wherein the laser is a deep UV laser, such as a laser emitting radiation at 193 nm, 213 nm or 266 nm.

The apparatus of any preceding embodiment wherein the laser is a femtosecond laser.

The apparatus of any preceding embodiment, wherein desorption ionisation occurs in the sample chamber under a vacuum, a partial vacuum or at atmospheric pressure.

The apparatus of any preceding embodiment, wherein the sample chamber comprises one or more gas ports arranged to enable delivery of one or more pulses of gas to locations of laser desorption ionisation on the sample during laser desorption ionisation, such as wherein one or more gas ports is in the form of a nozzle.

The apparatus according to embodiment 8, wherein the one or more gas ports is arranged so as to enable the one or more pulses of gas to collisionally cool ions generated from a sample by laser radiation from the laser.

A method for performing mass cytometry on a sample comprising a plurality of cells, comprising: a. labelling a one or more different target molecules in the sample with one or more mass tags, to provide a labelled sample; b. performing laser desorption ionisation of the sample, wherein laser desorption ionisation is performed at multiple known locations to form a plurality of ion clouds; and c. subjecting the ion clouds to mass spectrometry, whereby detection of ions from the one or more mass tags in the clouds permits construction of an image of the sample.

The method according to embodiment 10, wherein the plurality of ion clouds is a plurality of individual ion clouds, each individual ion cloud being formed from laser desorption ionisation at a known location, and wherein the subjecting the ion clouds to mass spectrometry comprises subjecting individual ion clouds to mass spectrometry.

The method according to embodiment 10 or 11, wherein each different target is bound by a different specific binding pair member (SBP), and each different SBP is linked to a mass tag, such that each target is labelled with a specific mass tag.

The method according to any one of embodiments 10-12, further comprising, prior to step a. or between steps a. and b., the step of treating the sample with an ionization promoter composition.

The method according to embodiment 13, wherein the ionization promoter composition promotes ionization of labelling atoms and/or molecular ions containing the labelling atoms.

The method according to any one of embodiments 10-14, further comprising, prior to step a. or between steps a. and b., the step of treating the sample with laser radiation absorber composition.

d. Secondary Ion Generation Systems

A secondary ion based analyser typically comprises two components. The first is a system for the generation of ions from the sample for analysis. In this apparatus, this is achieved by directing a first focused primary ion beam onto the sample to generate ejected secondary ions; herein it is called a secondary ion generation system. These ejected ions (including any detectable ions from labelling atoms as discussed below) can be detected by a detector system (the second component) for instance a mass spectrometer (detectors are discussed in more detail below). This technique is known as secondary ion mass spectrometry (SIMS).

The secondary ion generation system comprises: a primary ion source for producing primary ions; a primary ion column for passing the primary ions to the sample in a sample chamber; a sample chamber; and an ion microscope for collecting the secondary ions.

In operation, the primary ions produced by the primary ion source bombard the surface of a sample in the sample chamber, transferring energy to the atoms of the sample. This bombardment generates a series of collisions between atoms within the sample. Some atoms near the surface of the sample recoil with enough energy to escape from the surface of the sample (sputtering). Some emitted particles are in an ionised state—these are the secondary ions, which can be subsequently detected.

Primary Ion Source

The primary ions can be any suitable ion for generating sputtering from the sample to be analysed. Examples of primary ion sources are: the Duoplasmatron which generates oxygen ($^{16}O^-$, $^{16}O_2^+$, $^{16}O_2^-$), argon ($^{40}Ar^+$), xenon ($Xe^+$), $SF_5^+$, or $C_{60}^+$ primary ions; a surface ionisation source which generates $^{133}Cs^+$ primary ions; and liquid metal ion guns (LMIG) which generate $Ga^+$ primary ions. Other primary ions include cluster ions such as $Au_n^+$ (n=1-5), $Bi_n^{q+}$ (n=1-7, q=1 and 12), $C_{60}^{q+}$ probes (q=1-3) and large Ar clusters (Muramoto, Brison, & Castner, 2012).

The choice of ion source depends on the type of SIMS being deployed (i.e. static or dynamic) and the sample to be analysed. Static SIMS involves using a low primary ion beam current (1 nA/cm$^2$), usually a pulsed ion beam. Because of the low current, each ion strikes a new section of the sample surface, removing only a monolayer of particles (2 nm). Hence, static SIMS is suitable for imaging and surface analysis (Gamble & Anderton, 2016). Dynamic SIMS involves using a high primary ion beam current (10 mA/cm$^2$), usually a continuous primary ion beam, which results in the fast removal of surface particles. As a result, is possible to use dynamic SIMS for depth profiling. Furthermore, since more material is removed from the sample surface, dynamic SIMS gives a better detection limit than static SIMS. Dynamic SIMS typically produces high image resolution (less than 100 nm)(Vickerman & Briggs, 2013).

Oxygen primary ions enhance ionisation of electropositive elements (Malherbe, Penen, Isaure, & Frank, 2016) and are used in the commercially available Cameca IMS 1280-HR, whereas caesium primary ions are used to investigate electronegative elements (Kiss, 2012) and are used in the commercially available Cameca NanoSIMS 50.

Liquid metal ion guns can produce a tightly focused beam and so are commonly used in static SIMS. An example of a SIMS instrument using a liquid metal ion gun is the SurfaceSeer-I by KORE Technology.

For rapid analysis of a sample a high frequency of ablation is needed, for example more than 20 Hz (i.e. more than 20 ablations per second, giving more than 20 plumes per second). Commonly, the frequency of primary ion pulse generation by the primary ion source is at least 40 Hz, such as at least 50 Hz, or at least 100 Hz. For instance, the frequency of ion pulses is within the range 40-2000 Hz, within the range 40-1500 Hz, within the range 40-500 Hz, within the range 40-200 Hz, within the range 40-150 Hz, or within the range 75-150 Hz. A frequency of more than 40 Hz allows imaging of typical samples to be achieved in a reasonable time. The frequency with which ion pulses can be directed at a spot on the sample and still be individually resolved determines how quickly the pixels of the image can be obtained Primary Ion Column The primary ion column directs the primary ions to the sample. The primary ion column comprises: a mass filter in order to filter out impurities in the primary ion beam; lenses and apertures as appropriate in order to control the intensity and shape of the primary ion beam; and deflection plates in order to shape the primary ion beam and optionally raster the primary ion beam across the surface of the sample (Villacob, 2016). Ion lenses and other components for constructing the primary ion column are commercially available, e.g. from Agilent.

Typically, the ion beam used for secondary ion generation herein has a spot size (i.e. size of the primary ion beam when it hits the sample) of 100 µm or less, such as 50 µm or less, 25 µm or less, 20 µm or less, 15 µm or less, or 10 µm or less. The distance referred to as spot size corresponds to the longest internal dimension of the ion beam, e.g. for a circular beam it is a beam of diameter 2 µm, for a square beam corresponds to the length of the diagonal between opposed corners, for a quadrilateral it is the length of the longest diagonal etc. Beam shaping and beam masking can be employed to provide the spot shape and size.

When used for analysis of biological samples, in order to analyse individual cells the spot size of ion beam used will depend on the size and spacing of the cells. For example, where the cells are tightly packed against one another (such as in a tissue section) the ion beam can have a spot size which is no larger than these cells if single cell analysis is to be conducted. This size will depend on the particular cells in a sample, but in general the ion beam spot will have a diameter of less than 4 µm e.g. within the range 0.1-4 µm, 0.25-3 µm, or 0.4-2 µm. Thus a primary ion beam spot can have a diameter of about 3 µm or less, about 2 µm or less, about 1 µm or less, about 0.5 µm or less than 0.5 µm, such as about 400 nm or less, about 300 nm or less, between 250 nm and 2 um, or between 300 nm and 1 um. In order to analyse cells at a subcellular resolution the system uses a primary ion beam spot size which is no larger than these cells, and more specifically uses a primary ion beam spot size which can ablate material with a subcellular resolution. Sometimes, single cell analysis can be performed using a spot size larger than the size of the cell, for example where cells are spread out on the slide, with space between the cells. The particular spot size used can therefore be selected appropriately dependent upon the size of the cells being analysed. In biological samples, the cells will rarely all be of the same size, and so if subcellular resolution imaging is desired, the ion beam spot size should be smaller than the smallest cell, if constant spot size is maintained throughout the secondary ion generation procedure.

Sample Chamber

The sample chamber of the secondary ion generation system shares many features in common with the sample chamber of the laser ablation-based and lifting-based sampling systems discussed above. It comprises a stage to support the sample. The stage may be a translation stage, movable in the x-y or x-y-z axes. The sample chamber will also comprise an outlet, through which material removed from the sample by the primary ion beam can be directed. The outlet is connected to the detector, enabling analysis of the secondary ions.

The principal difference between the sample chamber of the secondary ion generation system and the sample chambers of the laser ablation-based and lifting-based sampling systems is that the chamber is held under vacuum in order to prevent collisions between secondary ions and other particles within the chamber, which could result in loss of charge from the secondary ions—on a similar basis contrary to the laser ablation and desorption based sample chambers. Loss of secondary ions would result in reduced sensitivity for the apparatus.

Ion Microscope

The secondary ion beams are captured from the sample via an electrostatic lens positioned near to the sample, known in the art as an immersion lens (or an extraction lens). The immersion lens removes the secondary ions immediately from the locality of the sample. This is typically achieved by the sample and the lens having a large difference in voltage potential. Depending on the polarity of the sample vis-à-vis the immersion lens, positive or negative secondary ions are captured by the immersion lens. The polarity of the secondary ions as captured by the immersion lens is independent of the polarity of the ions of the primary ion beam.

The secondary ions are then transferred to the detector by via one or more further electrostatic lenses (known as transfer lenses in the art). The transfer lens(es) focus(es) the beam of secondary ions into the detector. Typically, in systems with multiple transfer lenses, only one transfer lens is engaged in a given analysis. Each lens may provide a different magnification of the sample surface. Commonly, further ion manipulation components are present between the immersion lens and the detector, for example one or more apertures, mass filters or sets of deflector plates. Together, the immersion lens, transfer lens, and any further components, form the ion microscope. Components for the production of an ion microscope are available from commercial suppliers e.g. Agilent.

Camera

The secondary ion generation system may also comprise a camera. Camera systems are discussed above in relation to laser ablation sampling systems, and the features of the above camera can also be present in the secondary ion generation system, except where incompatible (e.g. it can be connected to a light microscope, such as a confocal microscope, but it is not possible to focus a primary ion beam through the same optics as the light which is directed to the camera, because one beam is ions and the other photons).

Post Ionisation

Secondary ionisation of neutral ejected mass particles can be achieved by a variety of techniques, for example laser ionisation (e.g. by a femtosecond laser) and ionisation by an electron beam.

The ions generated in secondary neutral mass spectrometry (SNMS) can then captured by the immersion lens and transferred to the detector as described above for the secondary ions generated directly from primary ion bombardment.

2. Mass Detector System

Exemplary types of mass detector system include quadrupole, time of flight (TOF), magnetic sector, high resolution, single or multicollector based mass spectrometers.

The time taken to analyse the ionised material will depend on the type of mass analyser which is used for detection of ions. For example, instruments which use Faraday cups are generally too slow for analysing rapid signals. Overall, the desired imaging speed, resolution and degree of multiplexing will dictate the type(s) of mass analyser which should be used (or, conversely, the choice of mass analyser will determine the speed, resolution and multiplexing which can be achieved).

Mass spectrometry instruments that detect ions at only one mass-to-charge ratio (m/Q, commonly referred to as m/z in MS) at a time, for example using a point ion detector, will give poor results in imaging detecting. Firstly, the time taken to switch between mass-to-charge ratios limits the speed at which multiple signals can be determined, and secondly, if ions are at low abundance then signals can be missed when the instrument is focused on other mass-to-charge ratios. Thus it is preferred to use a technique which offers substantially simultaneous detection of ions having different m/Q values.

Detector Types

Quadrupole Detector

Quadrupole mass analysers comprise four parallel rods with a detector at one end. An alternating RF potential and fixed DC offset potential is applied between one pair of rods and the other so that one pair of rods (each of the rods opposite each other) has an opposite alternative potential to the other pair of rods. The ionised sample is passed through the middle of the rods, in a direction parallel to the rods and towards the detector. The applied potentials affect the trajectory of the ions such that only ions of a certain mass-charge ratio will have a stable trajectory and so reach the detector. Ions of other mass-charge ratios will collide with the rods.

Magnetic Sector Detector

In magnetic sector mass spectrometry, the ionised sample is passed through a curved flight tube towards an ion detector. A magnetic field applied across the flight tube causes the ions to deflect from their path. The amount of deflection of each ion is based on the mass to charge ratio of each ion and so only some of the ions will collide with the detector—the other ions will be deflected away from the detector. In multicollector sector field instruments, an array of detectors is be used to detect ions of different masses. In some instruments, such as the ThermoScientific Neptune Plus, and Nu Plasma II, the magnetic sector is combined with an electrostatic sector to provide a double-focussing magnetic sector instrument that analyses ions by kinetic energy, in addition to mass to charge ratio. In particular those multidetectors having a Mattauch-Herzog geometry can be used (e.g. the SPECTRO MS, which can simultaneously record all elements from lithium to uranium in a single measurement using a semiconductor direct charge detector). These instruments can measure multiple m/Q signals substantially simultaneously. Their sensitivity can be increased by including electron multipliers in the detectors. Array sector instruments are always applicable, however, because, although they are useful for detecting increasing signals, they are less useful when signal levels are decreasing, and so they are not well suited in situations where labels are present at particularly highly variable concentrations.

Time of Flight (TOF) Detector

A time of flight mass spectrometer comprises a sample inlet, an acceleration chamber with a strong electric field applied across it, and an ion detector. A packet of ionised sample molecules is introduced through the sample inlet and into the acceleration chamber. Initially, each of the ionised sample molecules has the same kinetic energy but as the ionised sample molecules are accelerated through the acceleration chamber, they are separated by their masses, with the lighter ionised sample molecules travelling faster than heaver ions. The detector then detects all the ions as they arrive. The time taking for each particle to reach the detector depends on the mass to charge ratio of the particle.

Thus a TOF detector can quasi-simultaneously register multiple masses in a single sample. In theory TOF techniques are not ideally suited to ICP ion sources because of their space charge characteristics, but TOF instruments can in fact analyse an ICP ion aerosol rapidly enough and sensitively enough to permit feasible single-cell imaging. Whereas TOF mass analyzers are normally unpopular for atomic analysis because of the compromises required to deal with the effects of space charge in the TOF accelerator and flight tube, tissue imaging according to the subject disclosure can be effective by detecting only the labelling atoms, and so other atoms (e.g. those having an atomic mass below 100) can be removed. This results in a less dense ion beam, enriched in the masses in (for example) the 100-250 dalton region, which can be manipulated and focused more efficiently, thereby facilitating TOF detection and taking advantage of the high spectral scan rate of TOF. Thus rapid imaging can be achieved by combining TOF detection with choosing labelling atoms that are uncommon in the sample and ideally having masses above the masses seen in an unlabelled sample e.g. by using the higher mass transition elements. Using a narrower window of label masses thus means that TOF detection to be used for efficient imaging.

Suitable TOF instruments are available from Tofwerk, GBC Scientific Equipment (e.g. the Optimass 9500 ICP-TOFMS), and Fluidigm Canada (e.g. the CyTOF™ and CyTOF™2 instruments). These CyTOF™ instruments have greater sensitivity than the Tofwerk and GBC instruments and are known for use in mass cytometry because they can rapidly and sensitively detect ions in the mass range of rare earth metals (particularly in the m/Q range of 100-200; see Bandura et al. (2009; *Anal. Chem.*, 81:6813-22)). Thus these are preferred instruments for use with the disclosure, and they can be used for imaging with the instrument settings already known in the art e.g. Bendall et al. (2011; Science 332, 687-696) & Bodenmiller et al. (2012; *Nat. Biotechnol.* 30:858-867). Their mass analysers can detect a large number of markers quasi-simultaneously at a high mass-spectrum acquisition frequency on the timescale of high-frequency laser ablation or sample desorption. They can measure the abundance of labelling atoms with a detection limit of about 100 per cell, permitting sensitive construction of an image of the tissue sample. Because of these features, mass cytometry can now be used to meet the sensitivity and multiplexing needs for tissue imaging at subcellular resolution. By combining the mass cytometry instrument with a high-resolution laser ablation sampling system and a rapid-transit low-dispersion sample chamber it has been possible to permit construction of an image of the tissue sample with high multiplexing on a practical timescale.

The TOF may be coupled with a mass-assignment corrector. The vast majority of ionisation events generate $M^+$ ions, where a single electron has been knocked out of the atom. Because of the mode of operation of the TOF MS there is sometimes some bleeding (or cross-talk) of the ions of one mass (M) into the channels for neighbouring masses ($M\pm1$), in particular where a large number of ions of mass M are entering the detector (i.e. ion counts which are high, but not so high that an ion deflector positioned between the sampling ionisation system and MS would prevent them from entering the MS, if the apparatus were to comprise such an ion deflector). As the arrival time of each $M^+$ ion at the detector follows a probability distribution about a mean (which is known for each M), when the number of ions at mass $M^+$ is high, then some will arrive at times that would normally be associated with the $M-1^+$ or $M+1^+$ ions. However, as each ion has a known distribution curve upon entering the TOF MS, based on the peak in the mass M channel it is possible to determine, the overlap of ions of mass M into the $M\pm1$ channels (by comparison to the known peak shape). The calculation is particularly applicable for TOF MS, because the peak of ions detected in a TOF MS is asymmetrical. Accordingly it is therefore possible to correct the readings for the M-1, M and M+1 channels to appropriately assign all of the detected ions to the M channel. Such corrections have particular use in correcting imaging data due to the nature of the large packets of ions produced by sampling and ionisation systems such as those disclosed herein involving laser ablation (or desorption as discussed below) as the techniques for removing material from the sample. Programs and methods for improving the quality of data by de-convoluting the data from TOF MS are discussed in WO2011/098834, U.S. Pat. No. 8,723,108 and WO2014/091243.

Tandem MS Detector

Tandem MS detectors can be split into two broad groups: tandem in space and tandem in time. In tandem in space detectors, each of the first and second separation elements are spatially separate (but connected, under vacuum). In time, the analysis occurs in the same place, via the use of ion traps to capture the ions resulting from the first separation before the second analysis is conducted. Essential to tandem MS is the fragmentation of the ion(s) separated in the first separation element before analysis in the second separation element. Fragmentation can be achieved by a number of means. In some instances, the ionisation process is sufficient to cause subsequent breakdown of the initial ion within the tandem MS. Alternatively, the initial ion may be fragmented by collision or transfer (such as by electron capture dissociation, electron transfer dissociation, negative electron transfer dissociation, electron detachment dissociation, charge transfer dissociation) or photodissociation (such as infrared multiphoton dissociation or blackbody infrared radiative dissociation). Various arrangements of components can be used to achieve tandem separation. One example is a quadrupole followed by a TOF detector. Tandem MS detectors are commercially available, from suppliers such as Waters Corporation, Agilent Technologies, SCIEX, Shimadzu and the like.

Dead-Time Corrector

As noted above, signals in the MS are detected on the basis of collisions between ions and the detector, and the release of electrons from the surface of the detector hit by the ions. When a high count of ions is detected by the MS resulting in the release of a large number of electrons, the detector of the MS can become temporarily fatigued, with the result that the analog signal output from the detector is temporarily depressed for one or more of the subsequent packets of ions. In other words, a particularly high count of ions in a packet of ionised sample material causes a lot of electrons to be released from the detector surface and secondary multiplier in the process of detecting the ions from that packet of ionised sample material, meaning that fewer electrons are available to be released when the ions in subsequent packets of ionised sample material hit the detector, until the electrons in the detector surface and secondary amplifier are replenished.

Based on a characterisation of the behaviour of the detector, it is possible to compensate for this dead-time phenomenon. A first step is to analyse the ion peak in the analog signal resulting from the detection of the nth packet of ionised sample material by the detector. The magnitude of the peak may be determined by the height of the peak, by the area of the peak, or by a combination of peak height and peak area.

The magnitude of the peak is then compared to see if it exceeds a predetermined threshold. If the magnitude is below this threshold, then no correction is necessary. If the magnitude is above the threshold, then correction of the digital signal from at least one subsequent packet of ionised sample material will be performed (at least the (n+1)th packet of ionised sample material, but possibly further packets of ionised sample material, such as (n+2)th, (n+3)th, (n+4)th etc.) to compensate for the temporary depression of the analog signal from these packets of ionised sample material resulting from the fatiguing of the detector caused by the nth packet of ionised sample material. The greater the magnitude of the peak of the nth packet of ionised sample material, the more peaks from subsequent packets of ionised sample material will need to be corrected and the magnitude of correction will need to be greater. Methods for correcting such phenomena are discussed in Stephan et al. (1994; Vac. Sci. Technol. 12:405), Tyler and Peterson (2013; Surf Interface Anal. 45:475478), Tyler (2014; Surf Interface Anal. 46:581-590), WO2006/090138 and U.S. Pat. No. 6,229,142, and these methods can be applied by the dead-time corrector to the data, as described herein.

Analyser Apparatus Based on Optical Emission Spectra Detection

Sampling and Ionisation Systems

Laser Ablation Based Sampling and Ionising System

The laser ablation sampling system sampling system described above in relation to mass-based analysers can be employed in an OES detector-based system. For detection of atomic emission spectra, most preferably, an ICP is used to ionise the sample material removed from the sample, but any hard ionisation technique that can produce elemental ions can be used.

As appreciated by one of skill in the art, certain optional further components of the laser ablation based sampling and ionising system above, described in relation to avoiding overload of the mass-based detector, may not be applicable to all OES detector-based systems, and would not be incorporated, if inappropriate, by the skilled artisan. Furthermore, the skilled artisan will appreciate that while OES can detect elements, it cannot distinguish between isotopes of the element. Accordingly, where target SBPs/analytes are to be distinctively analysed, OES should be conducted with reagents labelled with different elements, rather isotopes of the same element.

e. Desorption Based Sampling and Ionising System

The desorption-based sampling system described above in relation to mass-based analysers can be employed in an OES detector-based system. For detection of atomic emission spectra, most preferably, an ICP is used to ionise the sample material removed from the sample, but any hard ionisation technique that can produce elemental ions can be used.

As appreciated by one of skill in the art, certain optional further components of the desorption based sampling and ionising system above, described in relation to avoiding overload of the mass-based detector, may not be applicable to all OES detector-based systems, and would not be incorporated, if inappropriate, by the skilled artisan.

3. Photodetectors

Exemplary types of photodetectors include photomultipliers and charged-coupled devices (CCDs). Photodetetors may be used to image the sample and/or identify a region of interest prior to imaging by elemental mass spectrometry.

Photomultipliers comprise a vacuum chamber comprising a photocathode, several dynodes, and an anode. A photon incident on the photocathode causes the photocathode to emit an electron as a consequence of the photoelectric effect. The electron is multiplied by the dynodes due to the process of secondary emission (discussed in more detail with reference to SIMS) to produce a multiplied electron current, and then the multiplied electron current is detected by the anode to provide a measure of detection of electromagnetic radiation incident on the photocathode. Photomultipliers are available from, for example, ThorLabs.

A CCD comprises a silicon chip containing an array of light-sensitive pixels. During exposure to light, each pixel generates an electric charge in proportion to the intensity of light incident on the pixel. After the exposure, a control circuit causes a sequence of transfers of electric charge to produce a sequence of voltages. These voltages can then be analysed to produce an image. Suitable CCDs are available from, for example, Cell Biosciences.

Constructing an Image

The apparatus above can provide signals for multiple atoms in packets of ionised sample material removed from the sample (be that by ablation, ion bombardment or any other technique). Detection of an atom in a packet of sample material reveals its presence at the position of ablation, be that because the atom is naturally present in the sample or because the atom has been localised to that location by a labelling reagent. By generating a series of packets of ionised sample material from known spatial locations on the sample's surface the detector signals reveal the location of the atoms on the sample, and so the signals can be used to construct an image of the sample. By labelling multiple targets with distinguishable labels it is possible to associate the location of labelling atoms with the location of cognate targets, so the method can build complex images, reaching levels of multiplexing which far exceed those achievable using existing techniques. The images generated by the methods can reproduce the staining patterns and the proportion of cells expressing a given marker as determined by IFM, thereby confirming the method's suitability for imaging.

Assembly of signals into an image will use a computer and can be achieved using known techniques and software packages. For instance, the GRAPHIS package from Kylebank Software may be used, or other packages such as TERAPLOT can also be used. Imaging using MS data from techniques such as MALDI-MSI is known in the art e.g. Robichaud et al. (2013; J Am Soc Mass Spectrom 24 5:718-21) discloses the 'MSiReader' interface to view and analyze MS imaging files on a Matlab platform, and Klinkert et al. (2014: Int J Mass Spectrom http://dx.doi.org/10.1016/j.ijms.2013.12.012) discloses two software instruments for rapid data exploration and visualization of both 2D and 3D MSI data sets in full spatial and spectral resolution e.g. the 'Datacube Explorer' program.

Images obtained using the methods disclosed herein can be further analysed e.g. in the same way that IHC results are analysed. For instance, the images can be used for delineating cell sub-populations within a sample, and can provide information useful for clinical diagnosis. Similarly, SPADE analysis can be used to extract a cellular hierarchy from the high-dimensional cytometry data which methods of the disclosure provide (Qiu et al. (2011; Nat. Biotechnol. 29:886-91)).

Apparatus Comprising the Sample of the Invention

Also provided herein is an apparatus as described above comprising a sample of the invention (i.e. a sample that has been stained with reagents of the invention). In some instances the apparatus is an imaging mass cytometer. In some instances the apparatus is a mass cytometer.

Computer Control of Methods Disclosed Herein

The methods disclosed herein may also be provided as a computer program product including a non-transitory, machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions. Accordingly, the invention also provides a machine-readable medium comprising instructions for performing a method as disclosed herein.

Definitions

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

The word "substantially" does not exclude "completely" e.g. a composition which is "substantially free" from Y may be completely free from Y. Where necessary, the word "substantially" may be omitted from the definition of the disclosure.

Molecular weights ($M_n$) and polydispersity indexes (PDI=$M_w/M_n$) were obtained by aqueous gel permeation chromatography (GPC), performed at room temperature, with 0.2 M $NaNO_3$ as the eluent. Molecular weights are referenced to polyethylene glycol (PEG) standards.

Quantitation of Biological Macromolecules on a Solid Surface

Solid surfaces (or solid supports), for example glass slides, can be manufactured that are amenable to the binding and retention of different biological macromolecules (either commercially purchased or produced as described below in the examples). Kits comprising such solid surfaces, and optionally reporter SBPs, are described herein. Methods include the use of such solid surfaces in the detection (e.g., by LA-ICP-MS) of biological macromolecules are also described herein.

The biological macromolecules could be any molecules that may be bound by an SBP as described herein. For example, the macromolecules may include DNA (e.g., cDNA), protein, or both DNA and protein. When macromolecules bound to solid surfaces bind, react or hybridise to other biological macromolecules conjugated to distinguishing tags containing metal atoms can be detected in a quantitative manner using imaging mass cytometry. For example, initial experiments have shown that metal tagged DNA (e.g., cDNA) and/or protein molecules can be spotted onto glass slides and ablated allowing for the generation of an image and quantification of the amount of DNA or protein within the spot. In certain aspects, a protein molecule may be mass tagged by an SBP (e.g., antibody) that binds to the protein when the protein is immobilized on the solid support (e.g., when bound by an antibody covalently bound to the solid support). The technology can also be applied in scenarios including DNA/RNA hybridization efficiency, the multiplexing of traditional protein, oligonucleotide, and lectin microarrays, and the analysis of protein-protein and protein-carbohydrate interactions.

In certain aspects, the solid surface may be an assay barcoded bead comprising a unique combination of elements (e.g., isotopes) that relate to a specific biological macromolecule (e.g., protein or DNA/RNA) that the bead is functionalized to bind (e.g., by an antibody or DNA oligonucleotide on the bead surface). The biological macromolecule, or a reporter SBP that binds the biological macromolecule, may be mass tagged to identify the presence of the macromolecule on the bead.

In certain aspects, the solid surface may be a planar surface, such as an array on a glass slide. Individual locations on the glass surface (e.g., spots of an array) may bind a specific biological macromolecule, such as through an SBP intermediate (such as an antibody or an single stranded DNA oligonucleotide). In certain aspects, SBPs may be bound to the slide directly (e.g., through covalent attachment to a reactive group presented by the surface) or through a polymer intermediate (e.g., a 3D polymer such as a gel as described herein).

Experimentation has determined that certain films of solid supports may be unsuitable to IMC. In certain aspects, the solid support may comprise a film that can be ablated through by LA-ICP-MS (such as a film that is less than 12, 10, 8, 6, or 4 um). Alternatively or in addition, the solid support (e.g., film thereof) may not comprise any metals that would overwhelm the LA-ICP-MS detector. In certain aspects, an array of the subject embodiments may have a polymer gel thickness that is less than 6 um, less than 4 um, or less than 2 um, such as between 1 and 6 um, such as 2 and 4 um.

The sample applied to the solid surface may be any biological fluid, such as blood plasma, serum, urine, saliva, synovial fluid, or cell culture supernatant or lysate. In certain aspects, the sample may be blood (e.g., plasma or serum), and blood cells (e.g., a blood cell smear) may be analysed separately (for example, on a separate portion of a slide). Free analytes secreted by cells may be analyzed in the array, and a cell smear comprising the cells may be analysed alongside (e.g., on the same slide as) the array.

In certain aspects, an array may comprise a dye (e.g., color or fluorescent dye) that allows for identification of individual spots on the array by light (e.g., brightfield or fluorescence) microscopy.

When the solid surface immobilizes antibodies or target proteins, it may enable detection (e.g., by LA-ICP-MS) of at least some target proteins present at a concentration of less than 100, 1000, 10000, or 100000 pg/ml, such as between 10 and 100000 pg/ml or between 100 and 10000 pg/ml. In certain aspects, the solid surface may be used to detect targets at low concentrations (e.g., less than 100 pg/ml, less than 10 pg/ml, or less than 1 pg/ml).

As described herein, a biological macromolecule bound to a solid support may be mass tagged (either before or after binding to the solid support). For example, a biological macromolecule may be mass tagged by binding of a reporter SBP to the macromolecule, where the reporter SBP comprises the mass tag. The reporter SBP may comprise a polymer mass tag (e.g., loaded with a metal) or a nanoparticle mass tag (e.g., comprising a core densely packed with a metal). For example, a reporter SBP comprising a nanogold mass tag may provide a stronger signal than a polymer mass tag, allowing for detection of lower amounts or concentrations of a target. In certain aspects, some reporter SBPs may be bound to a nanoparticle providing a high signal, and other reporter SBPs (e.g., that bind to higher abundance targets) may comprise a metal polymer mass tag providing a lower signal than the nanoparticle.

In some cases, the reporter biomolecule may be directly tagged (e.g., by covalent attachment of a metal-loaded polymer, as described herein). For example, cDNA oligonucleotides obtained from RNA may be mass tagged by performing reverse transcription and/or amplification from a mass tagged primer oligonucleotide, or though labelling of cDNA by conjugation to a mass tag. In one example, reverse transcription may incorporate aminoallyl-UTPs, and the cDNA may subsequently be reacted with an amine reactive mass tag, such as a commercially available p-SCN-Bn-DOTA polymer loaded with a metal (e.g., metal isotope). In certain aspects, macromolecules from a plurality of samples may be mass tagged by sample, such that different macromolecules from the same sample comprise the same mass tag, which is different from the mass tag associated with macromolecules from another sample. The mass tag may comprise a metal element or isotope, such as a lanthanide element or isotope. In certain aspects, the mass tag may include a polymer with a metal-chelating pendant group, such as DOTA or DTPA. A mass tag polymer may be coupled to the oligonucleotide through any chemistry, such as amine chemistry. In certain aspects, the mass tag may be coupled to the Samples may then be pooled and their macromolecules immobilized on the same solid support. The solid support may then be subjected to mass analysis (e.g., ICP-MS, such as LA-ICP-MS).

In certain aspects, macromolecules from at least 2, 3, 5, 8, 10, 15, or 20 samples may be distinctively mass tagged by sample, pooled, and added to the same solid support for mass analysis. For example, the cDNA of at least 2, 3, 5, 8, 10, 15, or 20 samples may be distinctively mass tagged by sample, pooled, and added to a gene expression microarray (e.g., comprising single stranded DNA probes to a target gene sequence at each spot) for mass analysis. Measuring multiple samples at each spot at the same time may control for differences in arrays and experiment runs (e.g., such as instrument sensitivity drift between and during runs). In certain aspects, some of the samples may be subjected to a treatment and compared to a control sample (e.g., untreated negative control). In certain aspects, multiple samples may be compared to the same control sample. The difference in expression of a gene between a treatment condition and untreated condition, or two treatments, may be represented as a fold change. The expression profiles of different samples can be compared, and targets (e.g., genes) that are expressed in a similar and/or different pattern (e.g., trends of upregulation or downregulation) may be identified. Gene expression across different samples (e.g., treatment conditions) can be analysed together, such that patterns and/or relationships across samples or treatment conditions can be identified.

In certain aspects, the expression of a target gene of a sample may be normalized to overall expression of targets from the sample or to one or more housekeeping genes of the sample, and then compared to expression of the target gene of one or more other samples. When samples are being compared by addition to the same microarray (e.g., as described above), then calibrations to an element standard during a sample run may be unnecessary for preventing overall sensitivity drift. That said, calibration and/or normalization of different mass tags from different samples to an element standard comprising multiple masses may reduce variations in the relative sensitivity of the instrument across a mass range.

The inventors demonstrate the capacity of mass cytometry for quantifying levels of target molecules within protein or nucleic acid solutions. Samples were first immobilised to a mass cytometry solid supports. Use of both planar and particulate mass cytometry sample supports is exemplified herein.

Example 1—Covalent Immobilisation of Detected Protein

To demonstrate quantification of protein species, antibodies labelled with mass tags were spotted onto a slide. The spots were ablated, and the number of ions counted and correlated with the concentrations and quantities of antibody present, thereby generating a calibration curve and providing an initial demonstration of a linear relationship between antibody concentration and ion count. Furthermore, multiplexed quantification was demonstrated.

Carboxyl functionalized glass slides (XanTec, Germany) were used for immobilisation of the antibodies. First, the slides were activated to form NHS functional groups, which are capable of covalently linking proteins with free amines to the slides. The antibodies immobilised to the plate were: (1) anti-CD20, labelled with $^{147}$Sm, (2) anti-CD138, labelled with $^{150}$Nd, (3) anti-CD183, labelled with $^{156}$Gd, (4) anti-CD357, labelled with $^{159}$Tb, (5) anti-CD45Ro, labelled with $^{165}$Ho, (6) anti-CD66a, labelled with $^{168}$Er, (7) anti-CD273, labelled with $^{172}$Yb, and (8) anti-CD127, labelled with $^{176}$Yb. A master solution containing all of the 10 labelled antibodies was serially diluted and an aliquot of each of the series were covalently immobilised onto discrete regions of an imaging surface.

The total ion count from each mass tag was collected over a 250000 µm$^2$ ablation area for each of the serial dilutions. The total ion count (total intensity per ablation area) vs. the quantity of immobilised antibody is shown in FIG. 1a. The individual total ion counts for each of the mass tags are plotted individually.

In brief, 1 µl of antibody solution was spotted onto the NHS activated slide. The spotted slide was incubated overnight at 4° C. in a humidified chamber, to allow protein deposition, via reaction of NHS with amines on the antibodies, to take place. The following morning, the slide was washed three times with 1×PBS. To ensure that there were no free NHS groups that could react with other reagents, an optional blocking step can be performed by incubating the slide with 1% BSA in PBS at room temperature for an hour, followed by gentle rinsing with 1×PBS and a final wash with ddH2O. The slides were air dried before sampling and data acquisition by IMC.

Under the instrument parameters employed, no increase in total intensity was observed at antibody quantities ranging from $1\times10^{-3}$ to $1\times10^{-2}$ attomole (am). Beyond $1\times10^{-2}$ am, an increase was seen, albeit not for all tested antibodies. Beyond 1 am, a linear increase in ion count was observed for each of the mass tags, indicating that the amount of antibody functionalised to the surface corresponds directly with the total ion intensity. Thus, a reliable and linearly quantifiable signal at levels as low as 1 am has been demonstrated to be detectable in this assay.

This corresponds to a detection threshold of an average of lower than 1 antibody per pixel (i.e. 1 $\mu m^2$) across the entire ablation area (i.e. 500×500 $\mu m^2$). Of course, the particular detection threshold used is dependent upon the particular mass tag, as what was detected is the number of ions of the labelling atom; a mass tag comprising a higher number of labelling atoms will enable detection of a lower copy number of atoms than a species labelled with a mass tag comprising a lower number of labelling atoms per mass tag.

Example 2—Non-Covalent Immobilisation of Detected Protein

Example 1's experimental format relied on direct immobilisation of the detected protein to the slide (via reaction with NHS functionalities on the slide with amine on the detected protein species). In many instance, it is experimentally unviable to immobilise all species in a biological sample to the slide (e.g. tissue fluid which contains many proteinaceous and other chemical components). According, Example 2 demonstrates that specific proteins can be immobilised non-covalently to the mass cytometry sample carrier by a first immobilising a specific capture element to the slide before subsequent immobilisation of the target analyte. Beyond verification of this technique, the example demonstrates that the ion count is dependent of the amount of the specifically bound labelled target species immobilised on the slide, which in turn varies with the number of capture elements capable of binding specifically to the target that have been immobilised to the slide.

In this instance, again carboxyl functionalized glass slides (XanTec, Germany) were used. These slides were activated with NHS. Following activation, capture elements were spotted onto the slide, thereby forming an array. In this example, polyclonal goat anti-mouse IgG was used as the capture element. 1 µL of polyclonal goat anti-mouse IgG was spotted onto the activated slides at a concentration of 1 mg/ml. The spotted slide was incubated overnight at 4° C. in a humidified chamber, to allow protein deposition to take place. The following morning, the slide was washed three times with 1×PBS. To ensure that there were no free NHS groups that could react with other reagents, the slide was incubated with 1% BSA in PBS at room temperature for an hour, followed by a gentle rinse with 1×PBS. Following this, the labelled antibody (anti-human CD45RO labelled with $^{165}$Ho; 10 µl) was spotted onto the slide at different concentration, in triplicate for each concentration, and incubated for 1 hour at room temperature to allow the labelled antibody to be bound by the goat anti-mouse polyclonal in a humidity chamber. Following this incubation step, the slide was washed three times in 1×PBS Tween, washed in deionised $H_2O$ and dried in preparation for IMC acquisition.

Figure 2:
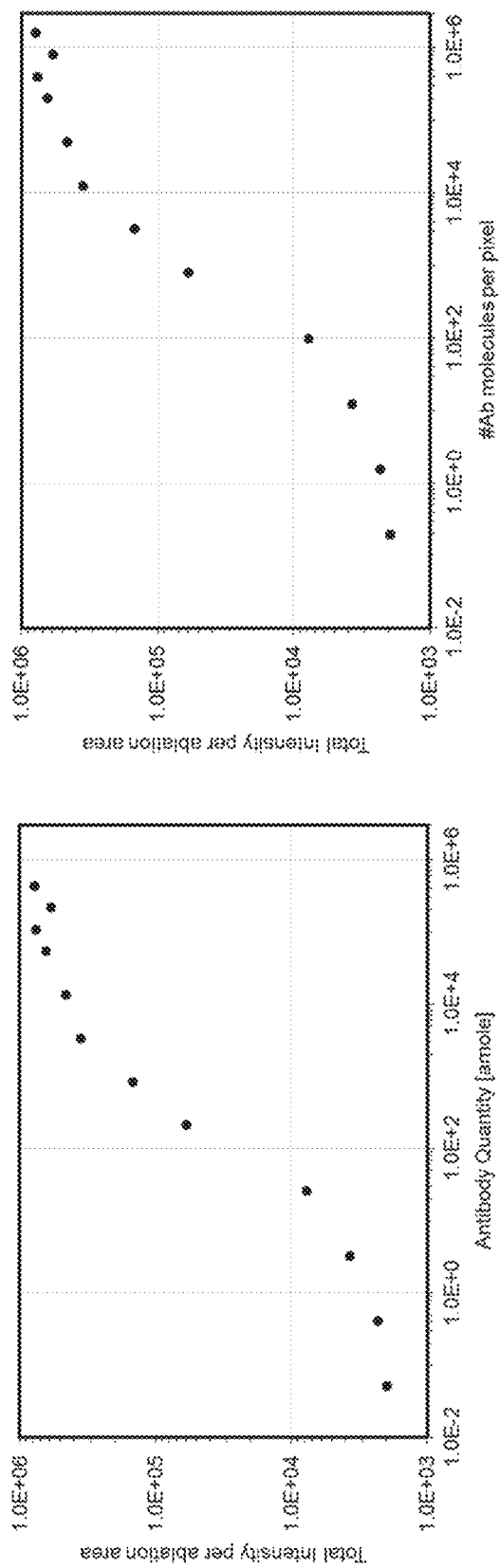
FIG. 2. Assessment of upper and lower detection limit using IMC. Polyclonal secondary goat-anti-mouse IgG at a concentration of 1 mg/ml was manually spotted on NHS activated hydrogel coated glass slides followed by quenching and stringent rinsing with washing buffers. Then, 10 µl of 165Ho tagged monoclonal antibody (ant-human CD45RO) at different concentrations added to react with GAM molecules for 1 hr. IMC acquisition was performed following washing and drying steps. Graphs (A&B) are showing total intensities per ablation area (500×500 µm) versus antibody concentration (A) and number of antibody molecule spotted per pixel (B). Each point represents the mean signal intensity of triplicate IMC acquisitions.

Data was then acquired by ablation of (500×500) $\mu m^2$ areas encompassing the spots. FIG. 2 presents the results of the experiment. As shown for antibody samples covalently immobilised to the surface, captured antigens were detected quantifiably in the low am range).

The results demonstrate that specific non-covalent capturing can be used to reliably detect target antigens in a quantifiable manner (FIG. 2A).

To investigate the effect of the number of capture elements and so capacity of the mass cytometry sample carrier for binding to the target on the recorded ion counts, a serial dilution of polyclonal goat anti-mouse antibody was prepared, and the different concentrations (varying from 0.5 ng/ml-2 mg/ml in 1×PBS buffer) spotted onto carboxyl functionalized glass slides (XanTec, Germany) that had been NHS activated. The slide was then incubated overnight at 4° C. in a humidified chamber, to allow protein immobilisation to take place. The following morning, the mass cytometry sample carrier was then washed using 1×PBS Tween. Next the mass cytometry sample carrier was blocked using blocking solution (1% BSA in PBS) at room Temperature for 1 hr, followed by a gentle rinse in 1×PBS.

The solution of target protein anti-human (CD45RO labelled with $^{165}$Ho) to be bound by the polyclonal goat anti-mouse capture element was prepared at high (62.5 µg/ml), medium (1.25 µg/ml), and low (0.0625 µg/ml) concentrations. 10 µl of each antibody mix was spotted onto a discrete capture element region of the slide (here, each discrete region is represented by the immobilised spot of the polyclonal antibody capture element). The mass cytometry sample carrier was then incubated for 30 minutes at room temperature in a humidity chamber, washed three times in 1×PBS Tween, washed in deionised $H_2O$ and dried in preparation for IMC acquisition.

Figure 3:
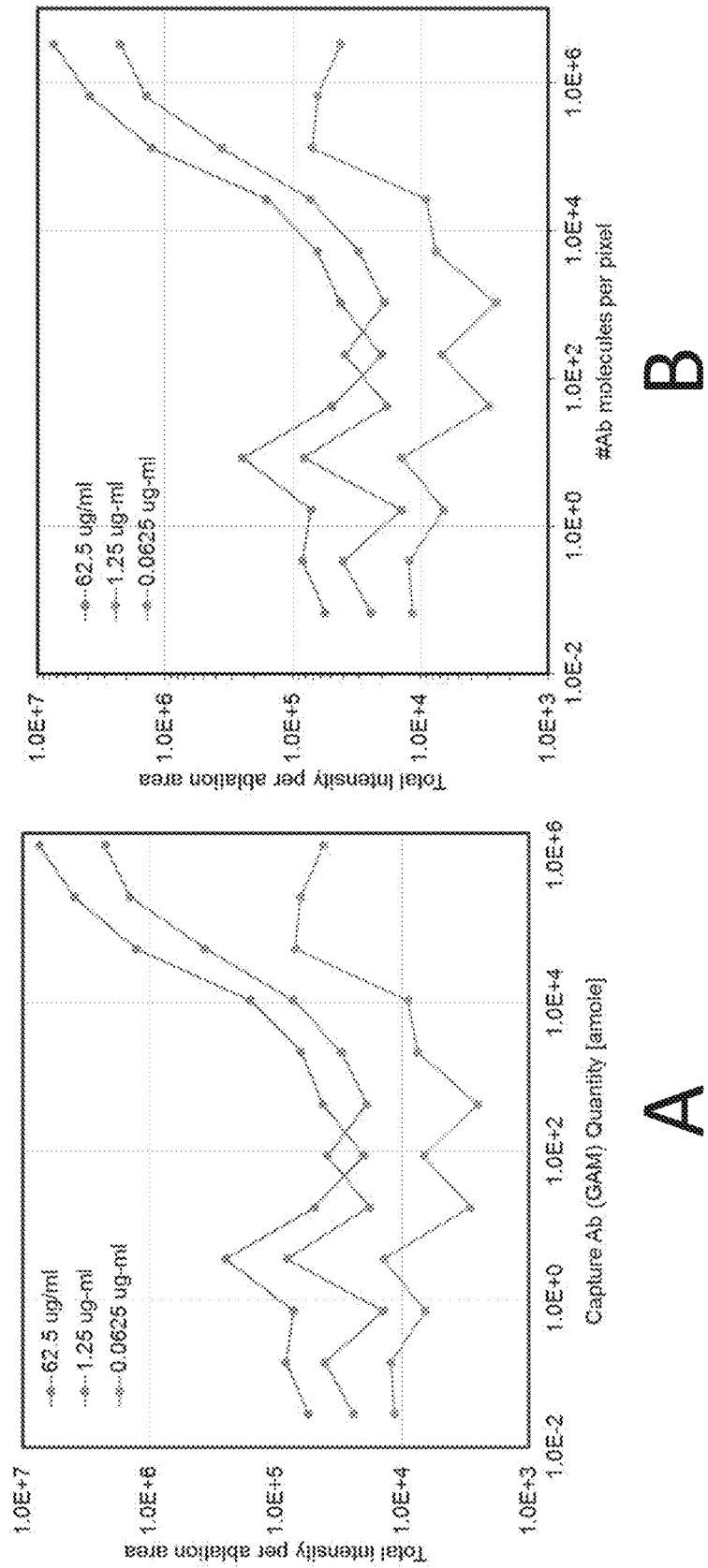
FIG. 3. Evaluation of binding efficiency between immobilized polyclonal IgG and metal-tagged monoclonal Ab. Different concentrations of polyclonal secondary goat-anti-mouse IgG were manually spotted at on NHS activated hydrogel coated glass slides followed by quenching and stringent rinsing with washing buffers. Then, 10 µl of 165Ho tagged monoclonal antibody (anti-human CD45RO), which was pre diluted at concentrations of 62.5 µg/ml, 1.25 µg/ml, and 0.0625 µg/ml, were added to react with GAM molecules for 1 hr IMC acquisition was performed followed by washing and drying steps. Graphs (A&B) are showing total intensities per ablation area (500×5000 µm$^2$) versus antibody concentration (A) and number of Ab molecule spotted per pixel (B). Each point represents the mean signal intensity of triplicate IMC acquisitions.

FIGS. 3A and B show that the upper limit for the ion count is proportional to the amount of capture element immobilised to the mass cytometry sample carrier and the amount of target protein immobilised to the capture element. At a concentration of 0.0625 µg/ml, the ion count is low irrespective of the concentration of capture element immobilised to the mass cytometry sample carrier. Here, the capture element is in excess at all concentrations, and so no effect is seen in increasing the concentration of capture element on the mass cytometry sample carrier. At the intermediate concentration (1.25 µg/ml; 20-fold higher concentration than 0.0625 µg/ml) a higher (vis-A-vis the signal for 0.0625 µg/ml) but relatively consistent signal is seen until approximately 100 amole of capture element is immobilised to the mass cytometry sample carrier. At higher concentrations of capture element, an increase in signal is seen; with an increased amount of capture element immobilised, more of the mass tagged antibody can be immobilised and so detected following IMC. At $1\times10^6$ amole of capture element, the ion count appears to be levelling out, indicating that almost all of the mass tagged target protein is being captured at that level of capture element. At the highest concentration (62.5 µg/ml; 50-fold higher concentration than 1.25 µg/ml; 1000-fold higher concentration than 0.0625 µg/ml), a curve of similar form is observed as seen at the intermediate concentration. Ion count is higher at every level of capture element, as expected given that more of the mass tagged target is available for capture by the capture element in the equilibrium between bound and mobile target. With increasing quantities of capture element, more mass tagged target is captured, as evidenced by the increased ion count following IMC. At the highest tested amount of capture agent, the observed curve is tending towards a plateau, indicating that the number of capture elements not limiting the amount of labelled target that is being immobilised.

Exemplary protocol for protein spotting:
1. To generate the data for FIG. 3, carboxyl functionalized glass slides from XanTec (HC slides) were used, and prior to protein spotting the slide surface was activated to form NHS functional groups for a covalent coupling of protein molecules.
2. Different concentrations (0.5 ng/ml-2 mg/ml) of polyclonal GAM IgG as a capture protein in 1×PBS buffer were prepared.
3. 1 µl of capture protein was spotted using an automatic spotter onto HC slides.
4. Slides were incubated overnight at 4° C. in humidified chamber, to allow protein deposition to take place.
5. After completion of protein adsorption slides were briefly rinsed 3 times using 1×PBS Tween 20.
6. Samples were blocked using blocking solution (1% BSA in PBS) at room Temperature for 1 hr, and rinsed gently with 1×PBS once.
7. Reporter metal-tagged monoclonal antibody mix was prepared at three different concentrations (High (62.5 µg/ml), medium (1.25 µg/ml), and Low (0.0625 µg/ml)).
8. 10 µl or less of antibody mix was added into respective spot area.
9. Slides were incubated at RT for 30 min in humidified chamber, then washed with PBST 3× and ddH20 1×, then printed microarrays were air dried before IMC acquisition.

Example 3—Detection of Mass Tagged Nucleotides

The inventors also demonstrate the capacity of IMC to quantitatively determine the concentration of nucleic acid.

A DNA oligonucleotide labelled with a $Tb^{159}$-based mass tag was diluted to concentrations of 6.46 µM, $6.46 \times 10^2$ µM and $6.46 \times 10^{-4}$ µM. 1 µl of the solution was manually or machine spotted onto Nexterion Slide E (Schott AG, Germany). Slides were then incubated in a humidity chamber for approximately 30 minutes before leaving to dry overnight. Dried samples were then baked on a heat block set to 80° C. for 4 hrs, before the following wash regime was carried out: washing in 1% Triton PBS for 5 minutes, washing twice in 1 mM HCl for two minutes and washing in 100 mM KCl for 10 minutes. Samples were then rinsed with $H_2O$ for approximately one minute prior to drying in preparation for imaging mass cytometry.

Figure 4:
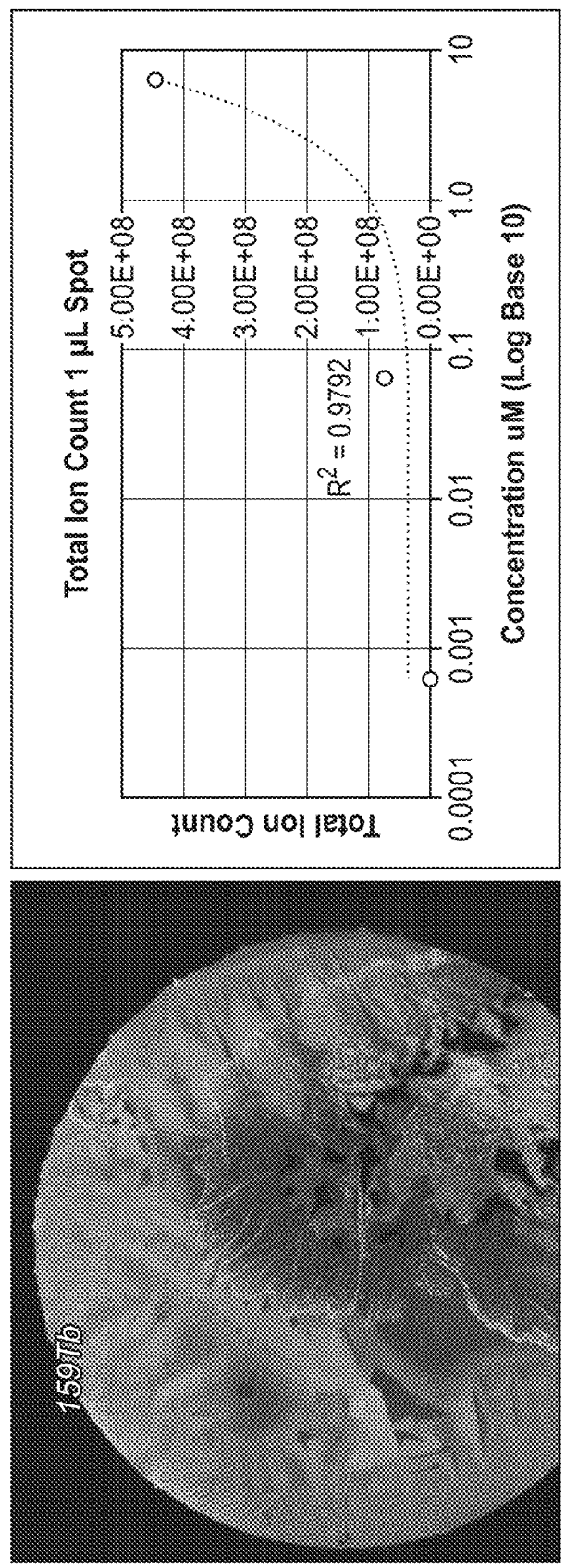
FIG. 4. 1 µL of 6.46 µM DNA Conjugated to DM10.1 Polymer containing Tb159 hand spotted onto a glass slide and ablated. From the data files used to generate this image, the total ion count and the number of probes can also be calculated.
Figure 5:
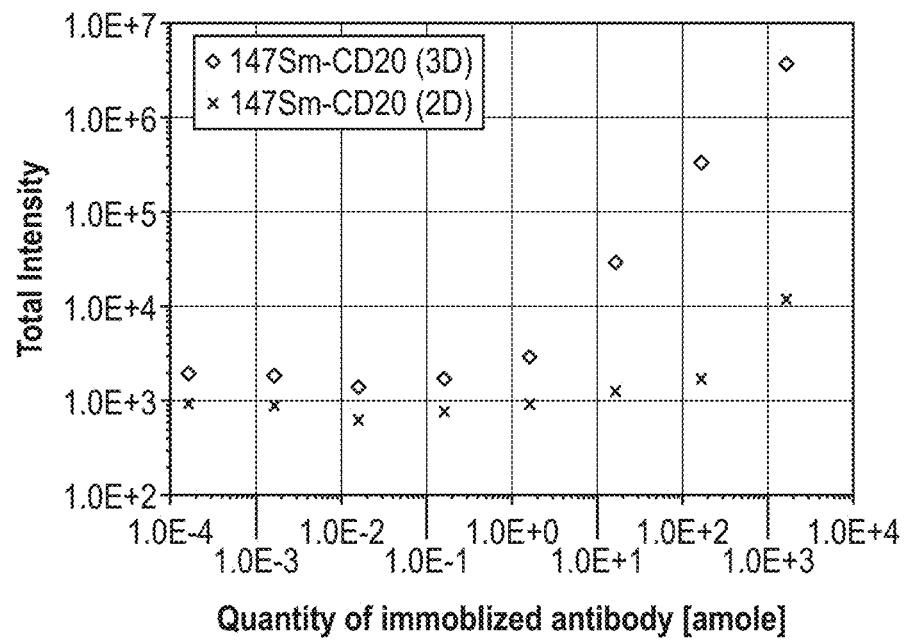
FIGS. 5 and 6. Comparison of substrates with 2D and 3D surfaces for multiplex antibody spotting and acquisition using IMC. Different quantities of metal-tagged antibody were manually spotted on protein A/G activated (2D) and NHS-activated hydrogel coated (3D) glass slides followed by quenching and rinsing with washing buffer and ddH2O. Graphs show total intensities per ablation area (500×500 µm) versus amount of antibody immobilized (amol) per ablation area. Each point represents the mean signal intensity of triplicate IMC acquisitions.
Figure 5:
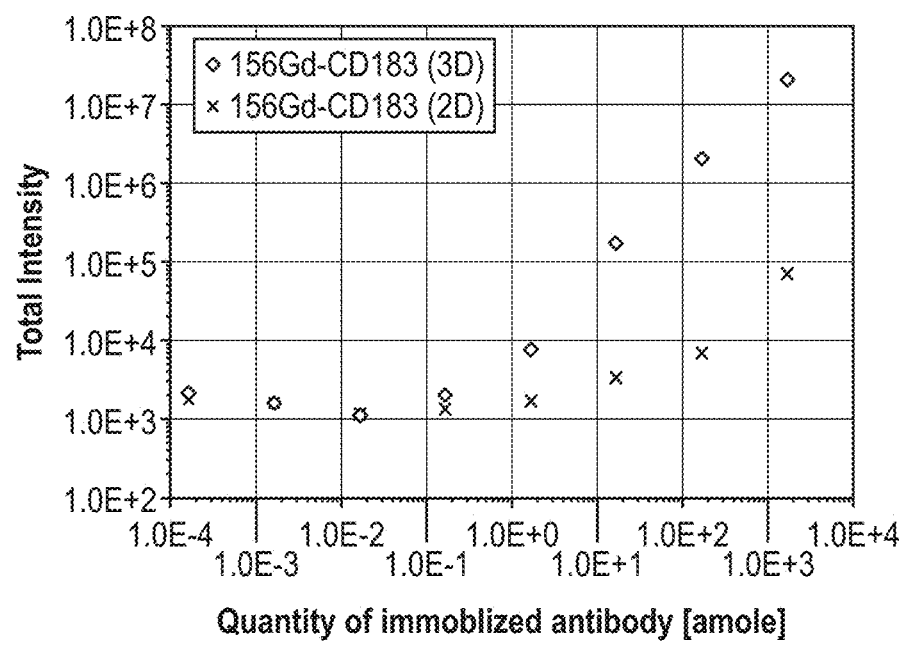
Figure 5:
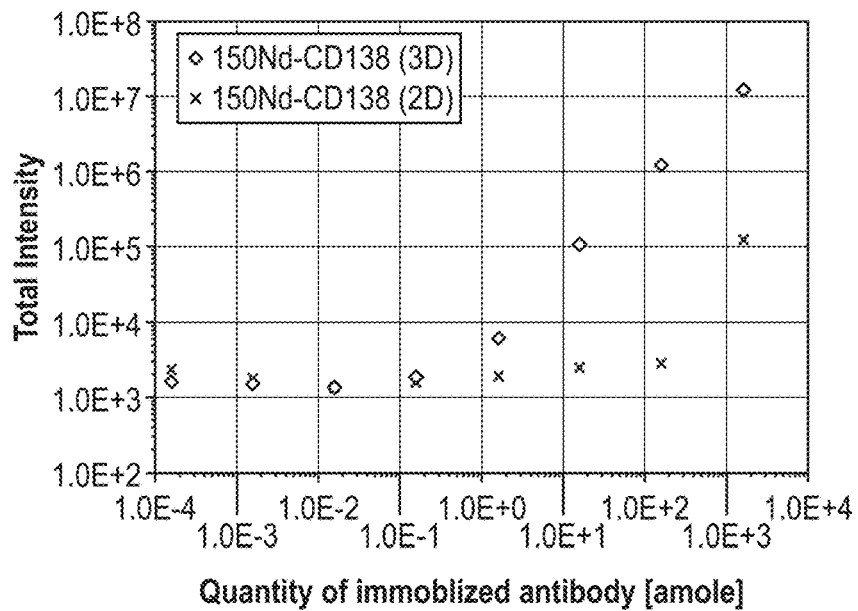
Figure 5:
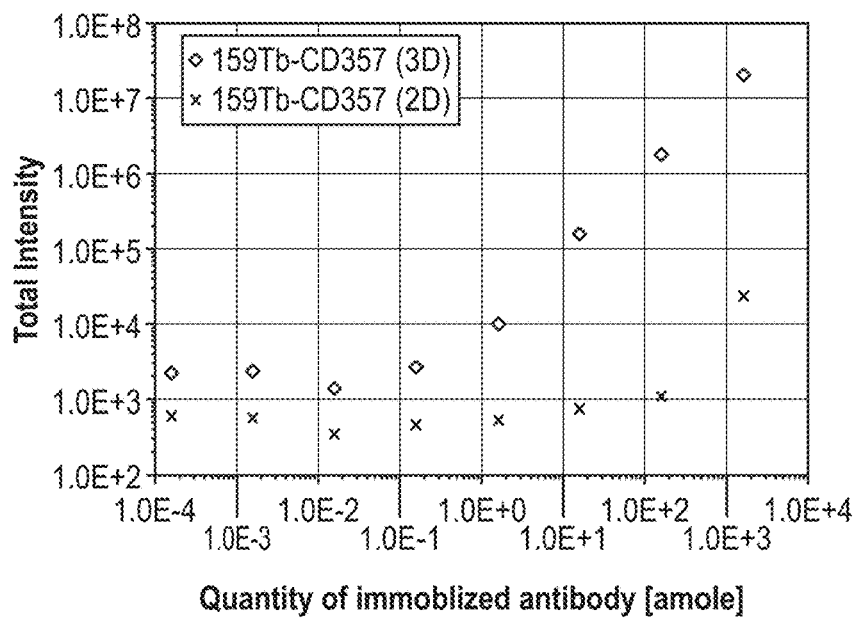
Figure 6:
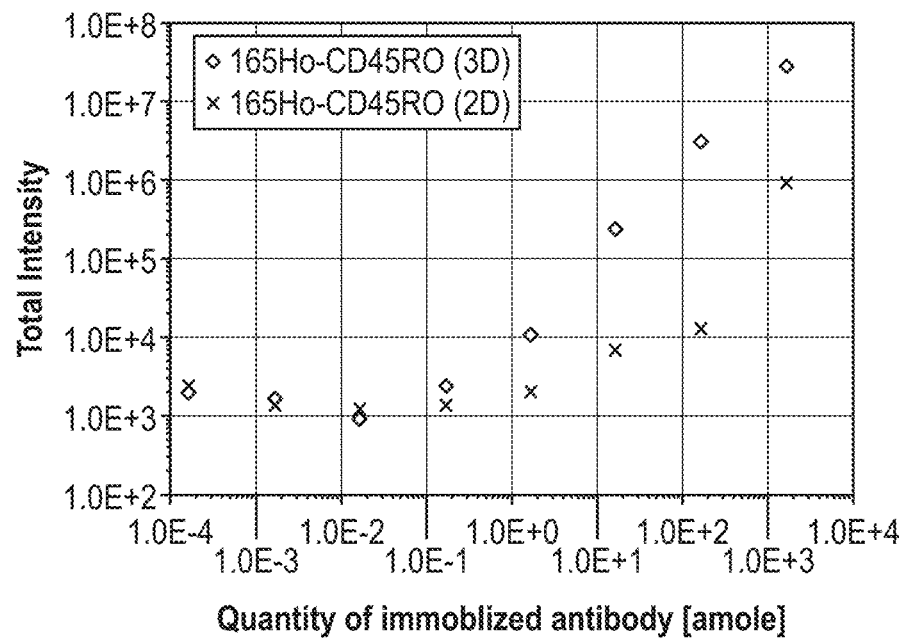
Figure 6:
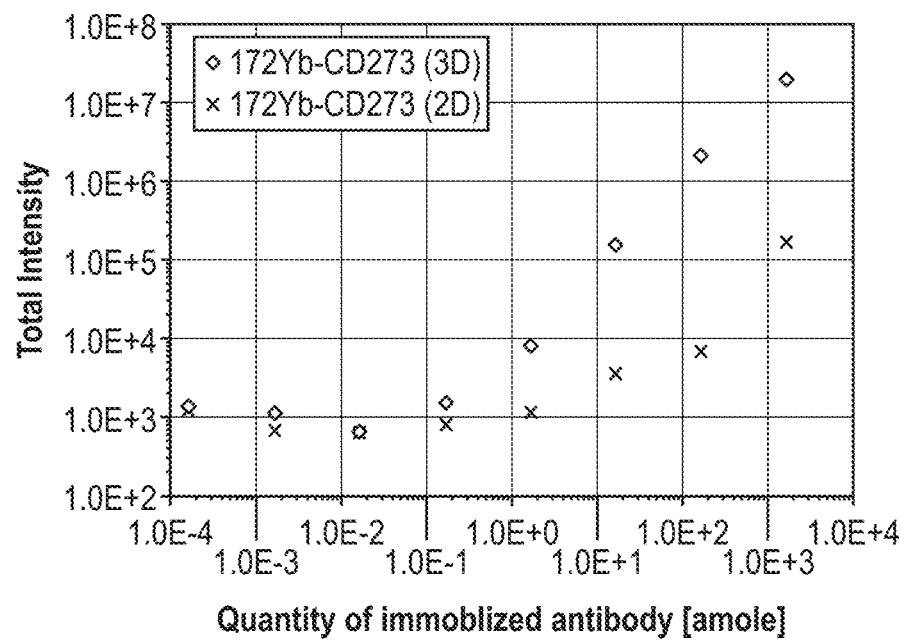
Figure 6:
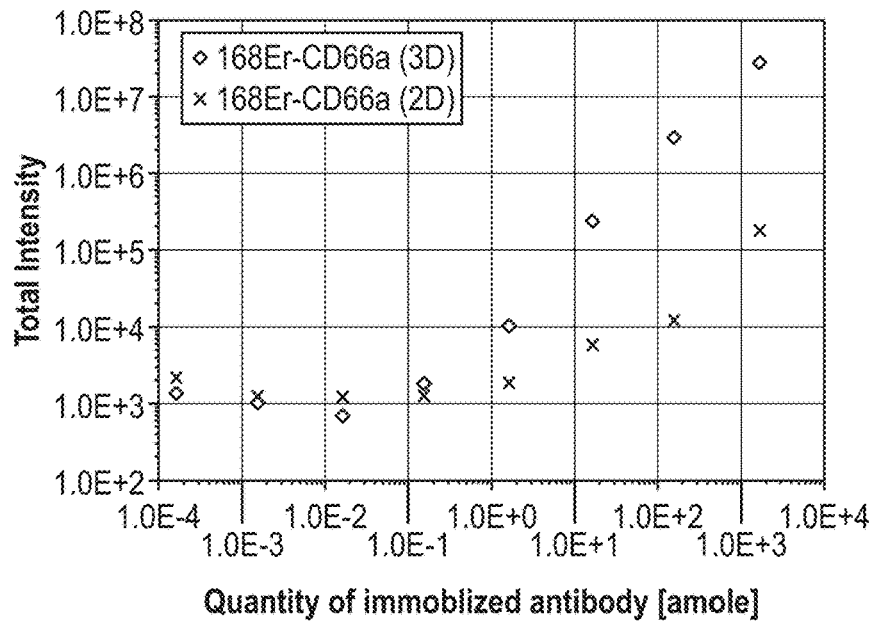
Figure 6:
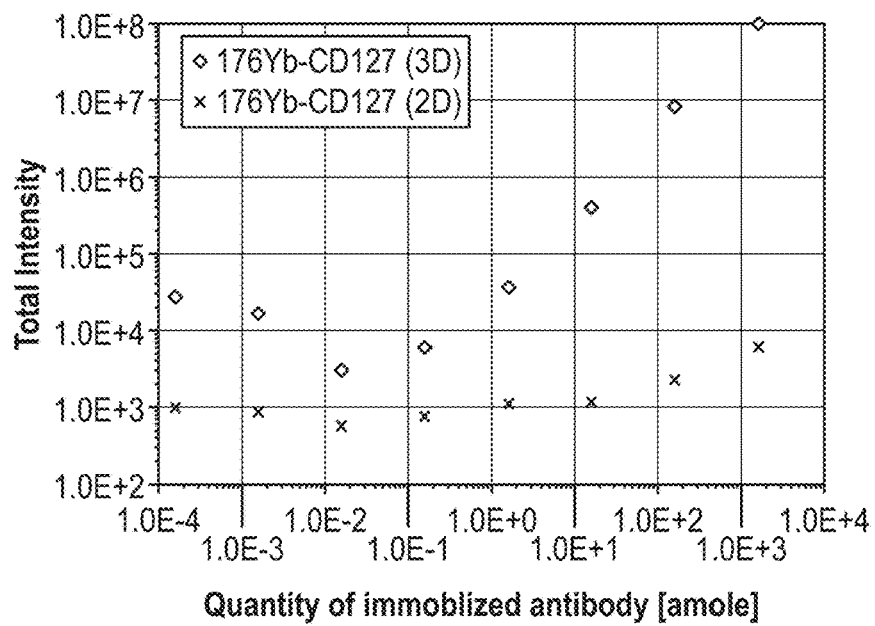

The total ion count determined from different sample concentrations are shown in FIG. 4A. The total ablation area was 500×500 µm$^2$, with each "pixel", or ablation zone, covering an area of 1 µm$^2$. A total of 250000 pixels are therefore ablated per ablation area. The total ion count corresponds to the sum total of ions counted across the entire area. A very low level ion count was recorded at a sample concentration of $6.46 \times 10^{-4}$ µM. Approximately $1 \times 10^8$ ion counts were detected at a sample deposition concentration of $6.46 \times 10^{-2}$ µM. The total ion count increased to $4 \times 10^8$ when the sample concentration was increased 100-fold to 6.46 µM, FIG. 4B shows the image transformed from the ion count per pixel area. The circular spot indicates the sample deposition area. The dark regions outside of the circumference of the deposition area corresponds to non-labelled, image surface. Sample deposition features such as vein-like structures are clearly resolved in the image.

This experiment shows that mass cytometry can be used to aggregately calculate the total ion count in a non-covalently immobilised labelled sample. The total ion count can be used to determine the absolute concentration of a sample. It also demonstrates the capacity of the technique to record differences in the concentration of labelling atom across the spot.

Exemplary Protocol for DNA Spotting:
1. A solid surface coated with appropriate materials to maximize the efficiency of macromolecule attachment was obtained. For the image in FIG. 4A a Nexterion Slide E was used to maximize covalent binding of the DNA oligo to the solid surface.
2. DNA Oligo Conjugated to X8 Polymer was diluted in TE to less than 10 µM and manually or w/machine spot 1 µL or less onto Nexterion Slide E.
3. Slide sat in humid chamber for 30 mins and let to dry overnight
4. Baked for 4 hrs on heat block at 80° C. washed 0.1% Triton in PBS for 5 mins
5. Washed in 1 mM HCL for 2 min (2×)
6. Washed in 100 mM KCL for 10 min
7. Rinsed in $H_2O$ for 1 min
8. Let to dry and spots ablated in IMC Example 4—Preparation of Mass Cytometry Sample Carriers with 3D Polymer-Brush Substrates Based on Polymerisation of Methacrylate Subunits 3D polymer-brush substrates for protein microarray fabrication were prepared from GMA-co-PEGMA or GMA-co-HEMA polymers by Surface-Initiated Atom Transfer Radical Polymerization (SI-ATRP) on glass substrates.

First, the glass substrate of the mass cytometry sample carrier was cleaned using KOH and piranha solution (a mixture of sulfuric acid ($H_2SO_4$) and hydrogen peroxide ($H_2O_2$), used to clean organic residues off substrates). Because the mixture is a strong oxidizing agent, it removes most organic matter, and also hydroxylates most surfaces. The resulting hydroxyl groups were then reacted with (3-aminopropyl)triethoxysilane (APTES), thereby silanizing the glass slide and introducing an amine functional group from which polymers can be initiated to form the 3D polymer brushes, This first 2D silane layer can assist in preventing non specific adsorption of biomolecules to the substrate.

A variety of monomers can be used to form the polymer brushes on the mass cytometry sample carrier following further activation of the amine by reaction with α-bromoisobutyryl bromide (BIB) in the presence of triethyl amine (TEA) and dichloromethane to act as the macroinitiator in a surface initiated atom transfer radical polymerisation (SI-ATRP). In one instance, the co-polymer was formed of glycidyl methacrylate and poly(ethylene glycol) methacrylate subunits. The epoxide group of the glycidyl methacrylate acts as a functionality which can be used to bind capture elements, or a functionality that can be reacted in turn with various further reagents to provide the required functionalities for immobilising capture agents.

In a second instance, the co-polymer was formed of glycidyl methacrylate and 2-hydroxyethyl methacryate (reaction conditions, methanol/H2O, CuBr/bipy at 30° C. under Argon). Again the epoxide group of the glycidyl methacrylate acts as a functionality which can be used to bind capture elements.

One of skill in the art would immediately appreciate that the co-polymer generated here is merely an example. For example, instead of glycidyl methacrylate, another subunit with a different (i.e. non-epoxide) functionality might be employed. Rather than PEGMA or HEMA, other "spacer" co-monomers, or combinations there, might be used. The purpose of these "spacer" groups is to control the hydrophobicity/hydrophilicity of the copolymer. As the polymer layer is to be used for immobilisation of molecule from solution, the selection of co-polymer must have sufficient hydrophilicity to permit molecules from the solution to permeate the polymer layer and so become immobilised on functionalities on the polymer brushes. Porosity of the co-polymer can also be controlled, for instance by selection of the PEG mass on the PEGMA monomer subunits, and the ratio of monomers included in the reaction mixture.

Example 5—Preparation of Mass Cytometry Sample Carriers with 3D Polymer-Brush Substrates Zwitterionic Polymer Brushes This strategy combines the 2D and 3D structures to achieve low nonspecific binding and high loading of capture elements. First the substrate of the mass cytometry sample carrier (e.g. a glass slide) was modified using an alkyl bromide terminated self-assembled monolayer (SAM).

In brief, first, the glass surface was modified using an alkyl bromide terminated self-assembled monolayer (SAM). Then, the slides were submerged in a methanolic solution containing initiator, catalyst, and monomer under nitrogen protection and allowed to react until the required coating thickness is achieved. A hierarchical platform with an ultralow fouling first layer and high loading second layer is achieved using "termination" and "regeneration" approaches. The resultant coating exhibited ultra-low nonspecific binding and high loading of molecular recognition elements.

In particular, first, glass substrates were were washed with pure ethanol, cleaned under UV light, and washed with water and pure ethanol. The initiator SAMs were formed by the substrates in a pure ethanol solution of 1 mM ω-mercaptoundecyl bromoisobutyrate at room temperature for 24 hours. Before the polymerization, the substrates were rinsed with pure ethanol, followed by THF and dried in a stream of nitrogen. This formed the SAM, which terminates with an alkyl bromide.

The SAM coated substrate of the mass cytometry sample carrier (comprising the immobilized initiators) was then placed under nitrogen protection. Carboxybetaine methacrylate (as the monomer of the zwitterionic polymer to be grown) and 2,2'-bipyridine (BPY; as a ligand) were introduced in a 1:1 solution of water and methanol. CuBr was used as a catalyst, and the reaction proceeded by radical initiator-terminated SAMs via ATRP. For a typical polymerization, the substrate was reacted with 7.5 mmol CBMA, 2 mmol BPY and 1 mmol CuBr in 25 mL $CH_3OH/H_2O$ (1:1 volume ratio) for 1 hour under nitrogen protection. The thickness of the coating was controlled by the length of time the polymerisation reaction was left to proceed for.

It is possible to control the density of the polymer grown from the SAM by controlling the number of initiator terminators on the SAM before the polymerisation of the zwitterionic monomer. For instance, for the SAM discussed above which results in an alkyl bromide terminator, the bromine can be substituted for an azide. The proportion of bromines substituted for azides then determines the density of the brushes of the zwitterionic polymer, because the polymerisation reaction only proceeds from the alkyl bromide terminated SAMs. Reducing the number of alkyl bromide terminated SAMs by substitution for azide was noted to increase the depth of the 3D polymer brush layer in Huang et al. (2012, Adv. Mater. 24, 1834-1837). This was proposed to be due to rapid bimolecular termination at high initiator densities. Substitution with azide groups was achieved by incubation in aqueous azide solution, with time and concentration viable to control the degree of replacement of bromide with azide. Typical conditions are 100 mM aqueous azide for 120 minutes. After this step carboxybetaine methacrylate acrylate polymerisation could proceed as above.

In an alternative method for generating the 2D SAM to which a 3D polymer brush could be attached, the SAM was generated using surface initiated photoiniferter-mediated polymerization (SI-PIMP). To begin, the cleaned sample support was incubated by soaking overnight in DCTA (2 mM; synthesised as described in T. Otsu, J. Polym. Sci. Part a—Polym. Chem. 2000, 38, 2121) in THF, followed by rinsing with THF and drying in air. A first polymer layer was then prepared by polymerising carboxybetaine monomer in methanol in the presence of tetraethylthiuram disulfide (TED), which prevents excess chain termination due to chain-chain radical recombination. Following this, a second polymerisation step was performed in the absence of TED, in 90% water/methanol.

In this example, the resulting polymer brushes have a carboxyl functionality resulting from the zwitterionic carboxybetaine subunits. Biological molecules such as proteins and sugars can be coupled by free amine groups to the carboxyl groups by reaction with EDC (1-ethyl-3-(3-dimethylaminopropyl)carbodiimide hydrochloride) (commercially available from e.g. Thermofisher) The efficiency of reaction can be improved by performance of the reaction in the presence of Sulfo-NHS (also commercially available from e.g. Thermofisher).

Example 6—Functionalised Polysaccharide Hydrogel Coated Mass Cytometry Sample Carrier Polysaccharide hydrogels (e.g. Carboxymethylated dextran (CMD), amino modified dextrans, Hydrazomodified dextrans, etc.) can also be used to coat mass cytometry sample carriers, and are attractive for this microarray application due to their outstanding bio-inertness and extremely high protein immobilization capacity.

The mass cytometry sample carrier substrate can be reacted with (3-aminopropyl)triethoxysilane (APTES), thereby silanizing the glass slide and introducing an amine functional group from which polymers, This silane layer can assist in preventing non specific adsorption of biomolecules to the substrate. As silane layer terminates in free amines, the carboxyl groups of e.g. carboxy methylated dextran (CMD) can be reacted with the amines via carbodiimide chemistry. By performing the reaction under conditions such that each carbohydrate polymer reacts with the silane layer at only a few of the carboxy groups, the polymer can be made to form molecular brushes, with the length of the brushes controlling the thickness of the polymer layer. Alternatively epoxysilane can be used, and the dextran coupled to the epoxy group. The properties of the carbohydrate layer can be controlled based on the choice of the dextran immobilised including the use of mixtures of dextrans of different molecular weights.

The component methods for producing functionalised mass cytometry sample carriers of this type are set out below:

Glass Cleaning Protocol:
1. Rinse slides with distilled water
2. After drying, immerse slides in a solution of 10% KOH in methanol and incubate static for 2 h.
3. Remove slides from the methanolic KOH solution and rinse exhaustively with distilled water until no Schlieren lines were observed.
4. Store dried slides in DI water until needed for experiments or additional surface treatments.

Carboxymethylation of Dextran
1. Dissolve 400 mg of dextran (different combinations of Fisher Scientific, Cat #AAJ6370218 (500 kDa), AAJ6020022 (250 kDa, AAJ6098922 (75 kDa), or AAJ6378922 (150 KDa) can be used) in 10 mL of 3 M NaOH containing 1 M monochloroacetic acid.
2. Stir the solution for 2 h at room temperature (RT).
3. Stop the reaction by adding 40 mg of NaH2PO4 followed by pH adjustment to neutral using 18 M H2SO4.
4. Filter the solution through a 0.2 μm PTFE filter, dialyzed five times against Milli-Q water for 1 h to remove reagents and salts.
5. Lyophilize and store lyophilized CMD powder at 4° C. until use (Note: The carboxymethylation degree of our product was assessed using 1H NMR spectroscopy.)

Carboxymethyl Dextran Grafting on Aminosilane Coated Slides
1. Start with dried cleaned slides.
2. Dissolve 99% APTES in anhydrous toluene at a concentration of 10 mM.
3. Immerse slide in a APTES solution for 3 hr at RT.
4. Rinse slides twice with toluene to remove unreacted silane.
5. After dried, bake slides at 120° C. for 30 min anneal the silane coating.
6. Rinse the surface by soaking them in freshly distilled toluene for 5 min.
7. Prepare CMD solutions by dissolving at 2 mg/ml in Milli-Q water.
8. Perform NHS activation by adding 150 ul EDC (40 mM in MilliQ water) and 150 ul NHS (10 mM in MilliQ water) to the CMD solutions.
9. Immerse the amino-coated surfaces in the NHS-activated CMD solution for 2 h at RT.
10. Rinse slides twice with PBS in ultrasonic bath and three times using MilliQ water.
11. Air dry and store at 4° C.

Preparation Carboxymethyl Dextran Grafting on Epoxyslilane Slides
1. Immerse the slides in a 2% solution of 3-glycidoxypropyltrimethoxysilane (GPTMS) in toluene.
2. After 1 hr incubation at room temperature, bake the slides at 150° C. for at least 2 h to anneal the silane coating.
3. Rinse epoxy-silanized glass slides thoroughly with ethanol, and either air-dry or dry under a stream of nitrogen until use.
4. Prepare CMD solutions by dissolving at 2 mg/ml in Milli-Q water.
5. Immerse epoxy coated glasses to the CMD solution and incubate for 24 h, and rinse by ddH2O.
6. Quench the remaining epoxy groups with a solution of 2 mM aspartic acid in 0.5 M sodium carbonate buffer (pH 9.0).
7. Rinse slides in ultrasonic bath three times using MilliQ water.
8. Air dry and store at 4° C.

Example 7—Protein Array Designs

Figure 7:
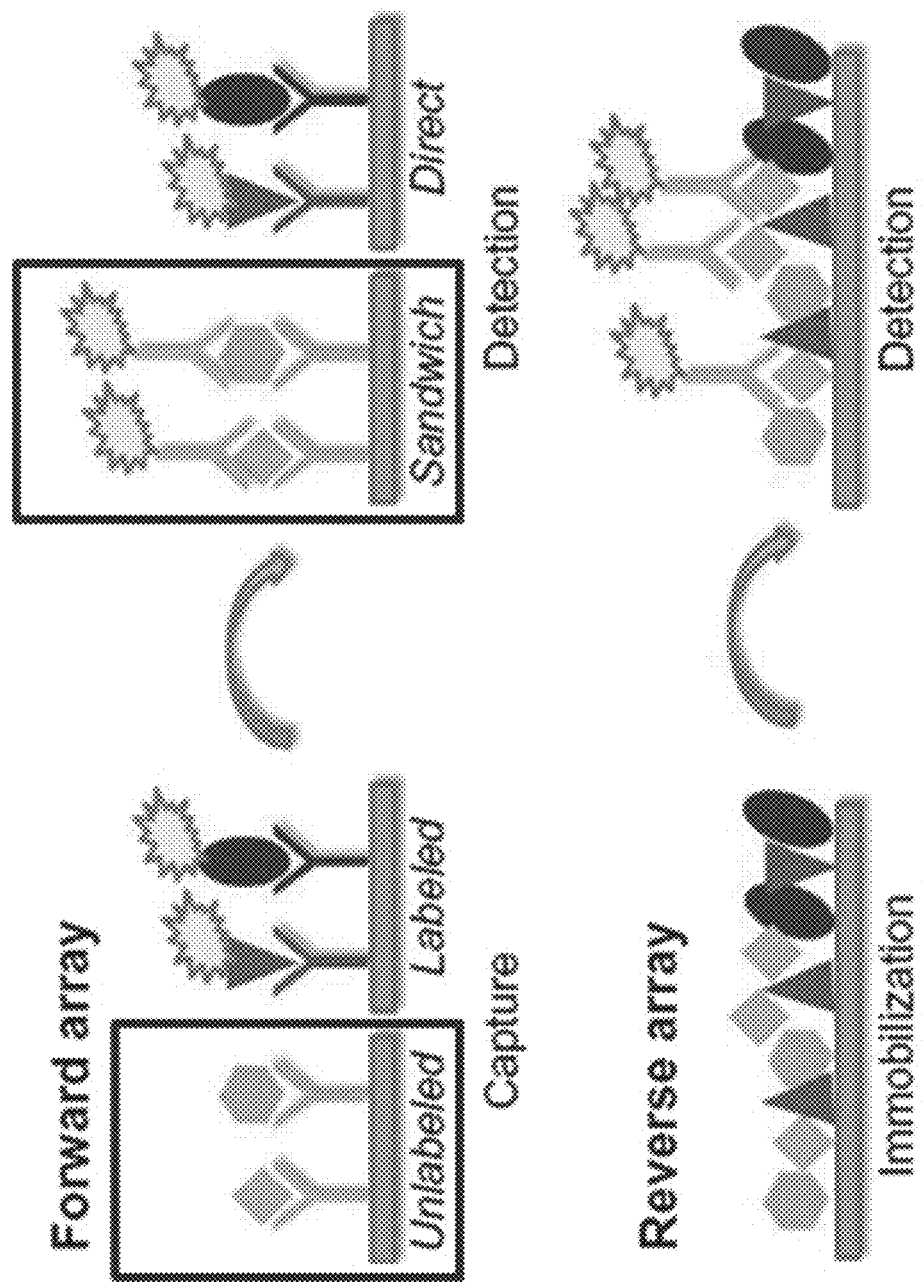
FIG. 7. Diagram of protein array of certain embodiments, which may include an antibody (forward array) or target protein (reverse array) immobilized on one or more spots of a solid support.

As described in FIG. 7, a protein array of certain embodiments may comprise an antibody (forward array) or target protein (reverse array) immobilized on one or more spots of a solid support. In a forward array, unlabeled or labelled (e.g., mass tagged) target proteins may be bound by the immobilized antibodies. When unlabeled protein is bound, the forward array may be contacted with mass tagged reporter antibodies that specifically bind the unlabeled proteins. In a reverse array, immobilized protein is contacted with mass tagged reporter antibodies.

Example 8—Detection of TNF-α and IL-2 in a Reverse Array

TNF-α and IL-2 were spotted at various concentration in wells comprising a hydrogel. The spots were contacted with a reporter antibody to TNF-α (mass tagged with a 152S metal polymer) and a reporter antibody to IL-2 (mass tagged with a 158Gd metal polymer). Mass tags were detected by LA-ICP-MS. As shown in FIG. 8, a linear relationship between the mass signal and concentration was identified for both TNF-α and IL-2 in the range around 10 μg/ml to 100,000 μg/ml.

Example 9—Analysis of Microarray Gene Expression Data Across a Plurality of Samples A hypothetical mass tagged gene expression array (IMC-DNA-MA) experiment is described below, for the purpose of illustration.

The general idea behind the below workflow is: (1) is to substitute fluorescence-based detection of the hybridized oligos used in conventional microarrays, such as Illumina and Affymetrix, with the existing technology of Imaging Mass Cytometry with metal-loaded polymer-based detection. A main advantage is high sample multiplexing capability of IMC-DNA-microarrays against a mixture of only two samples in conventional microarray technologies. (2) New IMC-DNA-MA analysis is proposed in this disclosure as a quick method to identify trends of similarity/difference between IMC-DNA-MA sample data and data from secondary microarrays available from public databases such as Gene Expression Omnibus (GEO) repository and other open repositories. Said analysis can be cross-referenced with other analytical tools, such as Gene Ontology, Wikipathways, KEGG—Kyoto Encyclopedia of Genes and Genomes, PID—Pathway Interaction Database, and Reactome Pathway Database. Just to indicate where we try to fit in our analysis.

For context, in some fluorescent approaches, each probe hybridizes a specific cDNA sequence under stringent conditions. There cDNAs are reverse transcribed (RT) from RNA collected from two samples, experimental and control. During RT step DNA incorporates aminoallyl-UTPs present in the substrate reaction master mix. During the next step cDNA is reacted with NHS-activated ester dye to attach the dye to the amine group, such as Cy3 (emits light in green region of the spectrum) and Cy5 (red region), for two samples. Dye-labelled DNA from two samples is mixed together in equal amounts and hybridized on the microarray, detected and scanned on the instrument with the appropriate laser and detector.

IMC-DNA-MA utilizes the same type of the substrate with printed reporters with spatial specifications for slide working area of the IMC instrument. Sample preparation is different and requires the use of the metal-loaded DOTA derivatives with amine reactive NCS group. These polymers, p-SCN-Bn-DOTA, are commercially available, e.g. in the names of X-205, X-207, X-209 from Macrocyclics.

Standard microarray hybridization protocol is lengthy and known to one of skill in the art. The protocol may require modification to accommodate polymer kinetics at a certain temperature and pH. These polymers can be loaded with lanthanides or other available metals, such as Cd, Hf, Bi, etc. Each polymer loaded with a metal can be hybridized to cDNA from one sample. The theoretical limitation of the number of samples in the final mix corresponds with the number of available isotopes. Practically, the main limitation is the number of free oligonucleotides in each spot on the microarray since they can be occupied and, hence, depleted faster with the increasing number of samples. However, the maximum number of samples for multiplexing to run on a single glass slide is much greater than 2 and can be established empirically. After the hybridization step, the slide may be ablated on an IMC instrument similar to standard IMC tissue imaging procedure. The slide may contain calibration reporters (e.g., an element standard) with appropriate metal (e.g film or beads) for normalization since signal intensity varies between different metals.

Figure 9:
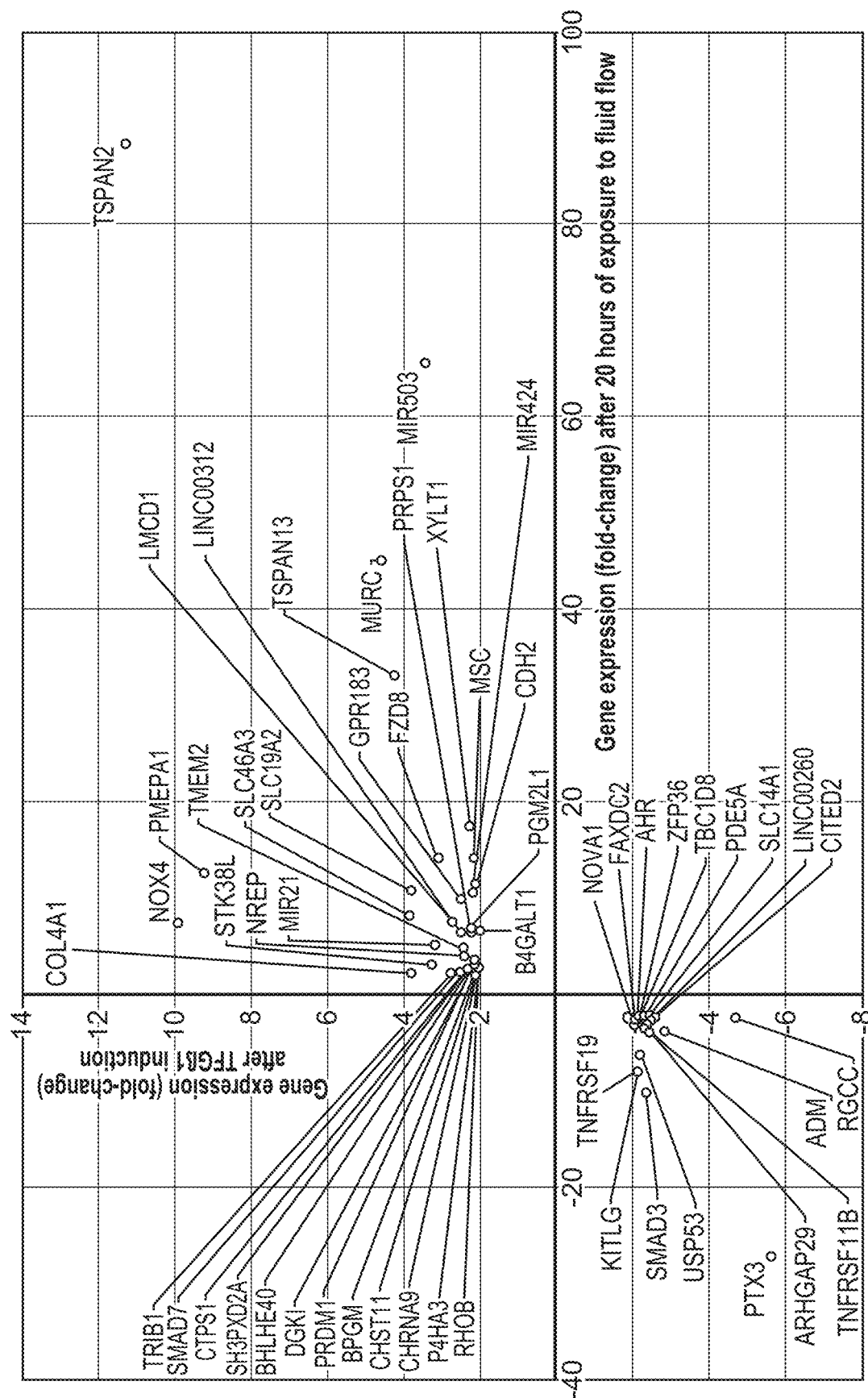
FIG. 9. Graph of gene expression (fold change) with axes representing different conditions according to embodiments of the present invention.

Tools for data analysis are publically available, for example, as are documented in a thesis by Nikita Zabinyakov entitled "Shear Stress Modulates Gene Expression in Normal Human Dermal Fibroblasts", and submitted to the Graduate Program in Biomedical Engineering in Calgary, Alberta on January 2017. Said thesis identifies differentially expressed genes across a plurality of different signalling pathways (see, for example, Table 5). FIG. 16 of said Thesis analyses the fold change in expression of two different treatment conditions (static vs. flow treatment of fibroblasts, and untreated vs. TGF-B1 treatment of fibroblasts). Genes are organized by the delta between these two conditions in fold change of gene expressions. As shown in FIG. 9 of the subject application, the data from FIG. 16 could alternately be represented with the gene expression (fold change) of a different treatment condition on each axis. These analysis illustrate that samples from different array experiments can be compared to one another to answer interesting biological questions (e.g., does shear stress have a similar effect to TGFB1 induction?). Further, running these samples together on the same microarray (using a distinct element tagged cDNA from each sample) would allow for direct comparisons across more than 2 samples (treatment conditions), controlling for variance across arrays and experiment runs. Sample multiplexed data obtained by IMC-DNA-MA may be anayzed (e.g., by any of the above described methods) such that expression data for genes across a plurality of samples is visualized, and relationships or patterns of gene expression between samples (e.g., treatment conditions) are called out.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention.

Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the analyte" includes reference to one or more analytes and equivalents thereof known to those skilled in the art, and so forth. The invention has now been described in detail for the purposes of clarity and understanding. However, it will be appreciated that certain changes and modifications may be practice within the scope of the appended claims. As used herein, "invention" refers to "embodiments of the present invention," unless context clearly dictates otherwise.

All publications, patents, and patent applications cited herein are hereby incorporated by reference in their entirety for all purposes. None is admitted to be prior art.

What is claimed is:

1. A sample carrier for mass cytometry, the sample carrier comprising:
    a planar surface, the planar surface including a first region for binding a sample;
    a polydopamine layer disposed on the planar surface;
    a self-assembled monolayer disposed on the polydopamine layer;
    a 3D polymer brush attached to the self-assembled monolayer;
    an element standard, the element standard comprising one or more elements or isotopes, wherein:
        the element standard comprises an element film applied to a second region of the planar surface using an adhesive,
        the element film is a polymer element film, and
        the first region does not overlap with the second region.

2. The sample carrier of claim 1, wherein the element standard comprises consistent abundance of the one or more elements or isotopes across the element standard.

3. The sample carrier of claim 1, wherein the element standard comprises separate regions, each with a different amount of the one or more elements or isotopes.

4. The sample carrier of claim 1, wherein different regions of the element standard may comprise a different combination of elements or isotopes.

5. The sample carrier of claim 1, wherein the element standard comprises reference particles of known elemental or isotopic composition, wherein the reference particles comprise metal elements or isotopes.

6. The sample carrier of claim 5, wherein the reference particles are optically resolvable.

7. The sample carrier of claim 5, wherein the reference particles comprise a metallic nanocrystal core and/or polymer surface.

8. The sample carrier of claim 1, wherein the element film is a polyester element film.

9. The sample carrier of claim 1, wherein the polymer element film comprises a long chain polymer that was mixed with a metal solution and volatile solvent prior to the solvent being evaporated.

10. The sample carrier of claim 1, wherein the element film comprises at least 10 different elemental isotopes, wherein the elemental isotopes have masses over 60 amu.

11. The sample carrier of claim 10, wherein the average number of the majority of elemental isotopes across the element film has a coefficient of variation (CV) of less than less than 10%.

12. A method of normalizing data obtained from a sample based on the element standard of the sample carrier of claim 1, wherein the sample comprises mass tags comprising labelling atoms, and wherein the method comprises analysing the sample by mass spectrometry.

13. The method of claim 12, further comprising using the element standard to generate a standard curve.

14. The method of claim 12, wherein the sample carrier is a sample slide comprising the sample, and further comprising applying the element film to the sample slide after tagging the sample with mass tags.

15. The method of claim 12, wherein normalization comprises quantification of the labelling atoms.

16. The sample carrier of claim 9, wherein the polymer is poly (methyl methacrylate) and the solvent is toluene.

17. The sample carrier of claim 9, further comprising the sample bound to the first region, wherein the sample is a biological sample.

18. The sample carrier of claim 9, wherein the element film is at least 100 square millimeters.

19. The method of claim 12, wherein the normalizing the data comprises analysing the element standard by mass spectrometry after analysing the sample.

20. A method comprising:
 binding the sample to the sample carrier of claim 1;
 ablating the element standard to form an ablation plume;
 transferring the ablation plume to a detector; and
 analysing the sample using the detector after transferring the ablation plume to the detector.

* * * * *